US008795306B2

(12) United States Patent
Smith et al.

(10) Patent No.: US 8,795,306 B2
(45) Date of Patent: Aug. 5, 2014

(54) ATHERECTOMY APPARATUS, SYSTEMS AND METHODS

(71) Applicant: AtheroMed, Inc., Menlo Park, CA (US)

(72) Inventors: Torrey Smith, Redwood City, CA (US); Douglas E. Rowe, San Jose, CA (US); August Christopher Pombo, Sacramento, CA (US); Paul Quentin Escudero, Redwood City, CA (US); Christopher J. Danek, San Carlos, CA (US); John T. To, Newark, CA (US)

(73) Assignee: AtheroMed, Inc., Menlo Park, CA (US)

( * ) Notice: Subject to any disclaimer, the term of this patent is extended or adjusted under 35 U.S.C. 154(b) by 0 days.

(21) Appl. No.: 14/069,303

(22) Filed: Oct. 31, 2013

(65) Prior Publication Data

US 2014/0058423 A1 Feb. 27, 2014

Related U.S. Application Data

(63) Continuation of application No. 13/652,352, filed on Oct. 15, 2012.

(60) Provisional application No. 61/546,888, filed on Oct. 13, 2011.

(51) Int. Cl.
*A61B 17/22* (2006.01)

(52) U.S. Cl.
USPC .......................................... 606/159; 604/525

(58) Field of Classification Search
USPC ........... 606/159, 167, 170, 180; 604/525, 530
See application file for complete search history.

(56) References Cited

U.S. PATENT DOCUMENTS

| | | |
|---|---|---|
| 3,358,472 A | 12/1967 | Klipping |
| 4,167,944 A | 9/1979 | Banko |
| 4,445,509 A | 5/1984 | Auth |
| 4,598,710 A | 7/1986 | Kleinberg et al. |
| 4,631,052 A | 12/1986 | Kensey |
| 4,669,469 A | 6/1987 | Gifford, III et al. |
| 4,690,140 A | 9/1987 | Mecca |
| 4,696,667 A | 9/1987 | Masch |
| 4,770,652 A | 9/1988 | Mahurkar |
| 4,781,186 A | 11/1988 | Simpson et al. |
| 4,790,812 A | 12/1988 | Hawkins, Jr. et al. |
| 4,804,364 A | 2/1989 | Dieras et al. |

(Continued)

FOREIGN PATENT DOCUMENTS

| | | |
|---|---|---|
| EP | 0 254 414 A1 | 1/1988 |
| EP | 0 817 594 B1 | 6/2002 |

(Continued)

OTHER PUBLICATIONS

Final Office Action mailed on Jan. 29, 2014 for U.S. Appl. No. 13/715,664, filed Dec. 14, 2012, 8 pages.

(Continued)

*Primary Examiner* — Victor Nguyen
(74) *Attorney, Agent, or Firm* — Morrison & Foerster LLP

(57) ABSTRACT

Described here are devices and methods for performing atherectomies. Generally, the atherectomy devices include a handle, a cutter assembly, and a catheter or catheter assembly therebetween. The cutter assembly includes a cutter housing and a cutter having a first cutting element and a second cutting element, each of which can be rotated relative to the atherectomy device to cut occlusive material.

10 Claims, 34 Drawing Sheets

(56) References Cited

U.S. PATENT DOCUMENTS

| | | | |
|---|---|---|---|
| 4,808,153 A | 2/1989 | Parisi | |
| 4,844,064 A | 7/1989 | Thimsen et al. | |
| 4,857,045 A | 8/1989 | Rydell | |
| 4,857,046 A | 8/1989 | Stevens et al. | |
| 4,886,490 A | 12/1989 | Shiber | |
| 4,887,599 A | 12/1989 | Muller | |
| 4,894,051 A | 1/1990 | Shiber | |
| 4,911,148 A | 3/1990 | Sosnowski et al. | |
| 4,950,277 A | 8/1990 | Farr | |
| 4,994,067 A | 2/1991 | Summers | |
| 5,074,841 A | 12/1991 | Ademovic et al. | |
| 5,100,426 A | 3/1992 | Nixon | |
| 5,114,399 A * | 5/1992 | Kovalcheck | 604/22 |
| 5,122,134 A | 6/1992 | Borzone et al. | |
| 5,231,989 A | 8/1993 | Middleman et al. | |
| 5,242,461 A | 9/1993 | Kortenbach et al. | |
| 5,267,955 A | 12/1993 | Hanson | |
| 5,282,813 A | 2/1994 | Redha | |
| 5,282,821 A | 2/1994 | Donahue | |
| 5,284,128 A | 2/1994 | Hart | |
| 5,312,427 A | 5/1994 | Shturman | |
| 5,314,438 A | 5/1994 | Shturman | |
| 5,320,635 A | 6/1994 | Smith | |
| 5,334,211 A | 8/1994 | Shiber | |
| 5,356,418 A | 10/1994 | Shturman | |
| 5,358,472 A | 10/1994 | Vance et al. | |
| 5,360,432 A | 11/1994 | Shturman | |
| 5,370,609 A | 12/1994 | Drasler et al. | |
| 5,372,587 A | 12/1994 | Hammerslag et al. | |
| 5,409,454 A | 4/1995 | Fischell et al. | |
| 5,423,799 A | 6/1995 | Shiu | |
| 5,429,604 A | 7/1995 | Hammersmark et al. | |
| 5,429,617 A | 7/1995 | Hammersmark et al. | |
| 5,431,173 A | 7/1995 | Chin et al. | |
| 5,456,680 A | 10/1995 | Taylor et al. | |
| 5,474,532 A | 12/1995 | Steppe | |
| 5,489,291 A | 2/1996 | Wiley | |
| 5,501,653 A | 3/1996 | Chin | |
| 5,520,609 A | 5/1996 | Moll et al. | |
| 5,529,580 A | 6/1996 | Kusunoki et al. | |
| 5,540,706 A | 7/1996 | Aust et al. | |
| 5,554,163 A | 9/1996 | Shturman | |
| 5,556,408 A | 9/1996 | Farhat | |
| 5,569,197 A | 10/1996 | Helmus et al. | |
| 5,584,843 A | 12/1996 | Wulfman et al. | |
| 5,618,294 A | 4/1997 | Aust et al. | |
| 5,626,562 A | 5/1997 | Castro | |
| 5,632,755 A | 5/1997 | Nordgren et al. | |
| 5,634,883 A | 6/1997 | Chin et al. | |
| 5,643,178 A | 7/1997 | Moll et al. | |
| 5,643,251 A | 7/1997 | Hillsman et al. | |
| 5,643,297 A | 7/1997 | Nordgren et al. | |
| 5,643,298 A | 7/1997 | Nordgren et al. | |
| 5,649,941 A | 7/1997 | Lary | |
| 5,665,062 A | 9/1997 | Houser | |
| 5,665,098 A | 9/1997 | Kelly et al. | |
| 5,669,926 A | 9/1997 | Aust et al. | |
| 5,690,634 A | 11/1997 | Muller et al. | |
| 5,690,643 A | 11/1997 | Wijay | |
| 5,695,506 A | 12/1997 | Pike et al. | |
| 5,716,327 A | 2/1998 | Warner et al. | |
| 5,725,543 A | 3/1998 | Redha | |
| 5,728,129 A | 3/1998 | Summers | |
| 5,733,297 A | 3/1998 | Wang | |
| 5,743,456 A | 4/1998 | Jones et al. | |
| 5,746,758 A | 5/1998 | Nordgren et al. | |
| 5,755,731 A | 5/1998 | Grinberg | |
| 5,766,196 A | 6/1998 | Griffiths | |
| 5,779,721 A | 7/1998 | Nash | |
| 5,782,834 A | 7/1998 | Lucey et al. | |
| 5,820,592 A | 10/1998 | Hammerslag | |
| 5,843,103 A | 12/1998 | Wulfman | |
| 5,851,208 A | 12/1998 | Trolt | |
| 5,851,212 A | 12/1998 | Zirps et al. | |
| 5,873,882 A | 2/1999 | Straub et al. | |
| 5,876,414 A | 3/1999 | Straub | |
| 5,882,329 A | 3/1999 | Patterson et al. | |
| 5,882,333 A | 3/1999 | Schaer et al. | |
| 5,895,399 A | 4/1999 | Barbut et al. | |
| 5,897,566 A | 4/1999 | Shturman et al. | |
| 5,902,263 A | 5/1999 | Patterson et al. | |
| 5,902,313 A | 5/1999 | Redha | |
| 5,941,869 A | 8/1999 | Patterson et al. | |
| 5,941,893 A | 8/1999 | Saadat | |
| 6,001,112 A | 12/1999 | Taylor | |
| 6,015,420 A | 1/2000 | Wulfman et al. | |
| 6,027,514 A | 2/2000 | Stine et al. | |
| 6,042,593 A | 3/2000 | Storz et al. | |
| 6,048,339 A | 4/2000 | Zirps et al. | |
| 6,053,923 A | 4/2000 | Veca et al. | |
| 6,066,153 A | 5/2000 | Lev | |
| 6,080,170 A | 6/2000 | Nash et al. | |
| 6,090,118 A | 7/2000 | McGuckin, Jr. | |
| 6,132,444 A | 10/2000 | Shturman et al. | |
| 6,139,557 A | 10/2000 | Passafaro et al. | |
| 6,142,955 A | 11/2000 | Farascioni et al. | |
| 6,146,395 A | 11/2000 | Kanz et al. | |
| 6,152,938 A | 11/2000 | Curry | |
| 6,156,046 A | 12/2000 | Passafaro et al. | |
| 6,165,209 A | 12/2000 | Patterson et al. | |
| 6,206,898 B1 | 3/2001 | Honeycutt et al. | |
| 6,238,405 B1 | 5/2001 | Findlay, III et al. | |
| 6,241,744 B1 | 6/2001 | Imran et al. | |
| 6,258,098 B1 | 7/2001 | Taylor et al. | |
| 6,264,630 B1 | 7/2001 | Mickley et al. | |
| 6,299,622 B1 | 10/2001 | Snow et al. | |
| 6,319,242 B1 | 11/2001 | Patterson et al. | |
| 6,355,027 B1 | 3/2002 | Le et al. | |
| 6,371,928 B1 | 4/2002 | McFann et al. | |
| 6,406,442 B1 | 6/2002 | McFann et al. | |
| 6,451,036 B1 | 9/2002 | Heitzmann et al. | |
| 6,454,779 B1 | 9/2002 | Taylor | |
| 6,482,215 B1 | 11/2002 | Shiber | |
| 6,482,217 B1 | 11/2002 | Pintor et al. | |
| 6,494,890 B1 | 12/2002 | Shturman et al. | |
| 6,497,711 B1 * | 12/2002 | Plaia et al. | 606/159 |
| 6,554,846 B2 | 4/2003 | Hamilton et al. | |
| 6,562,049 B1 | 5/2003 | Norlander et al. | |
| 6,565,588 B1 | 5/2003 | Clement et al. | |
| 6,572,630 B1 | 6/2003 | McGuckin, Jr. et al. | |
| 6,579,298 B1 | 6/2003 | Bruneau et al. | |
| 6,579,299 B2 | 6/2003 | McGuckin, Jr. et al. | |
| 6,596,005 B1 | 7/2003 | Drummond et al. | |
| 6,602,264 B1 | 8/2003 | McGuckin, Jr. | |
| 6,623,495 B2 | 9/2003 | Findlay, III et al. | |
| 6,629,953 B1 | 10/2003 | Boyd | |
| 6,638,233 B2 | 10/2003 | Corvi et al. | |
| 6,638,288 B1 | 10/2003 | Shturman et al. | |
| RE38,335 E | 11/2003 | Aust et al. | |
| 6,656,195 B2 | 12/2003 | Peters et al. | |
| 6,666,854 B1 | 12/2003 | Lange | |
| 6,666,874 B2 | 12/2003 | Heitzmann et al. | |
| 6,682,545 B1 | 1/2004 | Kester | |
| 6,702,830 B1 | 3/2004 | Demarais et al. | |
| 6,746,422 B1 | 6/2004 | Noriega et al. | |
| 6,758,851 B2 | 7/2004 | Shiber | |
| 6,790,215 B2 | 9/2004 | Findlay, III et al. | |
| 6,800,085 B2 | 10/2004 | Selmon et al. | |
| 6,808,531 B2 | 10/2004 | Lafontaine et al. | |
| 6,818,001 B2 | 11/2004 | Wulfman et al. | |
| 6,818,002 B2 | 11/2004 | Shiber | |
| 6,830,577 B2 | 12/2004 | Nash et al. | |
| 6,843,797 B2 | 1/2005 | Nash et al. | |
| 6,860,235 B2 | 3/2005 | Anderson et al. | |
| 6,876,414 B2 | 4/2005 | Hara et al. | |
| 6,936,056 B2 | 8/2005 | Nash et al. | |
| 6,997,934 B2 | 2/2006 | Snow et al. | |
| 7,008,375 B2 | 3/2006 | Weisel | |
| 7,025,751 B2 | 4/2006 | Silva et al. | |
| 7,033,357 B2 | 4/2006 | Baxter et al. | |
| 7,037,316 B2 | 5/2006 | McGuckin, Jr. et al. | |
| RE39,152 E | 6/2006 | Aust et al. | |
| 7,172,610 B2 | 2/2007 | Heitzmann et al. | |
| 7,235,088 B2 | 6/2007 | Pintor et al. | |

(56) References Cited

U.S. PATENT DOCUMENTS

| | | |
|---|---|---|
| 7,316,697 B2 | 1/2008 | Shiber |
| 7,344,546 B2 | 3/2008 | Wulfman et al. |
| 7,344,548 B2 | 3/2008 | Toyota et al. |
| 7,381,198 B2 | 6/2008 | Noriega et al. |
| 7,399,307 B2 | 7/2008 | Evans et al. |
| 7,479,147 B2 | 1/2009 | Honeycutt et al. |
| 7,534,249 B2 | 5/2009 | Nash et al. |
| 7,666,161 B2 | 2/2010 | Nash et al. |
| 7,875,018 B2 | 1/2011 | Tockman et al. |
| 7,981,128 B2 | 7/2011 | To et al. |
| 8,007,500 B2 | 8/2011 | Lin et al. |
| 8,007,506 B2 | 8/2011 | To et al. |
| 8,070,762 B2 | 12/2011 | Escudero et al. |
| 8,236,016 B2 | 8/2012 | To et al. |
| 8,337,516 B2 | 12/2012 | Escudero et al. |
| 8,361,094 B2 | 1/2013 | To et al. |
| 8,469,979 B2 | 6/2013 | Olson |
| 8,517,994 B2 | 8/2013 | Li et al. |
| 8,545,447 B2 | 10/2013 | Demarais et al. |
| 8,568,432 B2 | 10/2013 | Straub |
| 8,579,926 B2 | 11/2013 | Pintor et al. |
| 8,585,726 B2 | 11/2013 | Yoon et al. |
| 8,628,549 B2 | 1/2014 | To et al. |
| 8,647,355 B2 | 2/2014 | Escudero et al. |
| 2001/0004700 A1 | 6/2001 | Honeycutt et al. |
| 2001/0005909 A1 | 6/2001 | Findlay, III et al. |
| 2002/0004680 A1 | 1/2002 | Plaia et al. |
| 2002/0007190 A1 | 1/2002 | Wulfman et al. |
| 2002/0029057 A1 | 3/2002 | McGuckin, Jr. |
| 2002/0077642 A1 | 6/2002 | Patel et al. |
| 2002/0169467 A1 | 11/2002 | Heitzmann et al. |
| 2002/0198550 A1 | 12/2002 | Nash et al. |
| 2003/0018346 A1 | 1/2003 | Follmer et al. |
| 2003/0078606 A1 | 4/2003 | Lafontaine et al. |
| 2003/0100911 A1 | 5/2003 | Nash et al. |
| 2003/0114869 A1 | 6/2003 | Nash et al. |
| 2003/0125758 A1 | 7/2003 | Simpson et al. |
| 2003/0139751 A1 | 7/2003 | Evans et al. |
| 2003/0139802 A1 | 7/2003 | Wulfman et al. |
| 2004/0006358 A1 | 1/2004 | Wulfman et al. |
| 2004/0087988 A1 | 5/2004 | Heitzmann et al. |
| 2004/0097995 A1 | 5/2004 | Nash et al. |
| 2004/0102772 A1 | 5/2004 | Baxter et al. |
| 2004/0147934 A1 | 7/2004 | Kiester |
| 2004/0167553 A1 | 8/2004 | Simpson et al. |
| 2004/0167554 A1 | 8/2004 | Simpson et al. |
| 2004/0181249 A1 | 9/2004 | Torrance et al. |
| 2004/0199051 A1 | 10/2004 | Weisel |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0235611 A1 | 11/2004 | Nistal |
| 2004/0236312 A1 | 11/2004 | Nistal et al. |
| 2004/0243162 A1 | 12/2004 | Wulfman et al. |
| 2005/0004585 A1 | 1/2005 | Hall et al. |
| 2005/0020974 A1 | 1/2005 | Noriega et al. |
| 2005/0059990 A1 | 3/2005 | Ayala et al. |
| 2005/0113853 A1 | 5/2005 | Noriega et al. |
| 2005/0149084 A1 | 7/2005 | Kanz et al. |
| 2005/0177068 A1 | 8/2005 | Simpson |
| 2005/0197661 A1 | 9/2005 | Carrison et al. |
| 2005/0222519 A1 | 10/2005 | Simpson |
| 2005/0240146 A1 | 10/2005 | Nash et al. |
| 2006/0020327 A1 | 1/2006 | Lashinski et al. |
| 2006/0074442 A1 | 4/2006 | Noriega et al. |
| 2006/0229646 A1 | 10/2006 | Sparks |
| 2006/0239982 A1 | 10/2006 | Simpson |
| 2006/0241564 A1 | 10/2006 | Corcoran et al. |
| 2007/0135733 A1 | 6/2007 | Soukup et al. |
| 2007/0225739 A1 | 9/2007 | Pintor et al. |
| 2007/0250000 A1 | 10/2007 | Magnin et al. |
| 2007/0282303 A1 | 12/2007 | Nash et al. |
| 2007/0282350 A1 | 12/2007 | Hernest |
| 2007/0282358 A1 | 12/2007 | Remiszewski et al. |
| 2008/0004643 A1 | 1/2008 | To et al. |
| 2008/0004645 A1 | 1/2008 | To et al. |
| 2008/0045986 A1 | 2/2008 | To et al. |
| 2008/0103516 A1 | 5/2008 | Wulfman et al. |
| 2008/0140101 A1 | 6/2008 | Carley et al. |
| 2008/0249364 A1 | 10/2008 | Korner |
| 2009/0018565 A1* | 1/2009 | To et al. .................. 606/159 |
| 2009/0018566 A1 | 1/2009 | Escudero et al. |
| 2009/0018567 A1 | 1/2009 | Escudero et al. |
| 2009/0024085 A1 | 1/2009 | To et al. |
| 2010/0174302 A1 | 7/2010 | Heitzmann et al. |
| 2010/0324567 A1 | 12/2010 | Root et al. |
| 2010/0324576 A1 | 12/2010 | Pintor et al. |
| 2011/0040315 A1 | 2/2011 | To et al. |
| 2011/0112563 A1 | 5/2011 | To et al. |
| 2011/0152906 A1 | 6/2011 | Escudero et al. |
| 2011/0152907 A1 | 6/2011 | Escudero et al. |
| 2011/0270289 A1 | 11/2011 | To et al. |
| 2011/0301626 A1 | 12/2011 | To et al. |
| 2013/0085515 A1 | 4/2013 | To et al. |
| 2013/0090674 A1 | 4/2013 | Escudero et al. |
| 2013/0096587 A1 | 4/2013 | Smith et al. |
| 2013/0103062 A1 | 4/2013 | To et al. |
| 2013/0103063 A1 | 4/2013 | Escudero et al. |
| 2013/0158578 A1 | 6/2013 | Ghodke et al. |
| 2013/0296901 A1 | 11/2013 | Olson |
| 2014/0039532 A1 | 2/2014 | Vrba |

FOREIGN PATENT DOCUMENTS

| | | |
|---|---|---|
| EP | 0 817 595 B1 | 6/2002 |
| EP | 1 176 915 B1 | 10/2005 |
| EP | 1 158 910 B1 | 10/2007 |
| EP | 1 315 460 B1 | 12/2007 |
| EP | 1 722 694 B1 | 5/2009 |
| EP | 1 870 044 B1 | 7/2009 |
| EP | 2 641 551 A1 | 9/2013 |
| JP | 1-131653 A | 5/1989 |
| JP | 08-509639 A | 10/1996 |
| JP | 09-508554 A | 9/1997 |
| JP | 11-506358 A | 6/1999 |
| JP | 2001-522631 A | 11/2001 |
| JP | 2002-538876 A | 11/2002 |
| JP | 2004-503265 A | 2/2004 |
| JP | 2004-514463 A | 5/2004 |
| JP | 2006-511256 A | 4/2006 |
| WO | WO-94/24946 A1 | 11/1994 |
| WO | WO-95/21576 A1 | 8/1995 |
| WO | WO-96/29941 A1 | 10/1996 |
| WO | WO-96/29942 A1 | 10/1996 |
| WO | WO-99/23958 A1 | 5/1999 |
| WO | WO-99/35977 A1 | 7/1999 |
| WO | WO-00/54659 A1 | 9/2000 |
| WO | WO-01/74255 A1 | 10/2001 |
| WO | WO-01/76680 A1 | 10/2001 |
| WO | WO-2005/084562 A2 | 9/2005 |
| WO | WO-2005/084562 A3 | 9/2005 |
| WO | WO-2005/123169 A1 | 12/2005 |
| WO | WO-2007/010389 A1 | 1/2007 |
| WO | WO-2008/005888 A2 | 1/2008 |
| WO | WO-2008/005888 A3 | 1/2008 |
| WO | WO-2008/005891 A2 | 1/2008 |
| WO | WO-2008/005891 A3 | 1/2008 |
| WO | WO-2009/005779 A1 | 1/2009 |
| WO | WO-2009/054968 A1 | 4/2009 |
| WO | WO-2009/126309 A2 | 10/2009 |
| WO | WO-2009/126309 A3 | 10/2009 |
| WO | WO-2013/056262 A1 | 4/2013 |
| WO | WO-2013/172970 A1 | 11/2013 |

OTHER PUBLICATIONS

Final Office Action mailed on Feb. 12, 2014 for U.S. Appl. No. 12/930,077, filed Dec. 27, 2010, 9 pages.

Ex-Parte Quayle Action mailed on Mar. 30, 2012, for U.S. Appl. No. 11/567,715, filed Dec. 6, 2006, 6 pages.

Ex-Parte Quayle Action mailed on Mar. 30, 2012, for U.S. Appl. No. 12/215,721, filed Jun. 30, 2008, 6 pages.

Final Office Action mailed on Feb. 3, 2010, for U.S. Appl. No. 11/551,193, filed Oct. 19, 2006, 8 pages.

(56) References Cited

OTHER PUBLICATIONS

Final Office Action mailed on May 25, 2010, for U.S. Appl. No. 11/551,191, filed Oct. 19, 2006, 11 pages.
Final Office Action mailed on Mar. 11, 2011, for U.S. Appl. No. 11/771,865, filed Jun. 29, 2007, 8 pages.
Final Office Action mailed on Apr. 15, 2011, for U.S. Appl. No. 12/215,854, filed Jun. 30, 2008, 8 pages.
Final Office Action mailed on Apr. 20, 2011, for U.S. Appl. No. 12/215,855, filed Jun. 30, 2008, 8 pages.
Final Office Action mailed on Jul. 13, 2011, for U.S. Appl. No. 12/215,752, filed Jun. 30, 2008, 7 pages.
Final Office Action mailed on Dec. 22, 2011, for U.S. Appl. No. 11/567,715, filed Dec. 6, 2006, 6 pages.
Final Office Action mailed on Dec. 22, 2011, for U.S. Appl. No. 12/215,721, filed Jun. 30, 2008, 6 pages.
Final Office Action mailed on Mar. 22, 2012, for U.S. Appl. No. 11/551,191, filed Oct. 19, 2006, 5 pages.
Final Office Action mailed on Nov. 6, 2012, for U.S. Appl. No. 12/930,077, filed Dec. 27, 2010, 6 pages.
Final Office Action mailed on Jan. 24, 2013, for U.S. Appl. No. 12/925,466, filed Oct. 22, 2010, 8 pages.
Final Office Action mailed on Feb. 6, 2013, for U.S. Appl. No. 13/182,844, filed Jul. 14, 2011, 10 pages.
Final Office Action mailed on Apr. 24, 2013 for U.S. Appl. No. 12/932,370, filed Feb. 24, 2011, 10 pages.
Final Office Action mailed on May 6, 2013 for U.S. Appl. No. 12/215,855, filed Jun. 30, 2008, 8 pages.
Final Office Action mailed on Jun. 13, 2013 for U.S. Appl. No. 12/215,752, filed Jun. 30, 2008, 9 pages.
Final Office Action mailed on Aug. 30, 2013 for U.S. Appl. No. 12/932,371, filed Feb. 24, 2011, 9 pages.
Final Office Action mailed on Oct. 24, 2013 for U.S. Appl. No. 12/215,854, filed Jun. 30, 2008, 8 pages.
Final Office Action mailed on Dec. 5, 2013 for U.S. Appl. No. 13/715,870, filed Dec. 14, 2012, 6 pages.
Ikeno, F. et al. (2004). "Initial Experience with the Novel 6 Fr-Compatible System for Debulking De Novo Coronary Arterial Lesions," *Catheterization and Cardiovascular Interventions* 62:308-317.
International Preliminary Report on Patentability issued on Jan. 6, 2009, for PCT Patent Application No. PCT/US2007/072570, filed on Jun. 29, 2007, 4 pages.
International Preliminary Report on Patentability issued Jan. 6, 2009, for PCT Patent Application No. PCT/US2007/072574, filed on Jun. 29, 2007, 4 pages.
International Preliminary Report on Patentability issued on Jun. 30, 2010, for PCT Patent Application No. PCT/US2008/012012, filed on Oct. 22, 2008, 11 pages.
International Preliminary Report on Patentability issued on Aug. 6, 2010, for PCT Patent Application No. PCT/US09/02253, filed on Apr. 10, 2009, 12 pages.
International Search Report mailed on Sep. 3, 2008, for PCT Patent Application No. PCT/US07/72570, filed on Jun. 29, 2007, 1 page.
International Search Report mailed on Sep. 18, 2008, for PCT Patent Application No. PCT/US2007/072574, filed on Jun. 29, 2007, 1 page.
International Search Report mailed on Oct. 29, 2008, for PCT Patent Application No. PCT/US08/08140, filed on Jun. 30, 2008, 1 page.
International Search Report mailed on Feb. 12, 2009, for PCT Patent Application No. PCT/US08/12012, filed on Oct. 22, 2008, 1 page.
International Search Report mailed on Aug. 12, 2009, for PCT Patent Application No. PCT/US09/02253, filed on Apr. 10, 2009, 1 page.
International Search Report mailed on Mar. 12, 2013, for PCT Patent Application No. PCT/US12/60316, filed on Oct. 15, 2012, 5 pages.
Kanjwal, M.K. et al. (2004). "Peripheral Arterial Disease—The Silent Killer," *JK—Practitioner* 11(4):225-232.
Nakamura, M. et al. (2002). "Efficacy and Feasibility of Helixcision for Debulking Neointimal Hyperplasia for In-Stent Restenosis," *Catheterization and Cardiovascular Interventions* 57:460-466.

Non-Final Office Action mailed on Apr. 3, 2009, for U.S. Appl. No. 11/551,193, filed Oct. 19, 2006, 7 pages.
Non-Final Office Action mailed on May 27, 2009, for U.S. Appl. No. 11/567,715, filed Dec. 6, 2006, 16 pages.
Non-Final Office Action mailed on Jul. 15, 2009, for U.S. Appl. No. 11/551,191, filed Oct. 19, 2006, 18 pages.
Non-Final Office Action mailed on Jun. 25, 2010, for U.S. Appl. No. 11/551,198, filed Oct. 19, 2006, 15 pages.
Non Final Office Action mailed on Jun. 25, 2010, for U.S. Appl. No. 11/771,865, filed Jun. 29, 2007, 10 pages.
Non-Final Office Action mailed on Aug. 27, 2010, for U.S. Appl. No. 11/551,203, filed Oct. 19, 2006, 19 pages.
Non-Final Office Action mailed on Oct. 5, 2010, for U.S. Appl. No. 12/215,855, filed Jun. 30, 2008, 10 pages.
Non-Final Office action mailed on Oct. 5, 2010, for U.S. Appl. No. 12/215,752, filed Jun. 30, 2008, 8 pages.
Non-Final Office Action mailed on Oct. 12, 2010, for U.S. Appl. No. 12/215,854, filed Jun. 30, 2008, 11 pages.
Non-Final Office Action mailed on Apr. 14, 2011, for U.S. Appl. No. 12/215,721, filed Jun. 30. 2008, 9 pages.
Non-Final Office Action mailed on Aug. 4, 2011, for U.S. Appl. No. 11/551,191, filed Oct. 19, 2006, 6 pages.
Non-Final Office Action mailed on Aug. 4, 2011, for U.S. Appl. No. 11/567,715, filed Dec. 6, 2006, 9 pages.
Non-Final Office Action mailed on Apr. 27, 2012, for U.S. Appl. No. 12/925,466, filed Oct. 22, 2010, 7 pages.
Non-Final Office Action mailed on May 17, 2012, for U.S. Appl. No. 13/182,844, filed Jul. 14, 2011, 12 pages.
Non-Final Office Action mailed on Jun. 20, 2012, for U.S. Appl. No. 13/213,896, filed Aug. 19, 2011, 6 pages.
Non-Final Office Action mailed on Nov. 29, 2012, for U.S. Appl. No. 12/215,752, filed Jun. 30, 2008, 7 pages.
Non-Final Office Action mailed on Dec. 11, 2012, for U.S. Appl. No. 11/771,865, filed Jun. 29, 2007, 7 pages.
Non-Final Office Action mailed on Dec. 14, 2012, for U.S. Appl. No. 12/932,370, filed Feb. 24, 2011, 7 pages.
Non-Final Office Action mailed on Jan. 8, 2013, for U.S. Appl. No. 12/932,371, filed Feb. 24, 2011, 7 pages.
Non-Final Office Action mailed on Jan. 16, 2013, for U.S. Appl. No. 12/215,854, filed Jun. 30, 2008, 7 pages.
Non-Final Office Action mailed on Mar. 6, 2013, for U.S. Appl. No. 13/715,870, filed Dec. 14, 2012, 9 pages.
Non-Final Office Action mailed on Apr. 26, 2013, for U.S. Appl. No. 13/691,485, filed Nov. 30, 2012, 7 pages.
Non-Final Office Action mailed on May 17, 2013 for U.S. Appl. No. 12/930,077, filed Dec. 27, 2010, 8 pages.
Non-Final Office Action mailed on Jun. 24, 2013 for U.S. Appl. No. 13/715,664, filed Dec. 14, 2012, 9 pages.
Non-Final Office Action mailed on Nov. 25, 2013 for U.S. Appl. No. 12/932,370, filed Feb. 24, 2011, 10 pages.
Non-Final Office Action mailed on Nov. 27, 2013 for U.S. Appl. No. 12/215,855, filed Jun. 30, 2008, 7 pages.
Notice of Allowance mailed on Feb. 19, 2010, for U.S. Appl. No. 11/567,715, filed Dec. 6, 2006, 6 pages.
Notice of Allowance mailed on Jun. 18, 2010 for U.S. Appl. No. 11/567,715, filed Dec. 6, 2006, 6 pages.
Notice of Allowance mailed on Nov. 29, 2010, for U.S. Appl. No. 11/567,715, filed Dec. 6, 2006, 6 pages.
Notice of Allowance mailed on Dec. 10, 2010, for U.S. Appl. No. 11/551,193, filed Oct. 19, 2006, 7 pages.
Notice of Allowance mailed on Mar. 3, 2011, for U.S. Appl. No. 11/551,193, filed Oct. 19, 2006, 7 pages.
Notice of Allowance mailed on Jun. 3, 2011, for U.S. Appl. No. 11/551,203, filed Oct. 19, 2006, 10 pages.
Notice of Allowance mailed on Oct. 4, 2011, for U.S. Appl. No. 12/288,593, filed Oct. 22, 2008, 9 pages.
Notice of Allowance mailed on Dec. 13, 2011, for U.S. Appl. No. 12/384,970, filed Apr. 10, 2009, 11 pages.
Notice of Allowance mailed on Aug. 6, 2012, for U.S. Appl. No. 12/215,721, filed Jun. 30, 2008, 8 pages.
Notice of Allowance mailed on Aug. 22, 2012, for U.S. Appl. No. 13/309,986, filed Dec. 2, 2011, 10 pages.

(56) References Cited

OTHER PUBLICATIONS

Notice of Allowance mailed on Sep. 18, 2012, for U.S. Appl. No. 11/567,715, filed Dec. 6, 2006, 8 pages.
Notice of Allowance mailed on Feb. 6, 2013, for U.S. Appl. No. 13/213,896, filed Aug. 19, 2011, 8 pages.
Notice of Allowance mailed on May 15, 2013, for U.S. Appl. No. 11/551,191, filed Oct. 19, 2006, 10 pages.
Notice of Allowance mailed on Jun. 18, 2013, for U.S. Appl. No. 11/551,191, filed Oct. 19, 2006, 5 pages.
Notice of Allowance mailed on Jun. 21, 2013, for U.S. Appl. No. 12/215,721, filed Jun. 30, 2008, 10 pages.
Notice of Allowance mailed on Jul. 1, 2013, for U.S. Appl. No. 13/213,896, filed Aug. 19, 2011, 10 pages.
Notice of Allowance mailed on Sep. 5, 2013, for U.S. Appl. No. 11/551,191, filed Oct. 19, 2006, 10 pages.
Notice of Allowance mailed on Oct. 7, 2013, for U.S. Appl. No. 12/215,721, filed Jun. 30, 2008, 11 pages.
Notice of Allowance mailed Nov. 4, 2013, for U.S. Appl. No. 13/691,485, filed Nov. 30, 2012, 10 pages.
Supplementary European Search Report mailed on Jun. 20, 2011, for EP Patent Application No. 08779894.8, filed on Jun. 30, 2008, 7 pages.
Supplementary European Search Report mailed on Jun. 26, 2013, for EP Patent Application No. 08841648.2, filed on May 21, 2010, 5 pages.
Supplementary European Search Report mailed Aug. 21, 2013, for EP Patent Application No. 09730501.5, filed on Nov. 4, 2010, 5 pages.
Non-Final Office Action mailed on Apr. 8, 2014 for U.S. Appl. No. 14/106,651, filed Dec. 13, 2013, 6 pages.
Non-Final Office Action mailed on Apr. 9, 2014 for U.S. Appl. No. 12/925,466, filed Oct. 22, 2010, 5 pages.
Notice of Allowance mailed on Mar. 24, 2014 for U.S. Appl. No. 11/551,191, filed Oct. 19, 2006, 9 pages.
Notice of Allowance mailed on Apr. 15, 2014 for U.S. Appl. No. 13/213,896, filed Aug. 19, 2011, 8 pages.

* cited by examiner

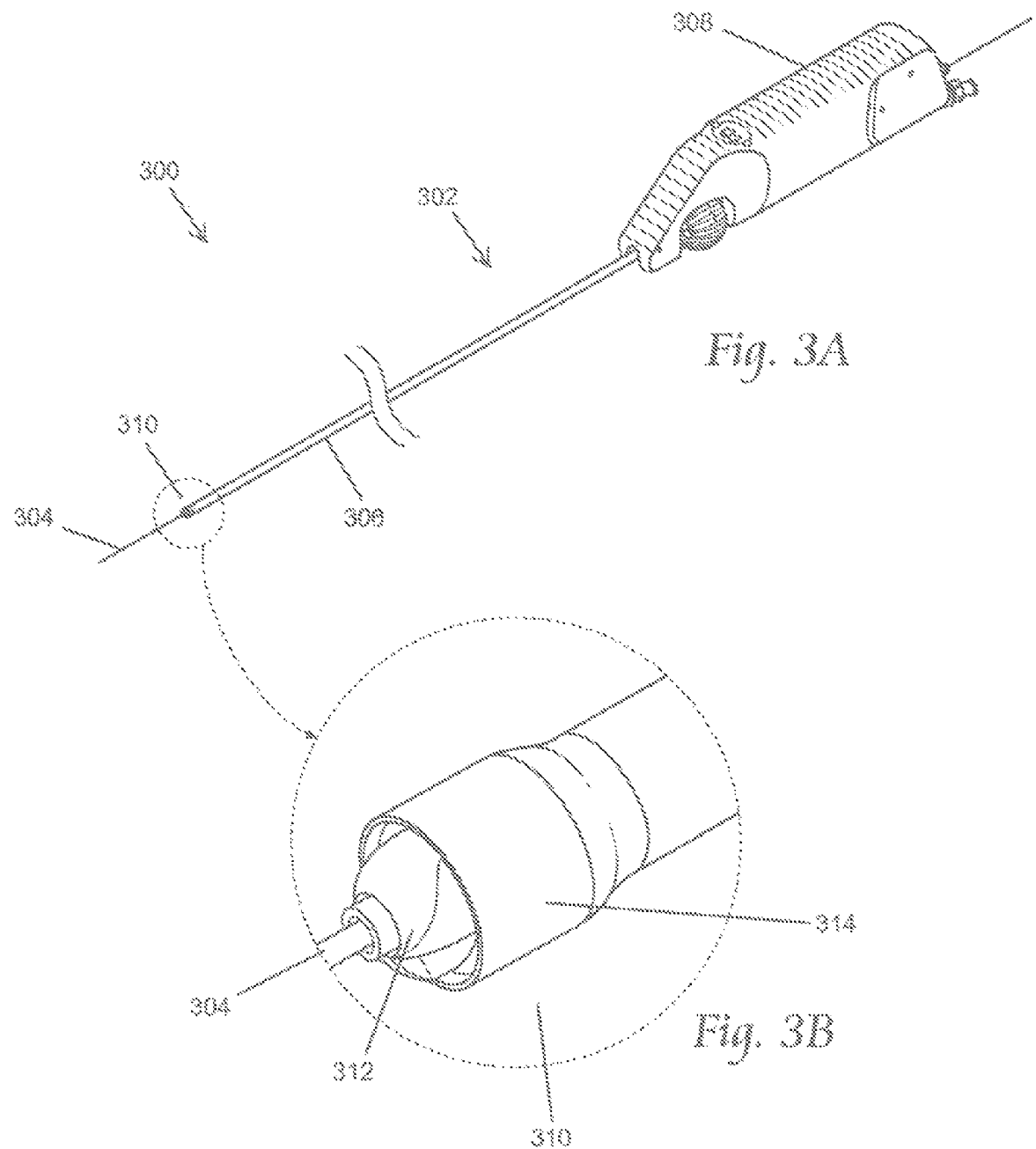

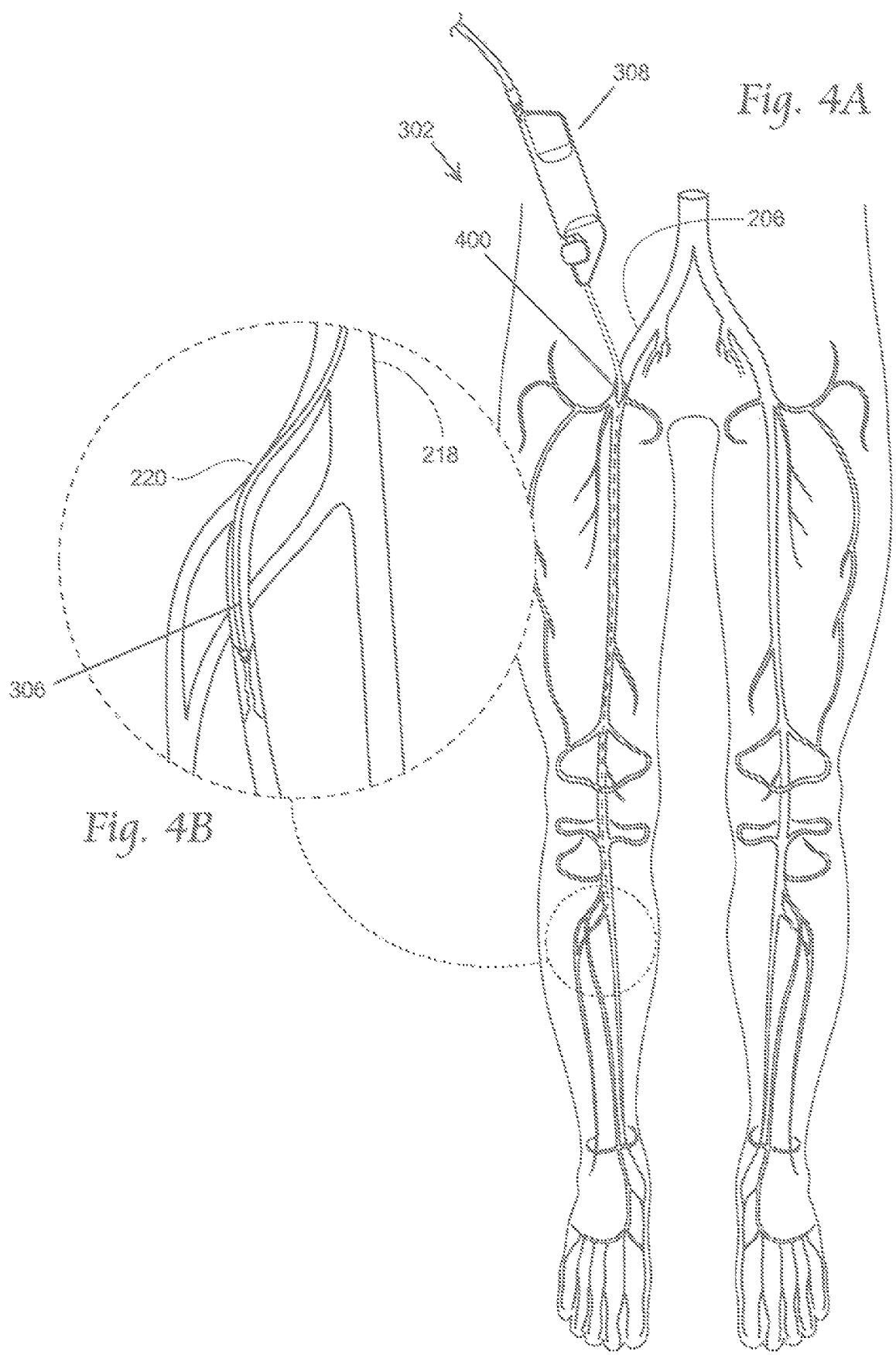

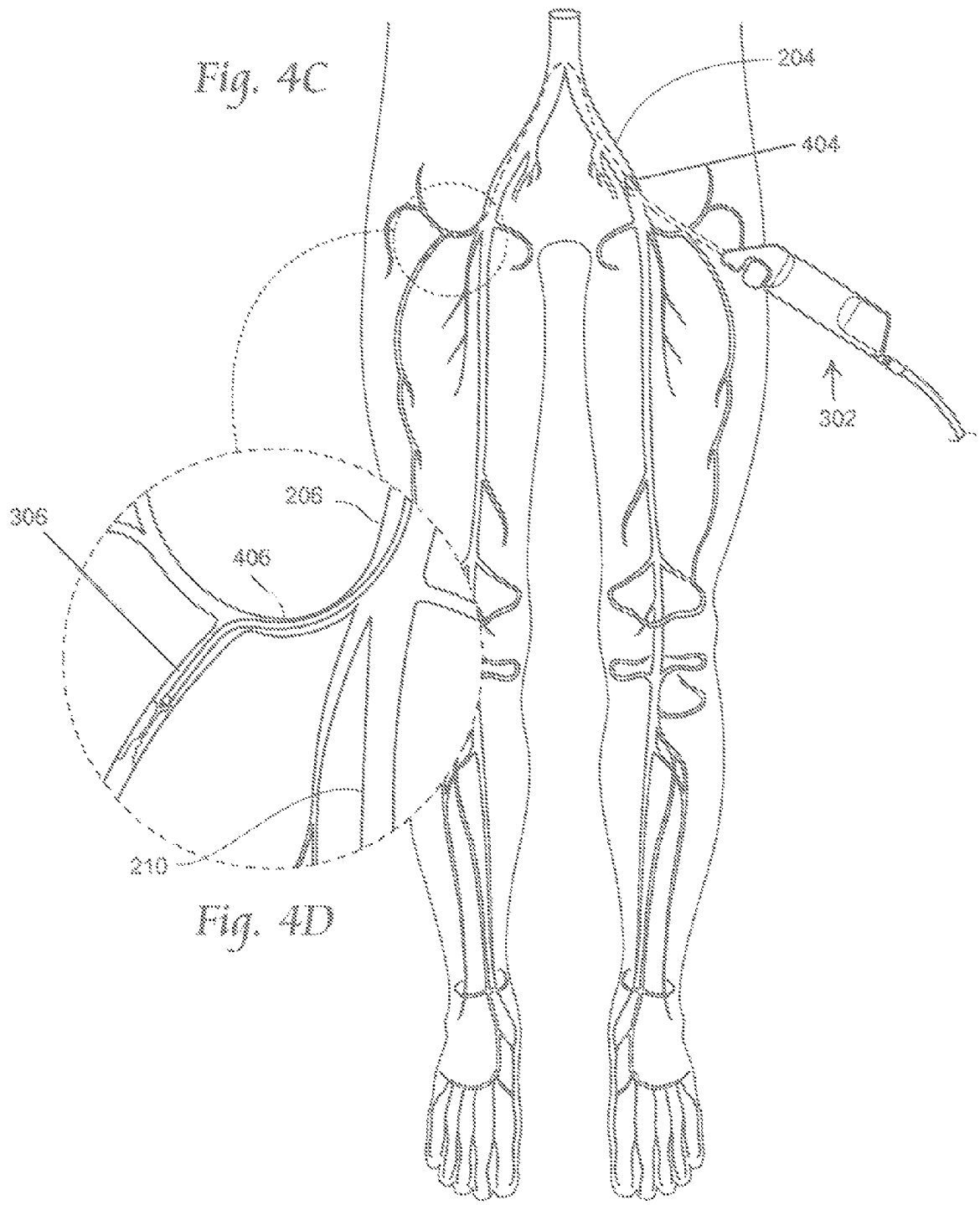

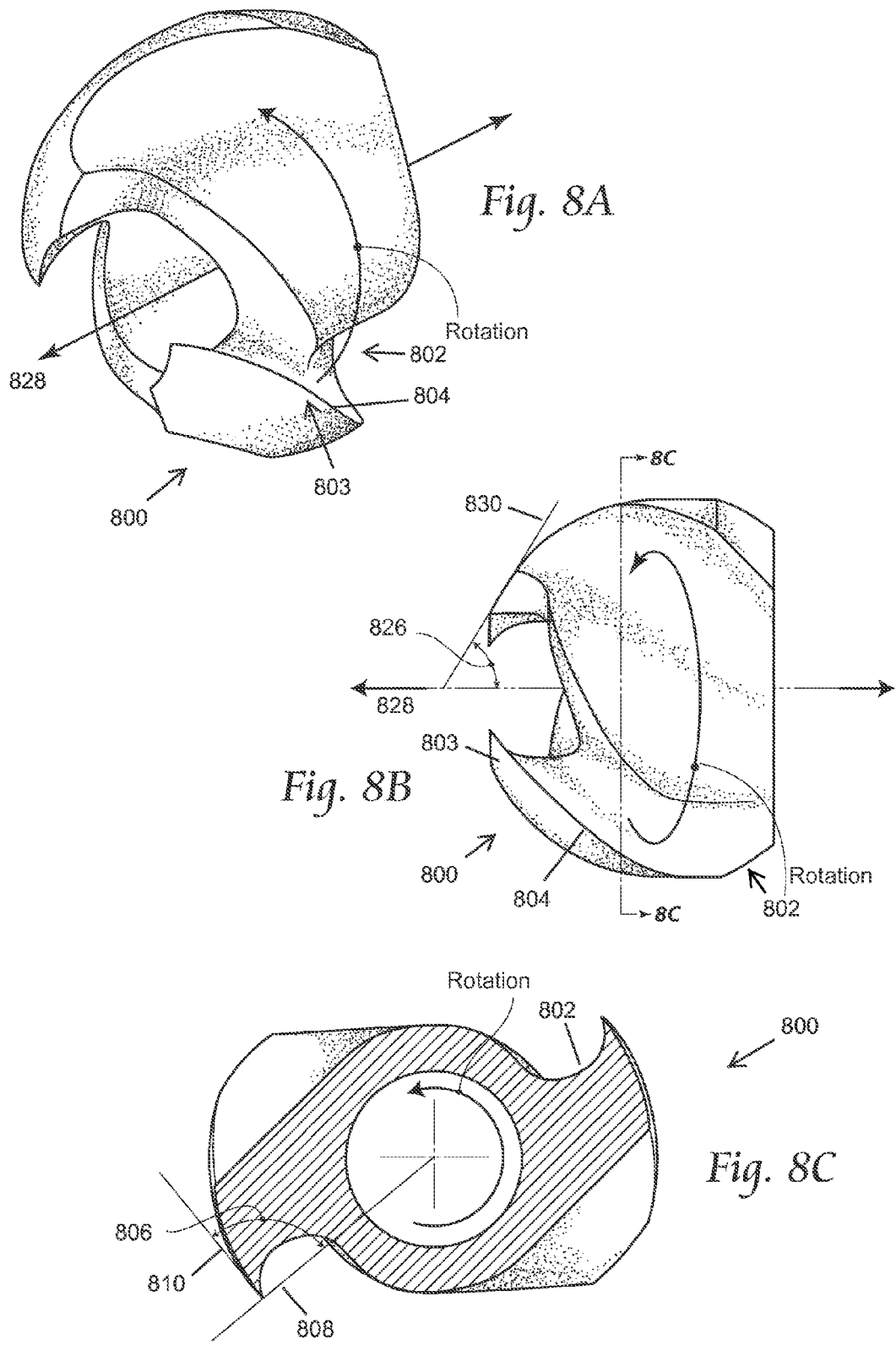

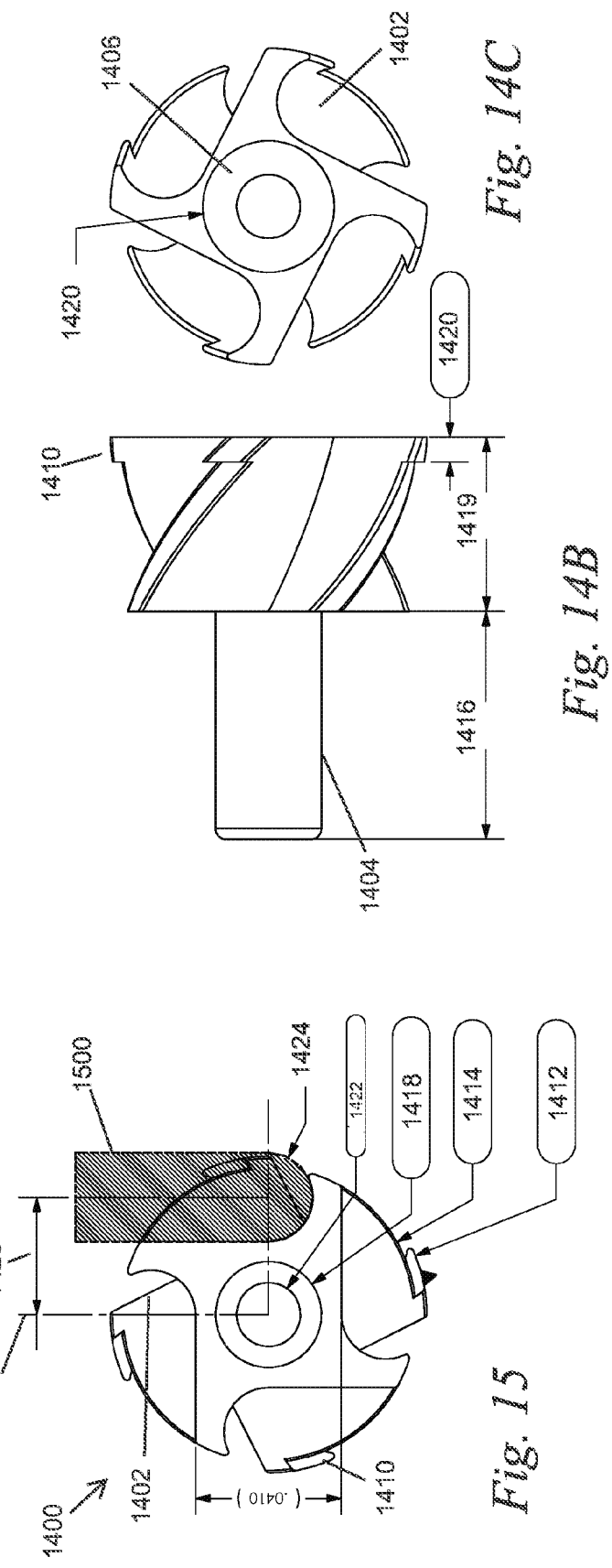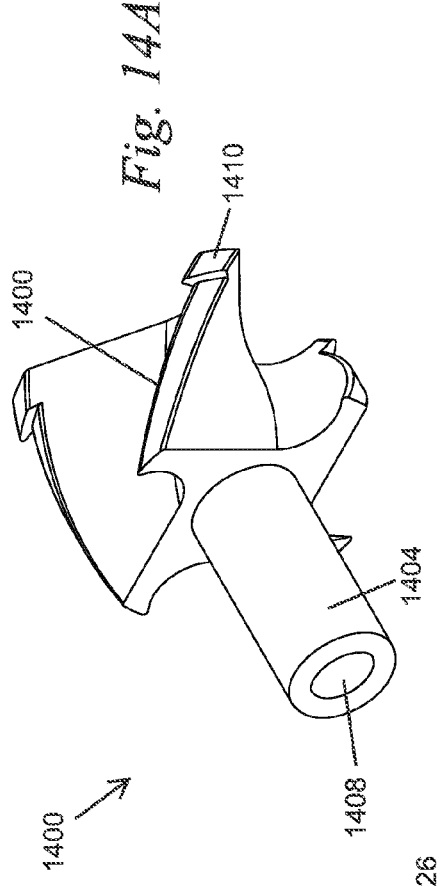

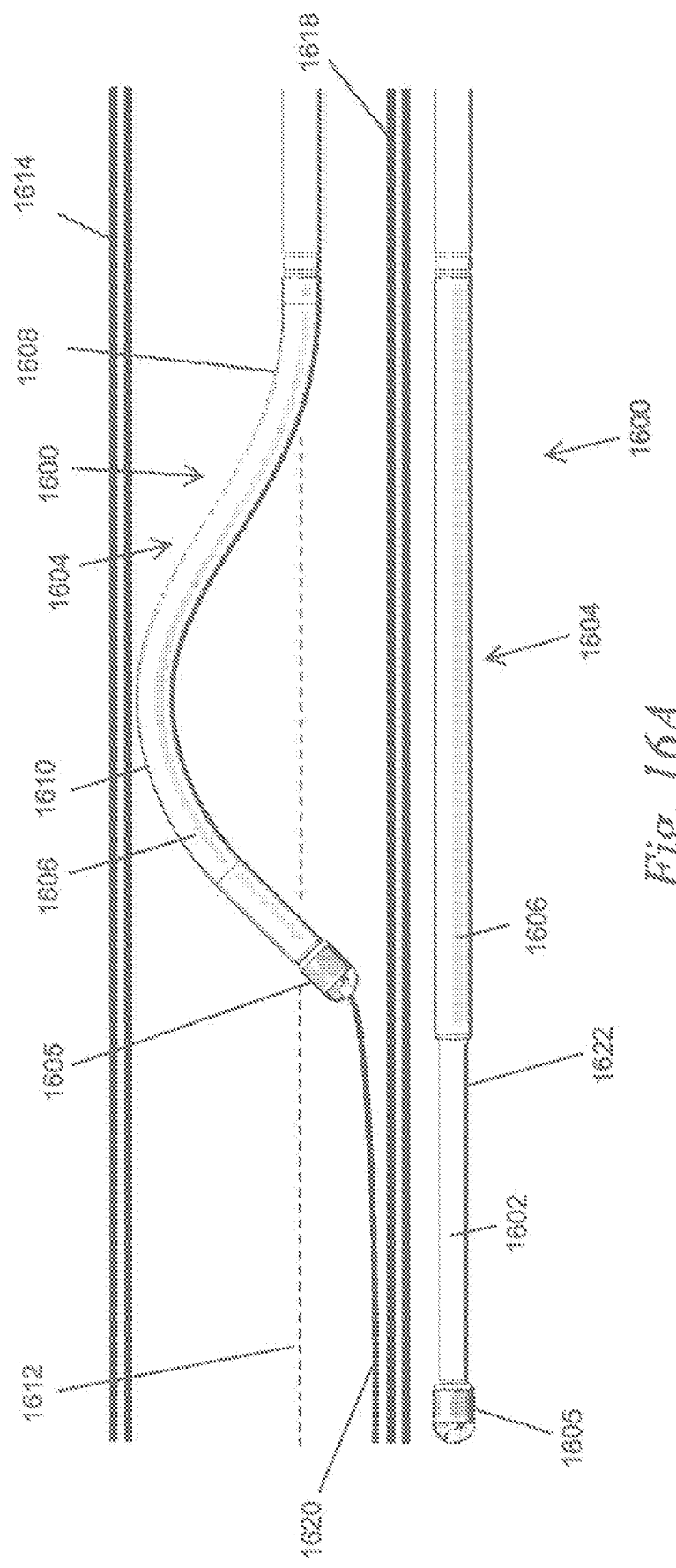

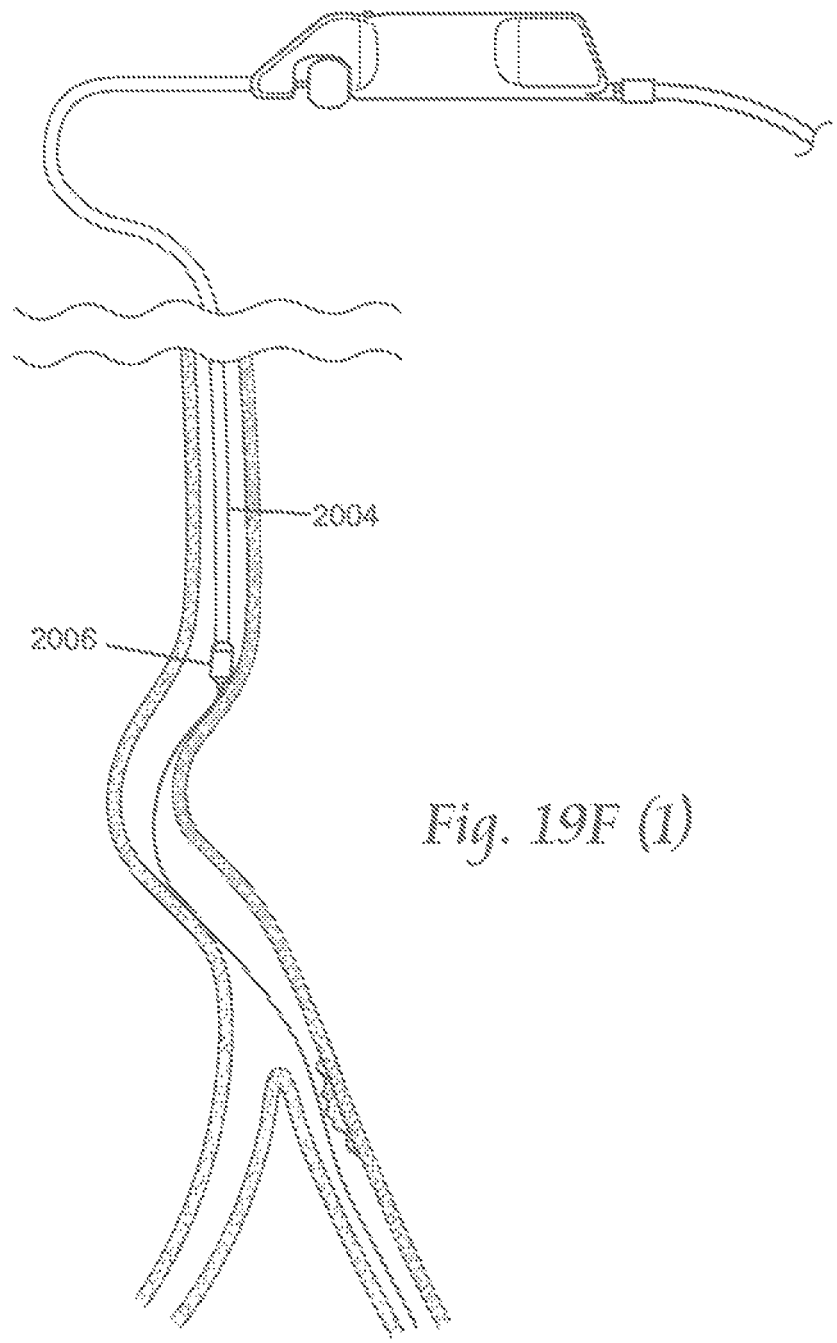
Fig. 19F (1)

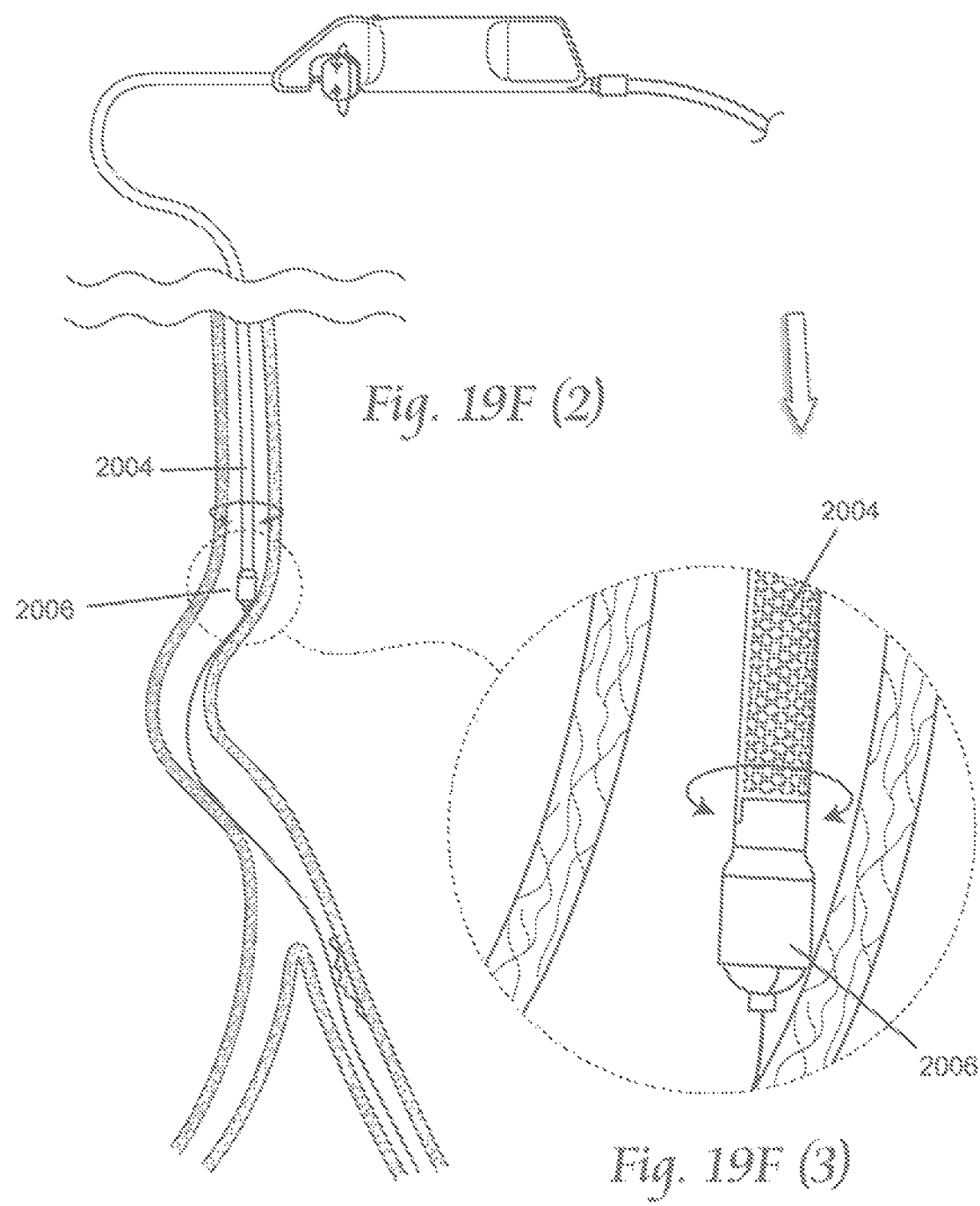
Fig. 19F (2)
Fig. 19F (3)

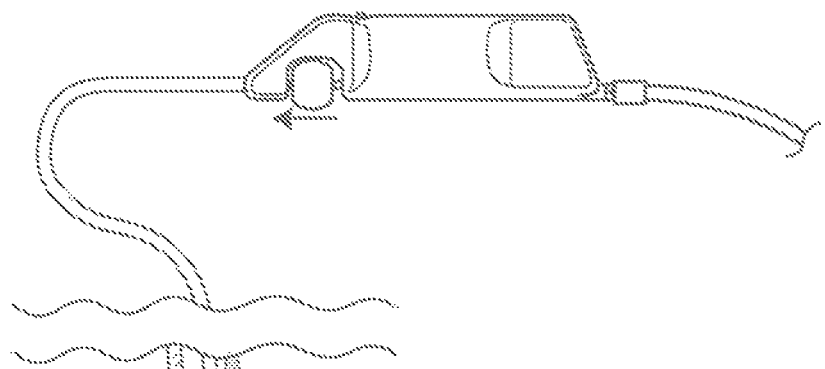
Fig. 19F (4)
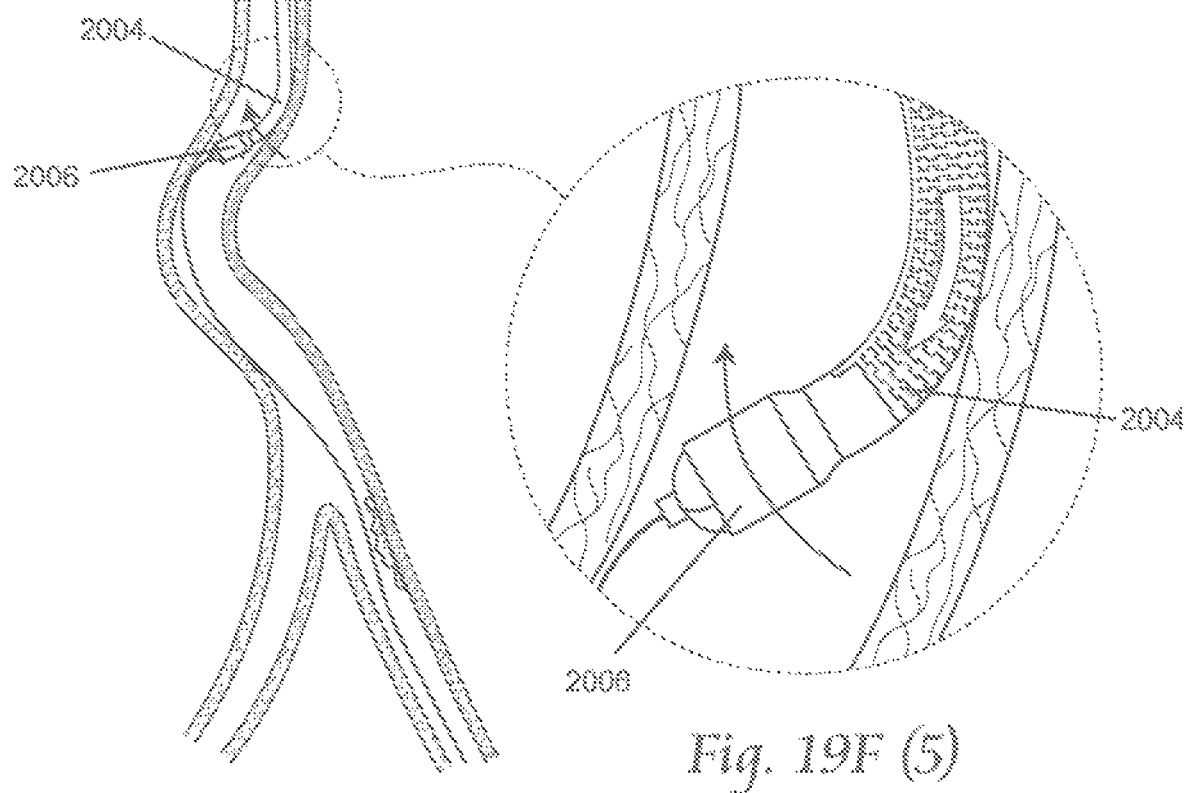
Fig. 19F (5)

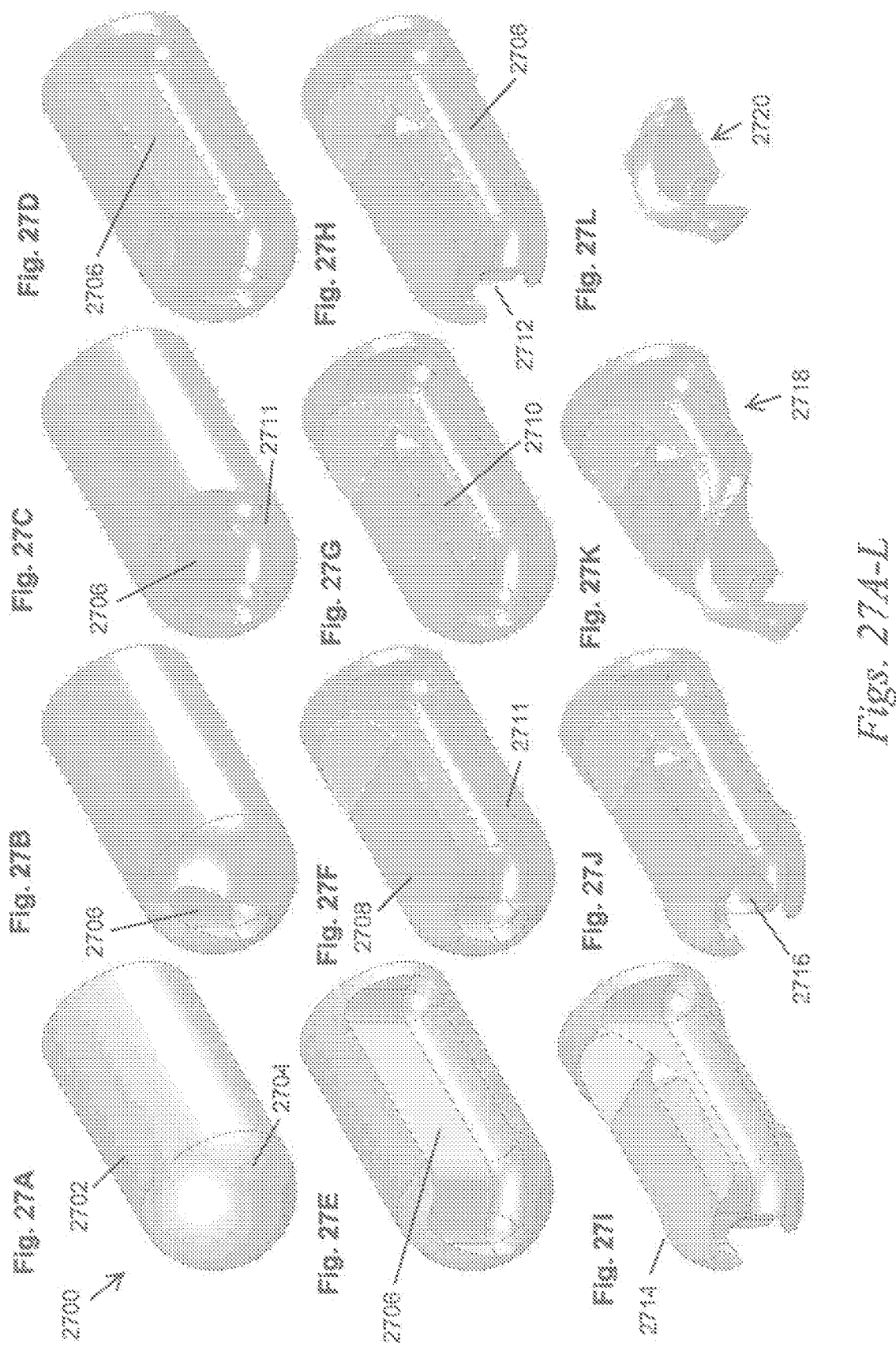
Figs. 27A-L

ATHERECTOMY APPARATUS, SYSTEMS AND METHODS

CROSS-REFERENCE TO RELATED APPLICATIONS

This application is a continuation of U.S. patent application Ser. No. 13/652,352, filed on Oct. 15, 2012 and titled "ATHERECOTMY APPARATUS, SYSTEMS, AND METHODS", which claims priority to U.S. Provisional Application Ser. No. 61/546,888, filed on Oct. 13, 2011 and titled "ATHERECTOMY APPARATUS, SYSTEMS, AND METHODS", the content of each of which is hereby incorporated in its entirety.

FIELD

The devices and methods described herein generally relate to treatment of occluded body lumens, such as the removal of occlusive material from a blood vessel or other body parts.

BACKGROUND

Peripheral and interventional cardiology is a medical specialty that deals with treatment of various forms of cardiovascular disease, including coronary artery disease and peripheral vascular disease. Coronary artery disease and peripheral vascular disease can arise due to the narrowing of the arteries by atherosclerosis (also called arteriosclerosis). Coronary artery disease generally affects arteries of the heart—arteries that carry blood to cardiac muscles and surrounding tissue. Peripheral vascular disease refers to various diseases of the vascular system outside the heart and brain, which carries blood, for example, to the legs.

Atherosclerosis commonly affects the medium and large arteries, and may occur when fat, cholesterol, and other substances build up on the walls of arteries and form fleshy or hard/calcified structures called plaques/lesions. FIG. 1 shows an instance of a first normal arterial segment (100) having a native arterial wall (102), a second arterial segment (104) with mild atherosclerosis and initial plaque (106) formation on the native arterial wall (108), and a third arterial segment (110) with severe atherosclerosis and having advanced plaque (112) formation on the native arterial wall (114). As plaque forms within the native arterial wall, the artery may narrow and become less flexible, which may make it more difficult for blood to flow therethrough. In the peripheral arteries, the plaque is typically not localized, but can extend in length along the axis of the artery for as much as 10 mm or more (in some instance up to 400 mm or more).

Pieces of plaque can break off and move through the affected artery to smaller blood vessels, which may in some instances block them and may result in tissue damage or tissue death (embolization). In some cases, the atherosclerotic plaque may be associated with a weakening of the wall of the affected artery, which can lead to an aneurysm. Minimally invasive surgeries may be performed to remove plaque from arteries in an effort to alleviate or help prevent the complications of atherosclerosis.

A number of interventional surgical methodologies may be used to treat atherosclerosis. In balloon angioplasty, for example, a physician may advance a collapsed, intravascular balloon catheter into a narrowed artery, and may inflate the balloon to macerate and/or displace plaque against the vessel wall. A successful angioplasty may help reopen the artery and allow for improved blood flow. Often, balloon angioplasty is performed in conjunction with the placement of a stent or scaffold structure within the artery to help minimize re-narrowing of the artery. Balloon angioplasty, however, can stretch the artery and induce scar tissue formation, while the placement of a stent can cut arterial tissue and also induce scar tissue formation. Scar tissue formation may lead to restenosis of the artery. In some instances, balloon angioplasty can also rip the vessel wall.

Atherectomy is another treatment methodology for atherosclerosis, and involves the use of an intravascular device to mechanically remove (e.g., debulk) plaque from the wall of the artery. Atherectomy devices may allow for the removal of plaque from the wall of an artery, reducing the risk of stretching, cutting, or dissecting the arterial wall and causing tissue damage that leads to restenosis. In some instances, atherectomy may be used to treat restenosis by removing scar tissue Current atherectomy treatments suffer from structural and performance limitations. For example, currently-available atherectomy devices with rotating burrs (e.g., the Diamondback 360® PAD System, from Cardiovascular Systems, Inc.) generally are not configured to capture particles that are released as the burr grinds/sands tissue, which may result in diminished downstream blood flow resulting from particle residue. Additionally, these rotating burrs may cause hemolysis, and are generally limited as an adjunct therapy to angioplasty.

Other systems, such as the JETSTREAM G3® System, from Pathway Medical Technologies, include expandable cutters with foldable/movable cutting wings and vacuum-driven aspiration supplied via a vacuum pump, which may cause the artery to collapse on to the cutter and perforate the arterial wall. Other atherectomy systems may include a side-window eccentric cutter and distal nosecone which receives material from the cutter. Because the nosecone can only hold a limited volume of plaque, a surgeon may need to repeatedly withdraw the cutter and flush plaque and other material from the nosecone.

It is be desirable to provide improved atherectomy devices and methods.

BRIEF SUMMARY

Described here are devices and methods for removing occlusive material from one or more vessels. Generally, the devices may comprise a handle, a cutter assembly, and at least one catheter connecting the handle and the cutter assembly. In some variations, the cutter assembly may comprise a cutter housing having an opening and a cutter. In some variations, the cutter may comprise at least one helical flute each forming a cutting blade. In some of these variations, the one or more of the cutting blades may have a positive rake angle. In some of these variations, the positive rake angle may be at least 20 degrees. In some of these variations, the rake angle may be at least about 40 degrees. In some of these variations, the positive rake angle may be between 60 degrees and 80 degrees. In some variations, at one or more of the cutting blades may have a negative angle. In some of these variations, a cutter assembly may comprise a plurality of cutting flutes, wherein at least one of the cutting flutes forms a cutting blade having a positive rake angle, and wherein at least one of the cutting flutes forms a cutting blade having a negative rake angle. In some variations one or more of the cutting blades may have a relief angle less than or equal to 10 degrees. In some of these variations, one or more of the cutting blades may have a relief angle of about 0 degrees. In some variations, one or more of the cutting blades has a flute angle less than or equal to about 30 degrees.

In some variations, the cutter may comprise a first cutting element and a second cutting element. In some of these variations, at least a portion of the first cutting element may extend from an opening in the cutter housing. In some of these variations, at least a portion of the cutting element may have an outer diameter greater than or equal to an outer diameter of the cutter housing.

In some variations, the at least one catheter may comprise one or more regions of cut patterns. In some variations, at least one of the regions may comprise a helical cut pattern. In some variations, at least one of the regions may comprise a brickwork cut pattern. The devices may further comprise a torque shaft configured to rotate the cutter relative to the at least one catheter. In some variations, the device may further comprise an internal conveyor member.

In some variations, the at least one catheter may be configured to be deflected. In some of these variations, a device may comprise a handle, a first catheter having a proximal portion and a distal portion, a second catheter having a proximal portion and a distal portion, the second catheter moveable between an undeflected configuration and a deflected configuration in which the distal portion of the second catheter comprises a first curve and a second curve, and a cutter assembly attached to the first catheter, wherein the distal portion of the second catheter is stiffer than the distal portion of the first catheter, and wherein the proximal portion of the first catheter is stiffer than the distal portion of the second catheter, and wherein the first catheter is moveable relative to the second catheter to change the second catheter between the undeflected and deflected configurations. The devices described here may be used to remove occlusive materials from one or more vessels. In some variations, the device may be advanced intravascularly to a target zone, and the cutter assembly may be activated to cut occlusive material. In some variations, the occlusive material may comprise a chronic total occlusion. In other variations, the occlusive may be removed from the interior of a stent.

BRIEF DESCRIPTION OF THE DRAWINGS

FIG. 3A depicts a perspective view of an illustrative variation of an atherectomy system as described here. FIG. 3B shows an enlarged perspective view of a distal portion of the atherectomy system shown in FIG. 3A.

FIGS. 4A-4D depict illustrative methods by which an atherectomy system may be deployed intravascularly.

FIGS. 8A and 8B depict a perspective distal view and a side view, respectively, of a variation of a representative cutting element as described here. FIG. 8C is a cross-sectional view of the representative cutting element taken along line 8C-8C in FIG. 8B.

FIGS. 14A, 14B, and 14C depict a perspective view, side view, and bottom view, respectively of a variation of a cutting element as described here.

FIG. 15 depicts an illustrative method by which one variation of a cutting element as described here may be formed.

FIGS. 16A and 16B depict a variation of the atherectomy apparatuses described here.

FIGS. 19A-19E and 19F(1)-19F5 depict various views by which a variation of the atherectomy devices described here may be manipulated within the vasculature.

FIGS. 27A-27L depict an illustrative method of machining a variation of the cutting elements described here.

DETAILED DESCRIPTION

Figure 2:
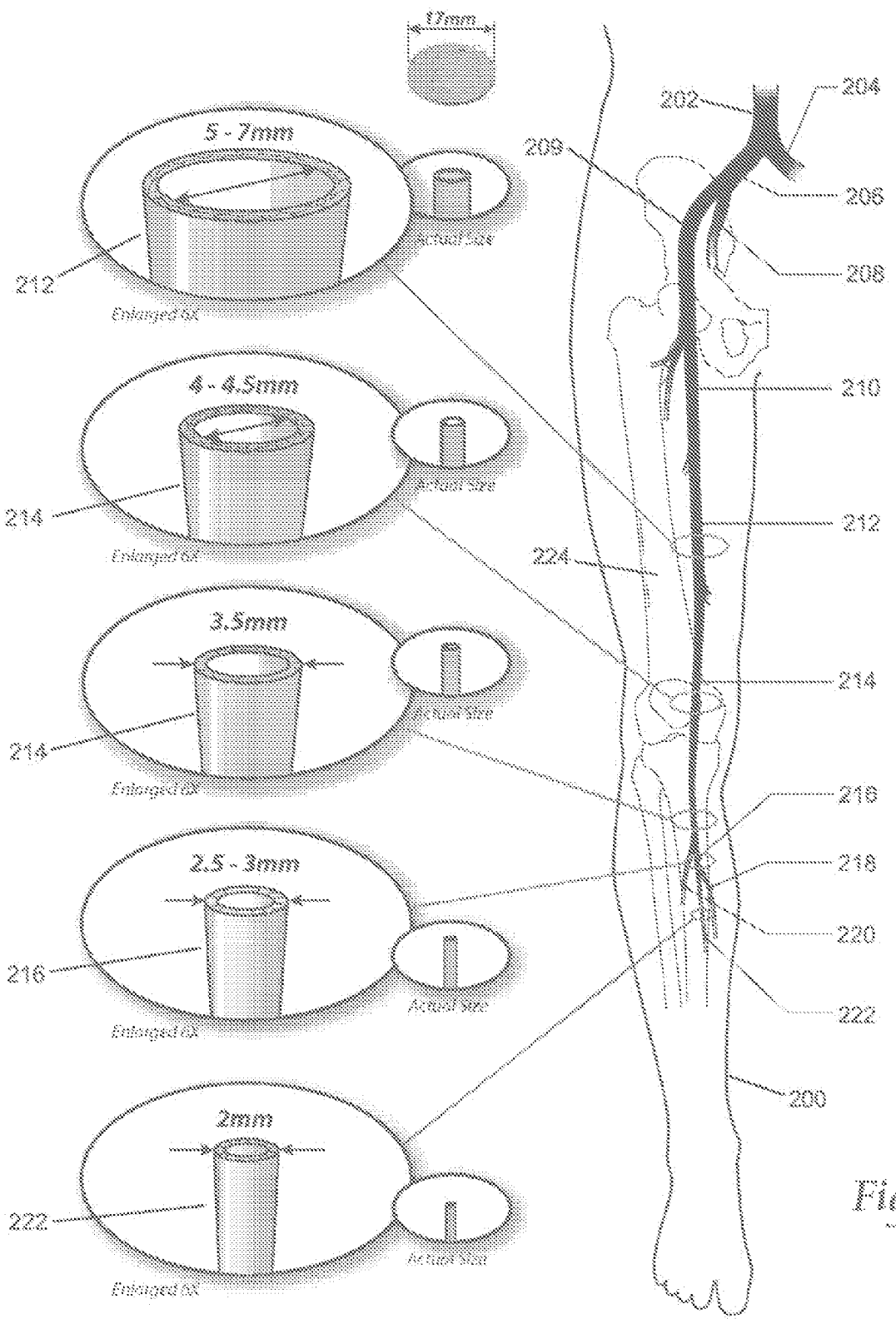
FIG. 2 depicts a diagrammatic anatomic view showing the major arteries of a right leg and typical variations in diameter of the various arteries.

One of the clinical challenges of atherectomy arises from the native anatomy of certain peripheral regions where atherectomy is indicated (for example, in the leg). Accordingly, it may be useful to describe the anatomy of the leg. FIG. 2 shows the anatomy of major arteries of a leg (200) (the right leg is shown for the purpose of illustration). Also shown there is the abdominal aorta (202), the left iliac artery (204), the right iliac artery (206), the internal iliac artery (208), the external iliac artery (209), the common femoral artery (210), the superficial femoral artery (212), the popliteal artery (214), the tibioperoneal trunk (216), the posterior tibial artery (218), the anterior tibial artery (220), and the peroneal artery (222). The diameters of the peripheral arteries of the leg generally taper from larger to smaller in the direction of arterial blood flow from above the knee to below the knee.

The abdominal aorta (202) is the largest artery in the body, and its diameter can range from 19 to 25 mm (about 0.75 to about 1 inch). The abdominal aorta successively branches or divides numerous times between the proximal and distal regions of the legs. Each successive branch or division may reduce the diameter of the arteries in the direction of arterial blood flow from the heart to the feet, and the tortuousity of the path generally increases.

The first branching is at the groin, into the left (204) and right (206) common iliac arteries. In the left leg, the left common iliac artery (204) branches into the internal (208) and external (209) iliac arteries. Near the head of the femur bone (224), the external iliac artery (209) becomes the common femoral artery (210) or "CFA". The CFA further connects to the superficial femoral artery (212) or "SFA". The SFA connects to the popliteal artery (214), which runs behind the flexible region of the knee. Above the knee, the SFA generally has a diameter of about 5 to 7 mm, or about 0.2 to 0.25 inch. Traversing distally below the knee (toward the feet), the popliteal artery (214) may further reduce in diameter to about 4 to 4.5 mm (0.157 inch to 0.177 inch), and then further to about 3.5 mm (0.137 inch). Traversing further distally, the popliteal artery (214) eventually branches again into the anterior tibial artery (220) and the tibioperoneal trunk (216), resulting in a further reduction in diameter to about 3.0 mm to 2.5 mm (0.118 inch to 0.098 inch). Traversing further distally, the tibioperoneal trunk further subdivides into the posterior tibial (218) and peroneal (222) arteries, further reducing diameter to about 2.0 mm (0.078 inch). Overall, the diameters of the peripheral arteries of the leg vary typically from about 2 mm (below the knee) to about 7 mm (above the knee).

Atherectomy devices are usually introduced into the vasculature though an iliac artery by either an ipsilateral (i.e., same side) or a contralateral (i.e., opposite side) approach, and typically advanced under fluoroscopic radiographic image guidance through the CFA and into the SFA. Currently, nearly all intravascular atherectomy cases are performed in the SFA, however, in a majority of these cases, potentially treatable atherosclerosis exists on multiple levels of the peripheral arteries, both above and below the knee. Accordingly, the devices and methods described here may be helpful in reaching these potential atherectomy sites.

Atherectomy Systems and Apparatuses

A. Overview

FIGS. 3A and 3B show a representative embodiment of the atherectomy systems described here. As shown there, the atherectomy system (300) may include an intravascular atherectomy apparatus (302) and a guide wire (304) over which the atherectomy apparatus (302) may be deployed. The guide wire (304) is preferably silicon-coated or non-coated (bare), or otherwise free of a PTFE coating. It should be appreciated, however, that in some variations the atherectomy systems described here may comprise a guide wire that includes a PTFE coating, or that does not include a guide wire at all.

The atherectomy apparatus (302) generally includes an elongated catheter body (306) having a central axis. The catheter body (306) may be sized and configured to be advanced over the guide wire (304) in a blood vessel from an external percutaneous access site. The access approach can be ipsilateral or contralateral, and down to the targeted region. For example, FIGS. 4A and 4B depict views of the anatomy of a patient with a distal portion of the atherectomy apparatus (302) advanced using an ipsilateral approach to a target region in the anterior tibial artery (220). As shown there, the atherectomy apparatus (302) may be introduced into an access site (400) in the right iliac artery (400). Conversely, FIGS. 4C and 4D depict views of the anatomy of a patient with a distal portion of the atherectomy apparatus (302) advanced in a contralateral approach. As shown there, a distal portion of the atherectomy apparatus (302) may be advanced through an access site (404) in the left iliac artery (204), across the iliac bifurcation, and down to the targeted site (in these figures, the targeted site is shown as a branch of the profunda artery (406). In order to follow the intravascular path from the access site to the target region, the catheter body (306) should possess physical and mechanical properties to allow the catheter body (306) to follow the guide wire through a bending, often tortuous intravascular path, as will be described in more detail below.

The atherectomy apparatus (302) may also include a handle (308) is coupled to the proximal (i.e., closest to the caregiver) end of the catheter body (306). The handle may be sized and configured to be securely held and manipulated by a caregiver outside an intravascular path. The handle may be manipulated from outside the intravascular path near the percutaneous access site, which may allow a caregiver to advance the catheter body through the intravascular path, which, in the leg, generally becomes more tortuous as one proceeds toward the distal regions of the legs (below the knee and toward the feet). Image guidance (e.g., CT, radiographic, in situ visualization carried on board the atherectomy apparatus or otherwise provided, or another suitable guidance modality, or combinations thereof) may be used to aid in advancement or positioning of the atherectomy apparatus (302). The catheter body (306) may be advanced to provide access to a targeted region where fat, cholesterol, and other substances have accumulated on the walls of arteries to form plaques or lesions, which will also in general be referred to as "occlusive materials."

The atherectomy apparatus (302) may further comprise a cutter assembly (310) at the distal end (e.g. farthest from the handle) end of the catheter body. Generally, the cutter assembly may act to cut and capture the occlusive material, and thereby remove occlusive material from the artery, which may open the artery to blood flow. In some variations, the cutter assembly (310) may include a rotatable cutter (312) at least partially housed within a concentric cutter housing (314). The cutter (312) may be rotatable within the housing around the central axis of the catheter body. In the variation shown in FIGS. 3A and 3B, the cutter housing (314) may be open at its distal-most end such that the distal-most end of the cutter may project a distance distally from the open housing (314). In some of these variations, when the cutter assembly (310) is deployed in the targeted region where the occlusive materials exist, there may be no structure or component of the atherectomy located in front of (i.e., distal to) the cutter assembly, and thus the first region of the atherectomy apparatus to interact with the plaque is the cutter assembly.

Figure 5A:
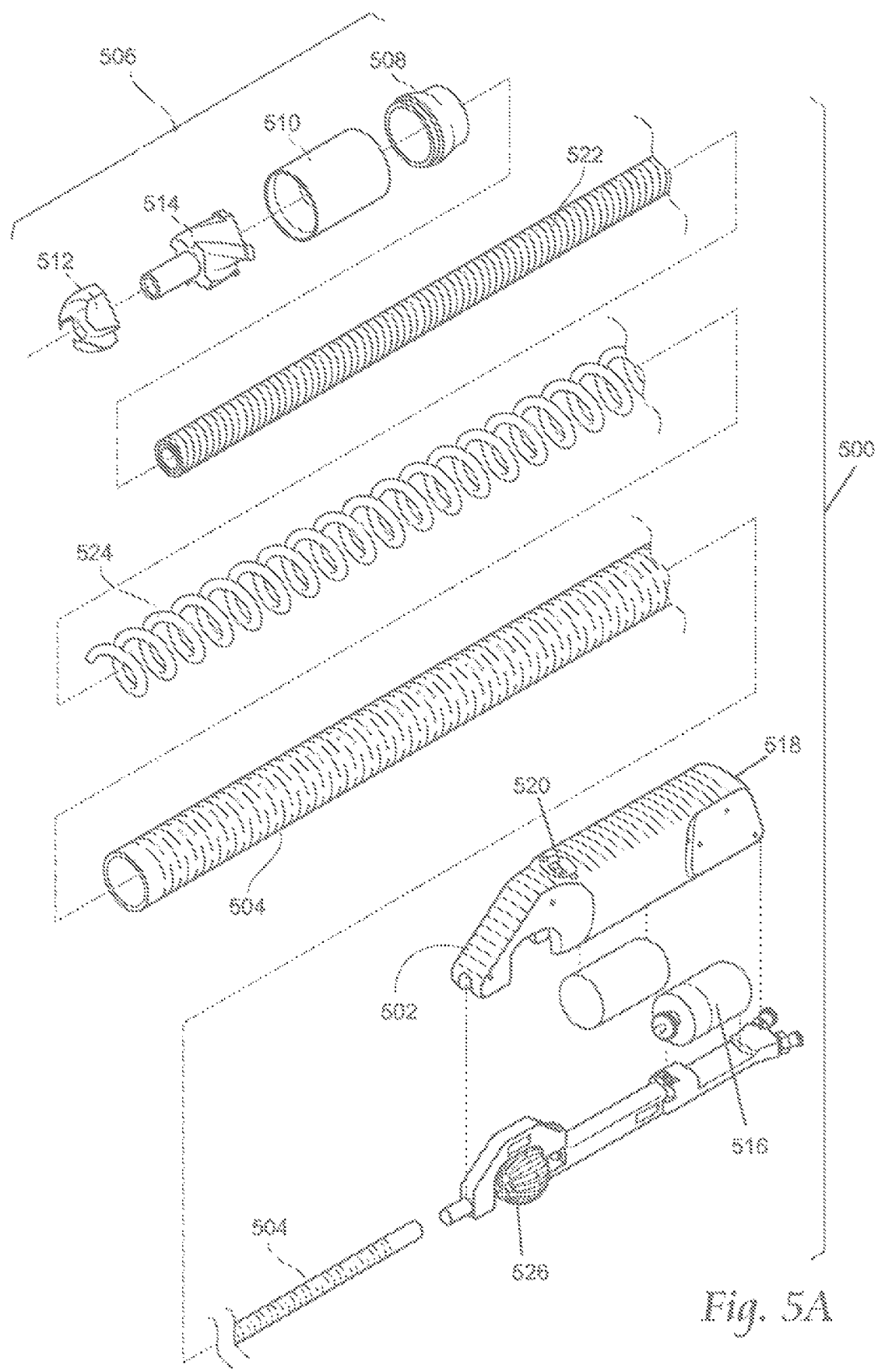
FIG. 5A depicts an exploded perspective view of a variation of the atherectomy systems described here.
Figure 5B:
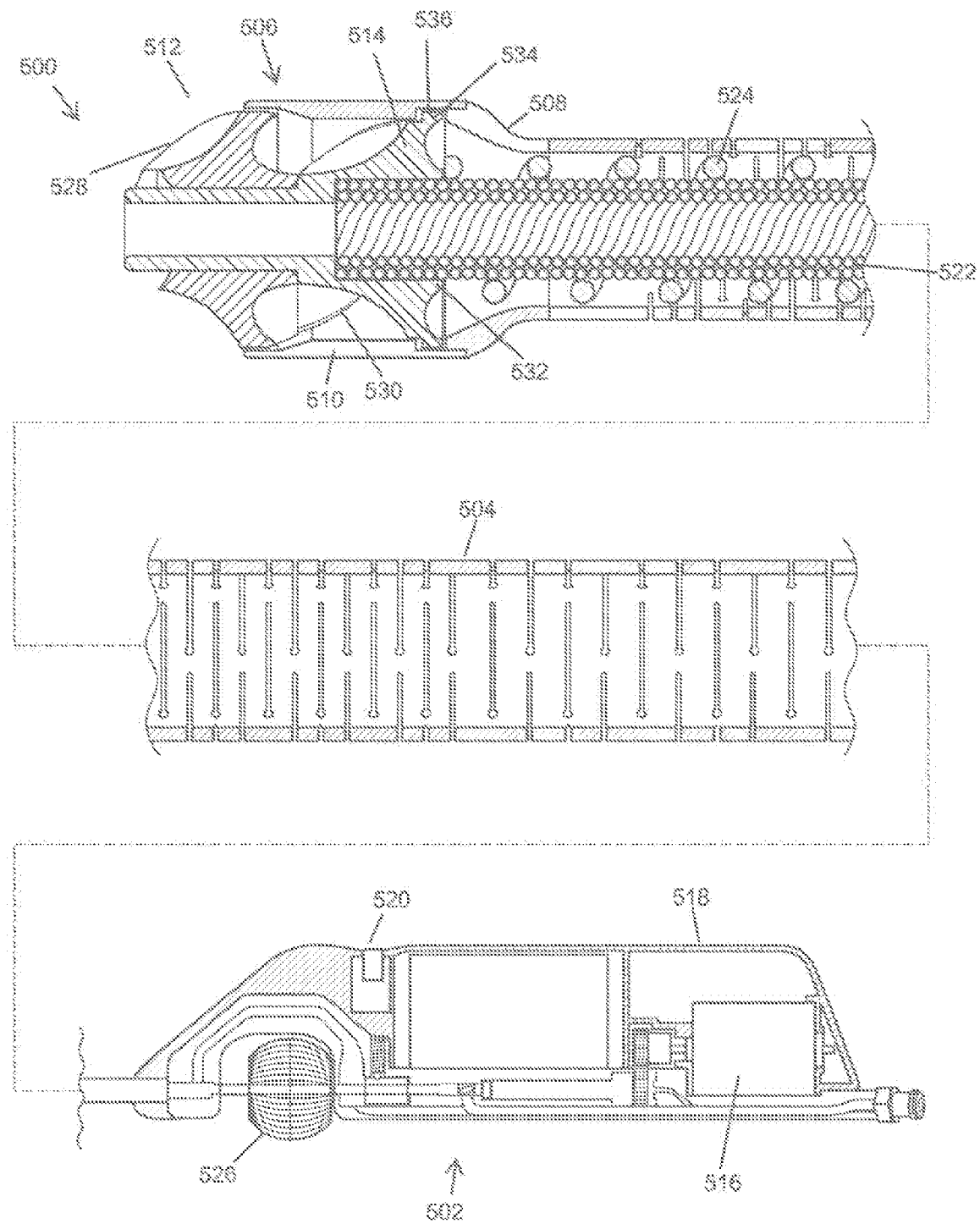
FIG. 5B depicts an assembled cross-sectional side view of the atherectomy system of FIG. 5A.

FIGS. 5A and 5B show an illustrative variation of an atherectomy apparatus (500) suitable for use with the atherectomy systems described here. As shown there, atherectomy apparatus (500) may comprise a handle (502), a catheter body (504), and a cutter assembly (506), such as described above with respect to FIGS. 3A and 3B. As shown in FIGS. 5A and 5B, the cutter assembly (506) may comprise a ferrule (508), a cutter housing (510), and a cutter including a first cutting element (512) and a second cutting element (514). It should be appreciated that the atherectomy apparatus (500) may comprise any suitable cutter assembly, such as those described in more detail below.

The atherectomy apparatus (500) may include a motor (516), which in the embodiment shown in FIGS. 5A and 5B, may be contained within a housing portion (518) of the handle (502). The motor is desirably battery operated, either by use of replaceable batteries, by use of rechargeable batteries, or combinations thereof. A motor controller may desirably provide a consistent supply of power through all operating conditions, including no load through excessive torque and stall conditions. A control switch (520) (e.g., slide switch, pushbutton, and/or potentiometer) may be provided to include an off/on function, and in some instances, one or more of a variety of other control functions, such as ramp up and/or ramp down, and/or variable speed. In some variations, the motor may run at about 12,000 RPM at 6 volts nominal. The operating parameters can be changed by adjusting the gear ratio.

As shown in FIGS. 5A and 5B, a torque shaft (522) may connect the motor (502) to the cutter. Specifically, the motor (502) may rotate the torque shaft (522), which may in turn rotate the cutter within the cutter housing (510) around the central axis of the catheter body. Rotation of the cutter of the cutter assembly (506) may cause the first (512) and/or second (514) cutting elements to cut occlusive material and convey the occlusive materials into the cutter housing (510) (a process also known as "debulking"). Preferably, the cutter assembly (506) captures the cut occlusive materials from the blood without the use of any vacuum aspiration (although it should be appreciated that in some variations, vacuum aspiration may assist conveyance of the cut occlusive material).

Additionally, the atherectomy apparatus (500) may further include an internal conveyor (524) on the torque shaft (522). As occlusive material is conveyed into the cutter housing (510) by the cutter, the conveyor (524) may convey the cut occlusive material further back (proximally) along the catheter body for discharge outside the patient's body. As mentioned above, this conveyance may occur without the use of vacuum aspiration assistance. Mechanical conveyance may complement distal capture. Because it does not require the assistance of vacuum aspiration, mechanical conveyance may minimize the risk of the artery collapsing around the cutter and the associated risk of perforation. Additionally, this conveyance may maximize the removal of tissue and blood components that have been damaged by contact with the cutter assembly.

B. The Catheter Body

1. Dimensions

For practical purposes, the outer diameter of any section of the catheter body, including the cutter assembly it carries, may be dictated at least partially by the anatomy of the intravascular path and the intended target region. Specifically, it may be desirable to maximize the cutting effectiveness of the cutter assembly by maximizing the diameter of the cutter, while minimizing the potential of puncture or trauma to the vessel. Additionally, the outer diameter of the catheter body/cutter assembly may also be dictated at least partially by the diameter of a guide sheath or introducer selected that may be placed at an access site to allow introduction of the atherectomy apparatus into the vasculature. It may be desirable to select a guide sheath or introducer sized to minimize pain, trauma, and blood loss during use, and to facilitate rapid closure of the access incision after removal, to thereby reduce the incidence of interventional complications.

As mentioned previously, diameters of the peripheral arteries of the leg vary typically from relatively small in regions below the knee (2.0 mm) to relatively large in regions above the knee (7.0 mm). For percutaneous access to the peripheral arteries, clinicians typically use guide sheaths sized from 5F (diagnostic) to 7F (interventional).

Assuming, for example, that a 7 French guide sheath would likely be, from a clinical perspective, the largest selected to access the larger vessels above the knee (4 mm to 7 mm), and allowing for a reasonable clearance tolerance between the catheter body/cutter assembly and the guide sheath, in some instances the outer diameter of the catheter body for introduction through such a guide sheath may be selected to be approximately equal to or less than about 2.4 mm. Assuming that a 5 F guide sheath would likely be, from a clinical perspective, the largest used to access the smaller vessels below the knee (2.5 mm to 3 mm), and allowing for a reasonable clearance tolerance between the catheter body/cutter assembly and the guide sheath, in some instances the outer diameter of the catheter body for introduction through such a guide sheath may be selected to be approximately equal to or less than about 1.8 mm. Assuming that an intermediate 6 French guide sheath would likely be, from a clinical perspective, the largest used to access the intermediate vessels near the knee (3 mm to 4 mm), and allowing for a reasonable clearance tolerance between the catheter body/cutter assembly and the guide sheath, in some instances the outer diameter of the catheter body for introduction through such a guide sheath may be selected to be approximately equal to or less than about 2.2 mm.

It may desirable that the outer diameter of the cutter assembly be maximized, to maximize the overall cutting area of the atherectomy assembly. When the cutter assembly of an atherectomy apparatus is the distal-most component of the apparatus, the cutter assembly may lead the way by cutting through the occlusive materials. With regard to the catheter body, however, there may functional and clinical benefits that arise when the outer diameter of the catheter body is not maximized to match the outer diameter of the cutter assembly. Reducing the diameter of the catheter body relative to the cutter assembly may minimize frictional contact between the catheter body and the vessel wall. This may lessen the force required to advance the catheter body through the vasculature and occlusive material, and may help prevent the catheter body from dragging against or sticking to tissue structures in the vessel, or otherwise impeding the progress of the cutter assembly through the occlusive materials.

For example, it may be desirable that the outer diameter of the catheter body proximal of the cutter assembly be sized smaller than the outer diameter of the cutter assembly. In other instances, it may be desirable that the outer diameter of the catheter body proximal of the cutter assembly be sized equal to or smaller than the outer diameter of the cutter assembly. For example, in the variation of atherectomy apparatus (500) described above with respect to FIGS. 5A and 5B, the catheter body (504) may have an outer diameter less than an outer diameter of the cutter assembly (506).

The reduced diameter of the catheter body may also permit the injection of radiographic contrast material around the catheter body in the guide sheath. For example, an atherectomy apparatus for introduction through a 7F introducer system may have a 2.4 mm diameter cutter assembly and a catheter body having a 2.2 mm diameter. In other variations, an atherectomy apparatus for introduction through a 5F or 6F introducer system may have a 1.8 mm diameter cutter assembly and a catheter body having a 1.6 mm diameter, or a 2.2 mm diameter cutter assembly and a catheter body having a 1.6 mm diameter.

2. Catheter Properties

In addition to the anatomical and clinical considerations that may be used in selecting an outer diameter of a catheter body, the catheter body may also desirably possess certain physical and mechanical properties, such as those described immediately below, which may enhance the function of the catheter body to support and guide passage of the cutter assembly through the intravascular path and the occlusive materials.

(i) Column Stiffness (Pushability)

One potentially desirable property for the catheter body includes column stiffness. Expressed in units of inch/foot-pounds, column stiffness is the capability of the catheter body to withstand an axial load or compression while resisting bending. Column stiffness can be measured and characterized in conventional ways, and may be referred to as "pushability" herein. Generally, a higher column stiffness is desirable, and may allow the catheter body to transmit a higher axial force (compression) applied at the handle to the cutter assembly without buckling. Accordingly, it may be desirable that the catheter body possess column stiffness sufficient to push the cutter assembly over the guide wire without buckling. A column stiffness of 0.050 inches/lbf or greater may be desirable for the catheter bodies described here.

(ii) Tensile Stiffness (Pullability)

Another potentially desirable property for the catheter body comprises tensile stiffness. Expressed in units of inch/foot-pounds, tensile stiffness is the capability of the catheter body of withstanding tension while being stretched or pulled before the cross section starts to significantly contract (called "necking"). Tensile stiffness can be measured and characterized in conventional ways, and may be referred to as "pullability" herein. Generally, a high tensile stiffness may be desirable, and may allow the catheter body to be pulled proximally along an intravascular path (e.g., to withdraw the cutter assembly) without necking. A tensile stiffness of 0.050 inches/lbf or greater may be desirable for the catheter bodies described here.

(iii) Torsional Stiffness (Torquability)

Another potentially desirable property for the catheter body comprises torsional stiffness. Expressed in degrees/ounce-inch, torsional stiffness is the capability of the catheter body to transmit a rotational load (torque) without untwisting, over-twisting and/or deforming. Torsional stiffness may be measured and characterized in conventional ways, and may be referred to as "torquability" herein. The torsional stiffness may control the capability of the catheter body to transmit a given amount of rotation applied at its proximal end (i.e., the handle) to achieve a comparable amount of rotation at its distal end (i.e, the cutter assembly). A higher torsional stiffness may be desirable, to better allow for rotational transmission along the atherectomy apparatus (i.e., around a guide wire), without twisting or deforming. A torsional stiffness that achieves a 1:1 relationship between rotation applied at the proximal end and the rotation observed at the distal end may be desirable for the catheter bodies described here.

(iv) Bending Stiffness (Trackability)

Another potentially desirable property for the catheter body comprises bending stiffness. Expressed in units of a bend radius (in inches), bending stiffness is the ability of the catheter shaft to bend in response to an applied bending force, without breaking or deforming (i.e., without taking a set). Bending stiffness is an extensive material property that can be measured and characterized in conventional ways, and may be referred to as "trackability" herein. Generally, a lower bending stiffness may be desirable to allow the catheter body to be navigated over a guide wire around sharp bends in the vasculature. A targeted bending stiffness of 0.5 inches (bend radius) or greater at mid-length of the catheter body may be desirable for the catheter bodies described here. If the catheter body includes an active deflection component at its distal end (as will be described in greater detail later), a targeted bending stiffness of 1.0" (bend radius) at the deflectable distal end may be desirable for the catheter bodies described here. A prescribed minimum bend radius also makes it possible to coil the catheter body for packaging without taking a set.

Conventionally, trackability is thought to be inversely related to pushability/pullability and torquability. That is, greater pushability, pullability, and/or torquability in a catheter body may reduce the trackability of the catheter body. However, the catheter bodies described here may balance the pushability, pullability, torquability, and trackability for a given catheter body. The result may be a catheter body that is trackable, yet also possesses the requisite column strength, tensile strength, and torsional stiffness to be sufficiently pushable, pullable and torquable to allow navigation and advancement of a cutter assembly.

The overall trackability of a given catheter body (in terms of its ability to reliably navigate over a guide wire) may be influenced mainly by the physical and mechanical characteristics of the catheter body at its distal end. The pushability, pullability, and torquability may be influenced mainly by the physical and mechanical characteristics of the catheter body proximal to its distal end. That is, the overall configuration of different regions of a catheter body may impart characteristics to the overall length of the catheter body, which may allow for optimization of the overall pushability, pullability, torquability, and trackability of the catheter body.

3. Illustrative Catheter Body Variations

Generally, the column stiffness, tensile stiffness, torsional stiffness, and bending stiffness for a catheter body may be at least partially determined by its constituent material or materials, the dimensions of catheter body (e.g., the interior diameter, the outer diameter, wall thickness, etc.) and other structural features such as patterning.

FIGS. 6A-6C and 7A-7C depict illustrative variations of the catheter bodies suitable for use with the atherectomy apparatuses described here. In these variations, the catheter bodies may be fabricated from a metal tube (for example, a type 304 stainless steel tube or the like). The dimensions of the tube may depend at least partially on the intended use of the atherectomy apparatus. For example, in some variations the outer diameter of the tube may desirably be about 2.2 mm, while in other variations the outer diameter of the tube may be about 1.6 mm. Additionally or alternatively, the wall thickness of the tube may preferably be about 0.288 mm. Additionally or alternatively, the overall length of the tube may preferably be about 1437 mm (about 56.56 inches).

A metal tube with some or all of the dimensions described immediately above may provide a high degree of pushability, pullability, and torquability, the baseline bending stiffness may limit the trackability of the catheter body given the length of the catheter body. Accordingly, in some variations, the bending stiffness of the metal tube may be incrementally modulated along the length of the catheter body by creating zones of cut patterns along at least a portion of the length of the catheter body. The cut patterns may be formed in any suitable manner (e.g., via laser cutting), and the zones may impart a desired profile of bending stiffness over the length of the catheter body. For example, cut pattern zones may be used to incrementally decrease the bending stiffness in a stepwise fashion from proximal end to distal end, to provide a minimum bending stiffness conducive to trackability at the distal end (where trackability is more desirable). The stepwise fashion in which the bending stiffness is decreased may be configured in a manner to help maintain the overall pushability, pullability, and torquability.

(i) Helical Cut Patterns

Figure 6A:
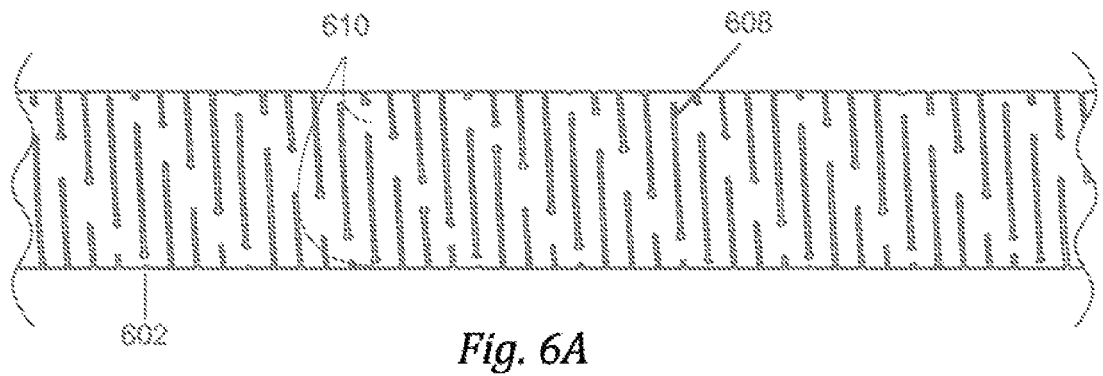
FIG. 6A is a side view of a portion of a variation of a catheter body suitable for use with the atherectomy systems described here.
Figure 6B:
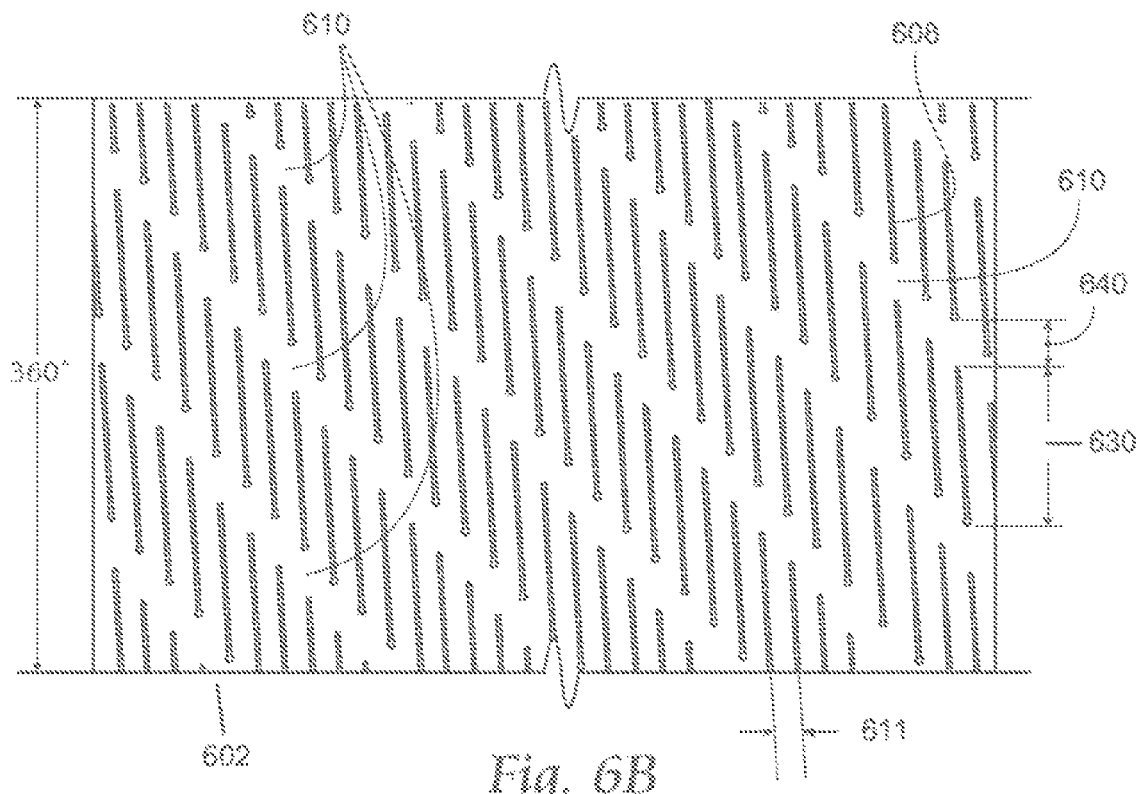
FIG. 6B depicts a plane view of the portion of the catheter body shown in FIG. 6A opened up into a sheet configuration.
Figure 6C:
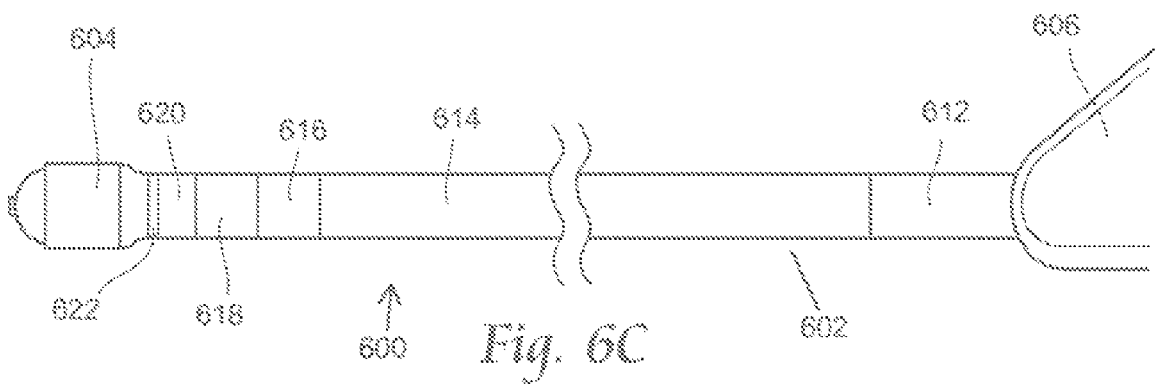
FIG. 6C depicts a side view of an atherectomy apparatus including the catheter body shown in FIGS. 6A and 6B.

In some variations, one or more zones may comprise a helical cut pattern. For example, FIGS. 6A-6C depict a variation of an atherectomy apparatus (600) comprising a catheter body (602), a cutter assembly (604), and a handle (606). Specifically, FIG. 6C shows a side view of the atherectomy apparatus (600), FIG. 6A shows a side view of a section of the catheter body (602), and FIG. 6B depicts a plane view of the section of the catheter body shown in FIG. 6A opened up into a sheet. As shown there, the catheter body (602) may be formed from a tube and may comprise zones of cut patterns in the form of helical cuts (608) (which may be laser cut) that thread around the longitudinal axis of the catheter body (602). The helical cuts (608) are separated by uncut regions call "posts" (610). The direction (thread) of a given pattern can be characterized in terms of its direction about the axis—a left hand thread (when viewed from the proximal end, counter-clockwise) or a right hand thread (when viewed from the proximal end, clockwise). The pattern can be further characterized in terms of the arc (630) of the helical cuts (608) about the longitudinal axis (in degrees), and the arc (640) of the uncut region/post between cuts (610) about the longitudinal axis (in degrees). The pattern can be further characterized in terms of the axial separation of the cuts (in inches) along the axis, which can also be called the "pitch" (611).

For example, a cut pattern characterized as "Right Hand Thread, 100° Cut/30° Uncut, 0.012" Pitch" may be used to describes a helical cut pattern that extends clockwise when viewed from the proximal end of the catheter body, in which the helical cuts thread 100 degrees about the longitudinal axis of the, the posts between helical cuts extend 30 degrees about the axis, and wherein helical cuts are axially separated by 0.012 inches.

Because the helical cuts take away material from the tube, the bending stiffness of the tube may decrease, and may allow the tube/catheter body to bend more easily (thereby increasing trackability). This change in bending stiffness may be at least partially determined by the arc of the helical cuts and posts, as well as the pitch of the helical cuts. The cut pattern just described can be characterized as a "three-post" pattern, which reflects that a ninety-degree region of uncut metal appears in the span of three post; i.e., $n \times 30° = 90°$, where $n=3$, the number of posts.

In comparison, a cut pattern characterized as "Right Hand Thread, 135° Cut/45° Uncut, 0.012" Pitch" may be used to describe a helical cut pattern that extends clockwise when viewed from the proximal end of the catheter body, in which the helical cuts thread 135 degrees about the longitudinal axis of the, posts between helical cuts extend 45 degrees about the axis, and wherein helical cuts are axially separated by 0.012 inches. This cut pattern can be characterized as a "two-post" pattern, which reflects that a ninety-degree region of uncut metal appears in the span of two post; i.e., $n \times 45° = 90°$, where $n=2$, the number of posts.

As mentioned above, modifying the arc of the helical cuts, the arc of the posts, and/or the pitch of the helical cuts may alter the trackability of the catheter body. For example, increasing the arc of the helical cuts may decrease the bending stiffness and increase the trackability. Conversely, increasing the arc of the posts may increase the bending stiffness and decrease the trackability. Increasing the pitch may increase the bending stiffness while decreasing the pitch may decrease the bending stiffness. In some instances, it may be desirable for the pitch to be between about 0.006 inches and about 0.016 inches. A pitch below 0.006 inches may be difficult to achieve with conventional laser techniques as little uncut material remains, and in some instances a pitch above 0.016 inches may lose trackability.

By choosing a cut pattern, and/or by varying the cut pattern in a stepwise manner along the length of the catheter body, the bending stiffness of the catheter body can be incrementally reduced over its length to impart trackability, and may be done without diminishing the desired magnitudes of column stiffness, tensile stiffness, and torsional stiffness to a magnitude below that conducive to pushability, pullability, and torquability. As mentioned above, for some variations, the pitch may be varied between 0.006 inches and 0.016 inches to alter the bending stiffness.

The catheter bodies may have any number of zones/regions having different cut patterns (or in some zones, no cut pattern at all). For example, in the variation of atherectomy apparatus (600) shown in FIG. 6C, the catheter body (602) may comprise a first region (612) extending from the handle (606), a second region (614) extending distally from the first region (612), a third region (616) extending distally from the second region (614), a fourth region (618) extending distally from the third region (616), a fifth region (620) extending distally from the fourth region (618), and a sixth region (622) extending distally from the fifth region (620). In some variations each region may have a lower bending stiffness than the regions proximal to that region. In other variations, each region except the distal-most region may have a lower bending stiffness that the regions proximal to that region. Additionally, while shown in FIG. 6C as having six regions, it should be appreciated that the catheter bodies may include any number of regions (e.g., one, two, three, four, or five or more), and some or all of the regions may include a cut pattern such as those described here. For example, Table 1 includes one variation of cut patterns that may be utilized with a six-region catheter body (602) as shown in FIG. 6C:

TABLE 1

| Region | Axial Length | Cut Pattern (Right Hand Thread) | Pitch |
| --- | --- | --- | --- |
| 1 (Most Proximal) | 4.0" | Uncut | N/A |
| 2 | 47.04" | 100° Cut 30° Uncut | 0.012" |
| 3 | 2.0" | 110° Cut 30° Uncut | 0.010" |
| 4 | 2.0" | 110° Cut 30° Uncut | 0.008" |

TABLE 1-continued

| Region | Axial Length | Cut Pattern (Right Hand Thread) | Pitch |
|---|---|---|---|
| 5 | 1.5" | 110° Cut 30° Uncut | 0.006" |
| 6 (Most Distal) | .030" | Uncut | N/A |

(ii) Brickwork Cut Patterns

Figure 7A:
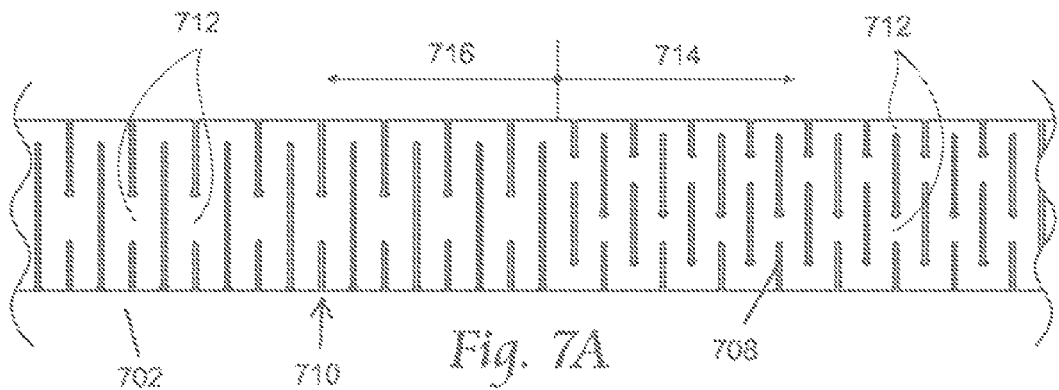
FIG. 7A is a side view of a portion of a variation of a catheter body suitable for use with the atherectomy systems described here.
Figure 7B:
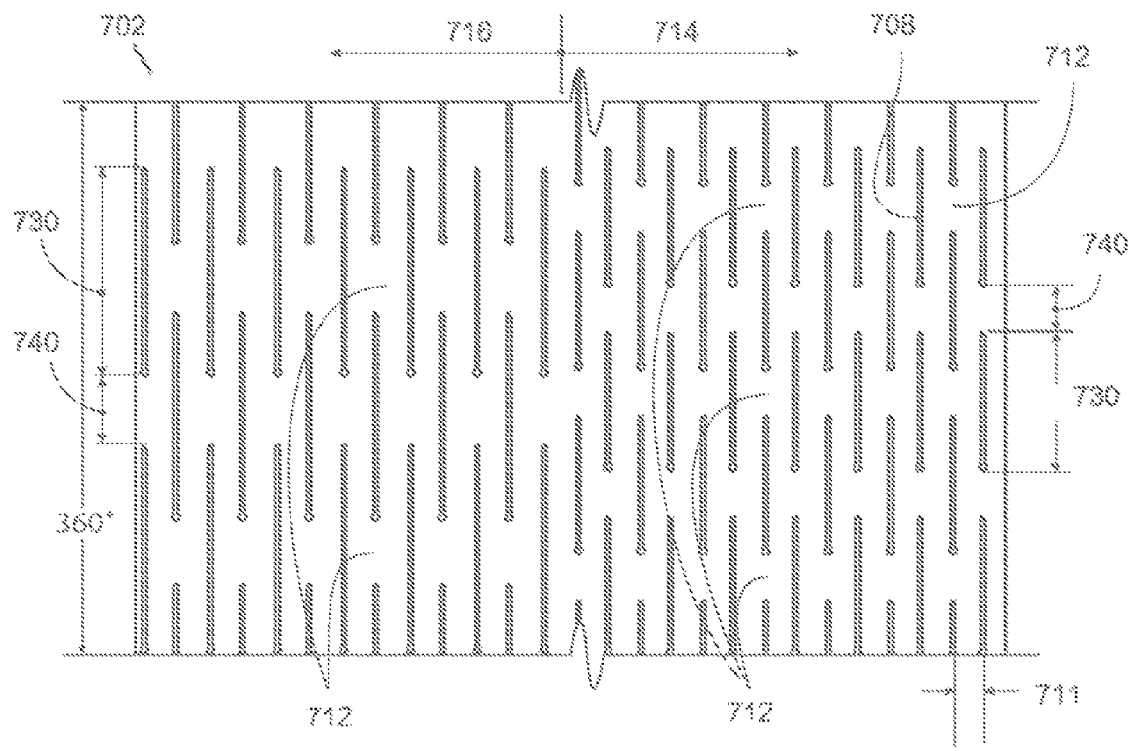
FIG. 7B depicts a plane view of the portion of the catheter body shown in FIG. 7A opened up into a sheet configuration.
Figure 7C:
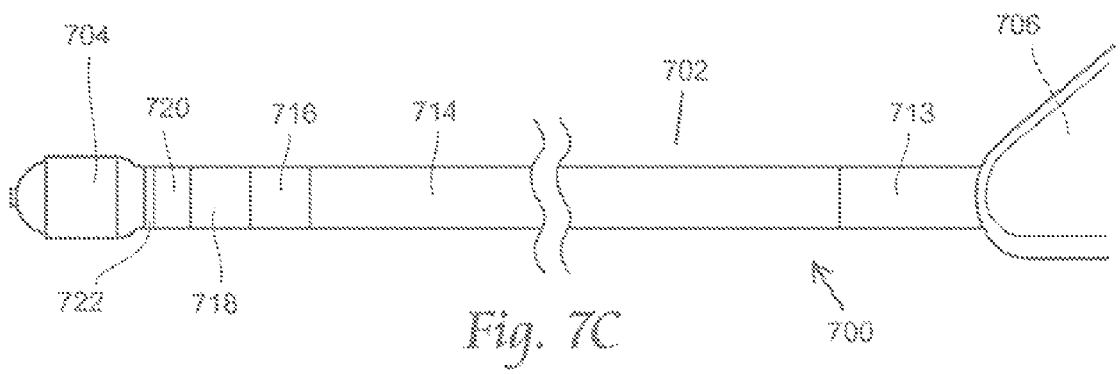
FIG. 7C depicts a side view of an atherectomy apparatus including the catheter body shown in FIGS. 7A and 7B.

In some variations, one or more zones may comprise a brickwork cut pattern. For example, FIGS. 7A-7C depict a variation of an atherectomy apparatus (700) comprising a catheter body (702), a cutter assembly (704), and a handle (706). Specifically, FIG. 7C shows a side view of the atherectomy apparatus (700), FIG. 7A shows a side view of a section of the catheter body (702), and FIG. 7B depicts a plane view of the section of the catheter body shown in FIG. 7A opened up into a sheet. As shown there, the catheter body (702) may be formed from a tube and may comprise zones of cut patterns in the form of brickwork cuts (708) (which may be laser cut) that thread around the longitudinal axis of the catheter body (702). The brickwork cuts (708) are generally normal to the longitudinal axis of the catheter body (704), and may form rows (710) of brickwork cuts (708) along the catheter body (704). In each row (710), the brickwork cuts (708) may be separated by uncut posts (712), and rows (710) are separated axially along the longitudinal axis. The pattern can be characterized in terms of the arc (730) of the brickwork cuts (708) about the longitudinal axis (in degrees), and the arc (740) of the uncut region/posts (712) about the longitudinal axis (also in degrees). The pattern can be further characterized in terms of the axial separation of the rows (710) along the axis, which can also be called the "pitch" (711). The pattern can also be characterized in terms of the offset between successive rows (in degrees). For example, in some variations, the positioning of the brickwork cuts (708) and posts (712) in a first row may be offset from those of an immediately adjacent row by about 45 degrees about the longitudinal axis (this may be referred to as "alternating brickwork" herein). In some variations, each row (710) may comprise four equally-spaced brickwork cuts (708), with successive rows offset in an alternating brickwork manner.

As discussed immediately above, a cut pattern characterized as "Brick Work Cut Pattern, 90° Cut/30° Uncut, 0.011" Pitch, Alternating" may be used to describe a brickwork cut pattern in which the brickwork cuts of a row extend 90 degrees about the axis, the posts of a row between brickwork cuts extend 30 degrees about the axis, successive rows are axially separated by 0.011 inches and a rotational offset by about 45 degrees.

The brickwork cut pattern, like the helical cut pattern, takes away material from the tube, which may reduce the bending stiffness of the tube and may allow the tube/catheter body to bend more easily (thereby increasing trackability). This change in bending stiffness may be at least partially determined by the arc of the brickwork cuts and posts, the pitch between rows, and the offset between rows.

The brickwork cut pattern just described can be characterized as a "three-post" pattern, which reflects that a ninety-degree region of uncut metal appears in the span of three posts; i.e., $n \times 30° = 90°$, where n=3, the number of posts.

In comparison, a cut pattern characterized as "Brick Work Cut Pattern, 135° Cut/45° Uncut, 0.011" Pitch, Alternating" may be used to describe a brickwork cut pattern in which the brickwork cuts of a row extend 135 degrees about the axis, the posts of a row between brickwork cuts extend 45 degrees about the axis, successive rows are axially separated by 0.011 inches and a rotational offset of 45 degrees This brickwork cut pattern can be characterized as a "two-post" pattern, which reflects that a ninety-degree region of uncut metal appears in the span of two post; i.e., $n \times 45° = 90°$, where n=2, the number of posts.

As mentioned above, modifying the arc of the brickwork cuts, the arc of the posts, the pitch of the brickwork cuts, and/or the offset between rows may alter the trackability of the catheter body. For example, increasing the arc of the brickwork cuts may decrease the bending stiffness and increase the trackability. Conversely, increasing the arc of the posts may increase the bending stiffness and decrease the trackability. Increasing the pitch may increase the bending stiffness while decreasing the pitch may decrease the bending stiffness. In some instances, it may be desirable for the pitch to be between about 0.006 inches and about 0.016 inches. A pitch below 0.006 inches may be difficult to achieve with conventional laser techniques as little uncut material remains, and in some instances a pitch above 0.016 inches may lose trackability.

In transmitting an axial load (pushing or pulling) a catheter body having a brickwork pattern, as above described, may not undergo twisting, which may be experienced when the catheter body has a helically-cut pattern. Brickwork patterns may additionally exhibit an increased column, tensile, and torsional stiffness at a given bending stiffness.

By choosing a cut pattern, and/or by varying the cut pattern in a stepwise manner along the length of the catheter body, the bending stiffness of the catheter body can be incrementally reduced over its length to impart trackability, and may be done without diminishing the desired magnitudes of column stiffness, tensile stiffness, and torsional stiffness to a magnitude below that conducive to pushability, pullability, and torquability. As mentioned above, for some variations, the pitch may be varied between 0.006 inches and 0.016 inches to alter the bending stiffness.

The catheter bodies may have any number of zones/regions having different cut patterns (or in some zones, no cut pattern at all). For example, in the variation of atherectomy apparatus (700) shown in FIG. 7C, the catheter body (702) may comprise a first region (713) extending from the handle (706), a second region (714) extending distally from the first region (713), a third region (716) extending distally from the second region (714), a fourth region (718) extending distally from the third region (716), a fifth region (720) extending distally from the fourth region (718), and a sixth region (722) extending distally from the fifth region (720). In some variations each region may have a lower bending stiffness than the regions proximal to that region. In other variations, each region except the distal-most region may have a lower bending stiffness that the regions proximal to that region. Additionally, while shown in FIG. 7C as having six regions, it should be appreciated that the catheter bodies may include any number of regions (e.g., one, two, three, four, or five or more), and some or all of the regions may include a cut pattern such as those described here. For example, Table 2 includes one variation of cut patterns that may be utilized with a six-region catheter body (702) shown in FIG. 7C:

TABLE 2

| Region | Axial Length | Square Cut Pattern (Brickwork) | Pitch |
|---|---|---|---|
| 1 (Most Proximal) | 4.0" | Uncut | N/A |
| 2 | 47.04" | 90° Cut 30° Uncut | 0.012" |
| 3 | 2.0" | 135° Cut 45° Uncut | 0.012" |

TABLE 2-continued

| Region | Axial Length | Square Cut Pattern (Brickwork) | Pitch |
|---|---|---|---|
| 4 | 2.0" | 135° Cut 45° Uncut | 0.012" |
| 5 | 1.5" | 135° Cut 45° Uncut | 0.012" |
| 6 (Most Distal) | .030" | Uncut | N/A |

A catheter body having either a helical cut pattern or a brickwork cut pattern can be lined or jacketed with a polymeric material, and further may be treated to produce hydrophilic, hydrophobic, or drug binding (heparin, antimicrobial) properties.

4. Catheter Body Rotation

In some variations, the catheter body can be coupled to a post on the handle that is sized and configured to rotate in response to rotation of a control knob. For example, the atherectomy apparatus (500) described above with respect to FIGS. 5A and 5B may comprise a rotation knob (526). Rotation of the knob may apply torque to the catheter body to selectively rotate the cutter assembly. An indexing mechanism can be provided to provide stepwise control, with tactile and/or audible feedback, so that the caregiver maintains knowledge of the rotational position of the cutter assembly without taking their eye off the radiographic or otherwise provided in-situ image.

It is also possible to apply torque to the catheter body by rotating the handle itself. Selective rotation of the cutter assembly can thus be finely controlled by a combination of control knob manipulation and handle twisting.

C. The Cutter Assembly

As mentioned above, the atherectomy device may comprise a cutter assembly. The cutter assembly may comprise a ferrule, a cutter housing, and a cutter comprising at least one cutter element. In variations in which the cutter assembly comprises a ferrule, the cutter assembly may be joined to the distal end of the catheter body by the ferrule.

1. The Cutter Housing

As mentioned previously, the cutter assembly may include a housing in which a cutter rotates. It may be desirable to maximize the outer diameter of the cutter assembly (and with it, the cutter housing) to maximize the cutting area that may be cut by the cutter assembly. The size of the cutter assembly may be limited depending on the intended intravascular path and the region targeted for treatment, to help reduce the likelihood that the cutter assembly will cut or otherwise damage the vessel wall.

In some of the variations described here, a cutter assembly sized for introduction through a 7 French guide sheath may have an outer diameter of about 2.4 mm (which, in some variations, may be larger than the outer diameter of a companion catheter body, as described in more detail above). A cutter assembly having such an outer diameter may be used, for example, for access to the larger vessels above the knee (e.g., vessels between about 4 mm and about 7 mm). In other variations described here, a cutter assembly sized for introduction through a 5 or 6 French guide sheath may have an outer diameter of about 1.8 mm to about 2.2 mm (which, in some variations, may be larger than the outer diameter of a companion catheter body, as described in more detail above). A cutter assembly having such an outer diameter may be used, for example, for access to the smaller vessels at or below the knee (e.g., vessels between about 2.5 mm and about 4 mm).

The housing may or may not be dynamic (i.e., able to rotate relative to the catheter body). In variations where the housing is dynamic, the housing may be configured to rotate at the same speed or at a different speed than the cutter elements. Additionally, the cutter housing may be dynamically driven to rotate in the same direction or in a counter direction relative to the cutter.

The leading edge of the cutter housing, which defines the periphery of the distal opening through which the cutter projects, may desirably be rounded and does not present a sharp distal edge. In these variations, a rounded distal housing may reduce the possibility that the peripheral edges of the housing catch on the wall of the guide sheath during introduction therethrough. Additionally, a rounded distal edge may also tend to glance off tissue without grabbing or catching on the tissue, which may minimize the resistance felt by the atherectomy apparatus during advancement. It should be appreciated that in some variations the cutter housing may have a sharp or beveled distal edge. In some of these variations, the cutter housing may have an inner bevel. In other variations, the cutter housing may have an outer bevel.

In some variations, the outside diameter of the cutter may be less than the inside diameter of the cutter housing to create a desired cutting gap between the two. A larger gap may produce a larger cutting volume, but too large of a gap may permit tissue to enter the cutter housing while bypassing the cutter. Representative dimensions will be described in more detail later. In other variations, the outside diameter of a portion of the cutter may be greater than or equal to the diameter of the cutter housing. In these variations, the cutter may cut a larger diameter of tissue, which may reduce the likelihood that the cutter housing rubs against tissue during advancement while cutting, thereby facilitating advancement of the device.

2. The Torque Shaft

Within the housing, the cutter may be rotationally driven by a torque shaft. The torque shaft may be, in turn, driven by the motor in the handle. The torque shaft may be fabricated from any suitable material, preferably one or more materials that may be consistent with the pushability, pullability, torquability, and trackability of the catheter body, as described above. For example, the torque shaft may comprise a metal braid and/or one or more metal coils, and one or more portions of the torque shaft embedded in a polymer, e.g., PEBAX, polyurethane, polyethylene, fluoropolymers, parylene, polyimide, PEEK, and/or PET. In some variations, the torque shaft may be made from a rigid material such as plastic, rendered flexible by incorporation of a spiral relief or groove.

In some variations (such as the torque shaft (522) depicted above with respect to FIGS. 5A and 5B), the torque shaft may comprises a flexible wire coil wound about a central lumen. The central lumen may be sized to accommodate the passage of a guide wire therethrough. The flexible wire coil may preferably be wound in the same direction as the intended direction of rotation of the torque shaft, which may cause the coil to open up if torsional resistance to rotation is encountered (as opposed to clamping down, which may cause the torque shaft to lock on to a guide wire positioned in the central lumen).

Generally, the torque shaft may be coupled to a cutter of a cutter assembly at or near the distal end of the torque shaft, and may be attached to the motor (e.g., by gearing) at or near the proximal end of the torque shaft. In some variations (such as the atherectomy apparatus (500) depicted in FIGS. 5A and 5B), the cutter assembly may include a central lumen that may communicate with the central lumen/guide wire lumen of the torque shaft.

3. The Geometry of the Cutting Elements

As mentioned above, in some variations, the cutter of a cutter assembly may comprise multiple cutting elements. For example, in the variation of the atherectomy apparatus (500) described above with respect to FIGS. 5A and 5B, the cutter assembly (506) may comprise a cutter having first (512) and second (514) cutting elements. As shown there, the first cutting element (512) may be positioned distally of second cutting element (514). The first cutting element (512) may comprise one or more cutting edges (528) which may at least partially project beyond the distal end of the cutter housing (510). In some variations, at least a portion of the first cutting element (512) may have a diameter greater than or equal to the diameter of the cutter housing (510). The second cutting element (514) may be at least partially housed within the cutter housing (510), and may comprise one or more cutting edges (530). As shown in FIG. 5B, the cutting edges (530) of the second cutting element (514) may be entirely enclosed within the cutter housing (510). Generally, the first (512) and second (514) cutting elements may be physically coupled together (e.g., by adhesives or welding) for rotation in unison.

The torque shaft may couple to a journal (532) in the second cutting element. When the first (512) and second (514) cutting elements are physically coupled together, the torque shaft may rotate both the first cutting element and second cutting element in unison. A proximal flange (534) on the second cutting element (514) may be seated within a relieved proximal groove (536) in the cutter housing (510). The relieved proximal groove (536) may serve as an axial retainer for the first (512) and second (514) cutting elements within the cutter housing.

(i) The First Cutting Element

FIGS. 8A-8D depict an illustrative variation of a first cutting element (800) suitable for use with the cutter assemblies described here. In some variations, the first cutting element (800) may be machined from a hard metallic material (e.g., 440C stainless steel) and may have a generally hemispherical configuration that includes at least one helical flute (802) (shown there as a right-hand twist, although it should be appreciated that the at least one helical flute (802) may have a left-hand twist). While shown in FIGS. 8A-8D as having two helical flutes (802), it should be appreciated that the first cutting element (800) may comprise any suitable number of helical flutes (802) (e.g., one, two, three, four, or more helical flutes). Each cutting flute may form a cutting blade (803) having a cutting edge (804).

The first cutting element may be machined to shape the structure of the helical flutes (802) within the desired hemispherical geometry. When supported in an extended, distally projecting relationship relative to the cutter housing (e.g., by virtue of the connection to a second cutting element, as described in more detail above), the hemispherical, fluted geometry may be sized and configured to optimize the capability of the cutting blade or blades to cut through and capture occlusive materials, while minimizing the risk of the cutting blade or blades grabbing or digging into tissue, wrapping tissue, and otherwise causing the motor to stall and overload.

The geometry of each flute may be purposely shaped for the above-mentioned purposes, and the flute geometry may be characterized with reference to a combination of angles (or ranges of angles), comprising a rake angle, a relief angle, a flute angle, and a helix angle. Additionally, while shown in FIGS. 8A-8D as having a hemispherical outer profile, it should be appreciated that the front cutting element may any external profile, such as an egg-shaped outer profile.

(a) Rake Angle

For each flute, the rake angle (806) (best shown in FIG. 8C) can be defined as the angle measured between (i) a radius (808) drawn from the rotational axis of the cutting blade (810) to the most radially distant edge (804) of the blade (803) and (ii) a tangent (810) drawn from the inner face of that blade (803). The rake angle may describe the angle of the cutting edge (804) relative to the material to be cut.

In some variations, each flute of the first cutting element may possess a positive rake angle (i.e., the inner face of the cutting blade slants inward or back from the cutting edge). The positive rake angle of each flute is preferably large, and in some instances may be between greater than about 20 degrees. In some of these variations, the rake angle is preferably greater than about 40 degrees. In some of these variations, the rake angle may be between about 60 degrees and 80 degrees (referred herein as a "high" rake angle). In some variations, the rake angle may be between 65 degrees and 75 degrees. In some variations, the rake angle may be about 70 degrees.

Generally, a device having a positive high rake angle may be well suited for cutting occlusive materials having less calcium, which may have a fibrous, fleshy, and/or rubbery consistency. The rubbery consistency may cause conventional cutters to deflect away from these materials, causing conventional devices to lose trackability, but a high rake angle helps a cutter slice into this tissue while minimizing deflection of the cutter. Conventional cutter machining techniques generally cannot produce a positive high rake angle cutter, and these cutters generally have a small rake angle (less than about 15 degrees). Additionally, a larger rake angle may decrease the structural integrity of a cutter, which may the cutter more likely to chip or break during use. The cutters described here, however, may allow for the benefits of high rake angle cutting while reducing the risk of cutter malfunction.

The rake angle of the cutter may be modified depending on the nature of the tissue to be cut. For example, a cutter assembly intended to cut hard, calcified occlusive materials having a higher calcium content, may be configured to have a negative rake angle (i.e., the inner face of the cutting blade may slant outward or forward of the cutting edge), which may be well suited for grinding or smashing hardened occlusive materials. It should be appreciated that a given cutting element can be machined to incorporate cutting blades having both positive and negative rake angles or otherwise include combination of both cutting and grinding surfaces. For example, in some variations a cutter may comprise a first cutting element having a plurality of helical flutes, wherein at least one flute has a cutting edge having a positive rake angle and at least one flute has a cutting edge having a negative rake angle. In some of these variations, the helical flutes having cutting edges having a positive rake angle may have a positive rake angle greater than about 20 degrees (e.g., greater than about 40 degrees or about 70°±10°).

Figure 8D:
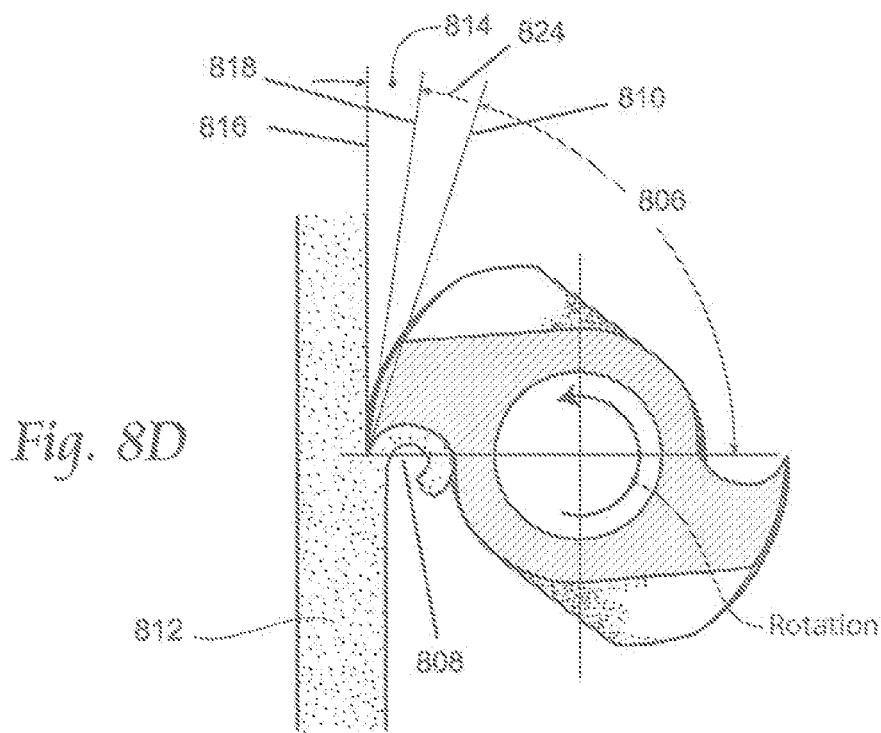
FIG. 8D is a cross-sectional view of the representative cutting element, like that shown in FIG. 8C, cutting into occlusive materials.

In the variation of first cutting element (800) shown in FIGS. 8A-8D, the formation of a flute having a large, positive rake angle (e.g., 70°±10°) may create a cutting blade having an enlarged concave inner face. The enlarged concave inner face may define a trough- or scoop-shaped blade that may efficiently slice through the occlusive materials (812) as shown in FIG. 8D. The large, positive (high) rake angle and resulting enlarged concave inner face of the cutting blade may reduce cutting forces and power requirements for the first cutting element (800) and may remove large volume of occlusive materials with each pass of the cutting blade.

(b) Relief Angle

For each flute, the relief angle (814) can be defined as the angle measured between (i) the tangent (816) drawn from the most radially distant edge (804) of the cutting blade (803) from radius (808) and (ii) the tangent (818) drawn along the outer face of the blade (803). The relief angle generally spans the gap between the cutting edge (804) and the occlusive material (812) surface to be cut (such as shown in FIG. 8D). Generally, a smaller relief angle may form a more tangential interface with a tissue surface during cutting, which may reduce the likelihood that a cutting edge may snag or otherwise catch on tissue during cutting. A larger relief angle may provide more aggressive cutting.

Generally, the relief angle is preferably a small angle less than or equal to about 10° (e.g., between about 0° and about 10°). In some of these variations, the relief angle may be about 0°. In some variations, it may be preferable to have a rake angle of about 70 degrees and a relief angle of about 0 degrees. In other variations, a helical flute may have a rake angle of about 60 degrees and a relief angle of about 10 degrees. The formation of a flute with a small relief angle may create a cutting edge (804) that may make aggressive contact with the occlusive materials (812) such as shown in FIG. 8D. Together with a large positive (high) rake angle, a small relief angle may lead to highly efficient cutting and capture of occlusive materials at the distal end of the cutter assembly, minimizing residue and embolization.

(c) Flute Angle

For each flute, the flute angle (824) can be defined in terms of a relationship with the rake angle and the relief angle, as follows:

Flute Angle=90°−(Rake Angle)−(Relief Angle)

The magnitude of the flute angle is an indication of how thick and sharp the cutting edge is. Given that, in a preferred embodiment, the rake angle may be in a range between about 60° and 80°; the relief angle may be in a range between of about 0° and 10°, the flute angle may be in range between about 0° and about 30°. Maximizing the rake angle and minimizing the relief angle to achieve efficient cutting conditions may result in a cutter geometry having a reduced flute angle. Accordingly, it may be desirable that the first cutting element be machined from a hard metallic material to include at a cutting edge that is a sharp as possible. In some variations, is may also be desirable to coat the cutting blade with a biocompatible, highly lubricious material with a low coefficient of friction (preferably no greater than 0.5) to help keep the cutting blade sharp during use. In these variations, coating materials such as titanium nitride or diamond-like carbon (DLC) may be used.

(d) Helix Angle

In the variation of the first cutting element (800) shown in FIGS. 8A-8D, each flute (802) of the first cutting element (800) may comprise a helical cut. The helix angle (826) may be defined as the angle between (i) the rotational axis (828) of the cutting blade (803) and (ii) a tangent (830) drawn along the inner face the cutting blade (803). The magnitude of the helix angle is indicative of the capability of the cutting blade to transport cut occlusive material proximally along the cutting blade and into the housing.

In some variations, each flute (802) of the first cutting element (800) may have a helix angle (802) between about 30° and 60°. A helix angle below 30° may increase the likelihood the first cutting element (800) may overload with occlusive material and stall, while a helix angle above 60° may diminish the cutting efficiency of the first cutting element (800).

(ii) The Second Cutting Element

As mentioned above, the cutter assembly may comprise a second cutting element. For example, in the variation of atherectomy apparatus (500) shown in FIGS. 5A and 5B, the cutter assembly (506) may comprise a second cutting element (514). In variations that include a second cutting element, the second cutting element may be machined from a hard metallic material (e.g., 17-4 stainless) to include helical cutting flutes. The cutting flutes may be configured to have the same rake angle, relief angle, flute angle, and helix angle as the flutes of the first cutting element. In some variations, the above-mentioned geometries of the first and second cutting elements may be identical, except that the second cutting element has more flutes than the first cutting element. In some of these variations, the second cutting element may have double the number of flutes of the first cutting element; that is, four flutes are shown.

Figure 9:
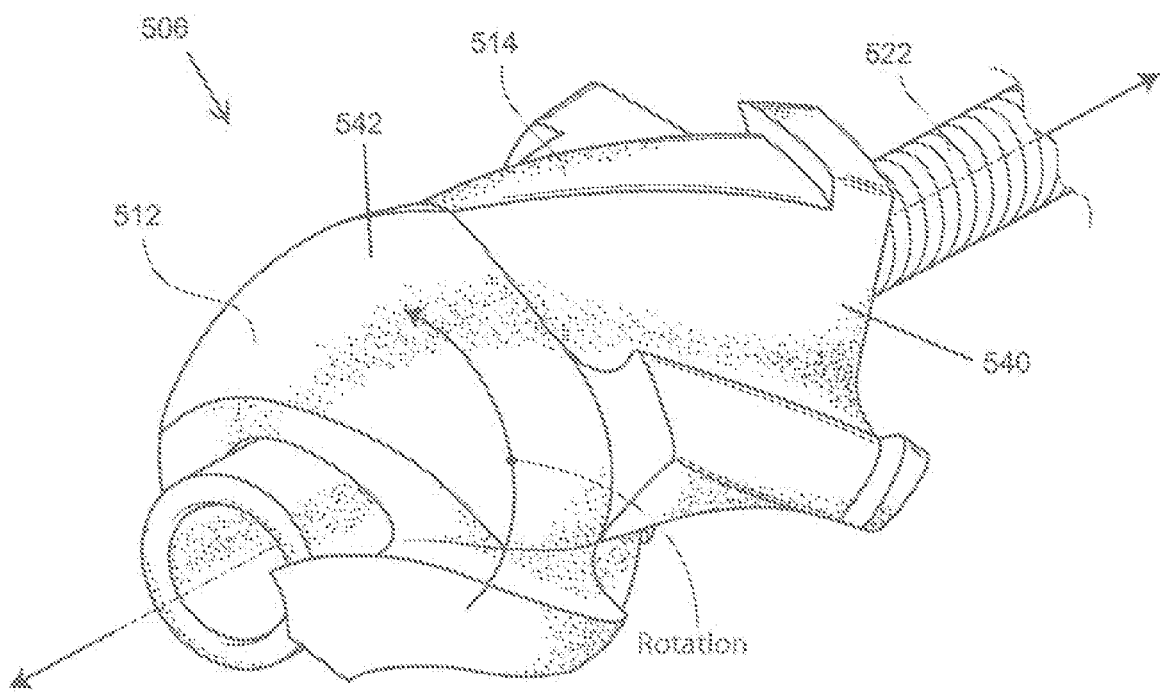
FIG. 9 depicts a distal perspective view of a variation of a cutter comprising first and second cutting elements.

In some variations, the second cutting element is machined to include a hollow stem that fits within a center journal of the first cutting element. For example, in the variation of the atherectomy apparatus shown in FIGS. 5A and 5B, the second cutting element (514) may include a stem (538) around which the first cutting element (512) can be placed. For example, FIG. 9 shows a perspective view of cutter assembly (506), in which the first (512) and second (514) cutting elements may be joined together (e.g., by adhesive or welding) in a rotationally aligned condition. In the aligned condition, two opposing cutting flutes (540) of the second cutting element (514) may be rotationally aligned with the two opposing cutting flutes (542) of the first cutting element (512). Their geometries may be matched during machining, and may act to cut and conveyed occlusive material proximally by the first cutting element into the housing and further convey the occlusive material more proximally into contact with the additional cutting blades of the second cutting element.

(iii) Two-Stage Cutting Action

The cutter assembly (506) shown in FIG. 9 may provide a two-stage cutting action. Generally, the first cutting element (512) may cut occlusive material and convey the material to the second cutting element (514). The second cutting element (514) may further cut or macerate the occlusive materials into smaller particles. During both cutting actions, the occlusive materials may be continuously captured within the housing and conveyed proximally away from the targeted intravascular site. When the first and second cutter elements rotate, the helical cutting surfaces formed by the flutes may cut occlusive materials in the blood vessel and may convey the occlusive material from the blood vessel into the housing through the action of the helical flutes, and may do so without the assistance of any vacuum aspiration.

4. Machining the Cutting Elements

Figure 10:
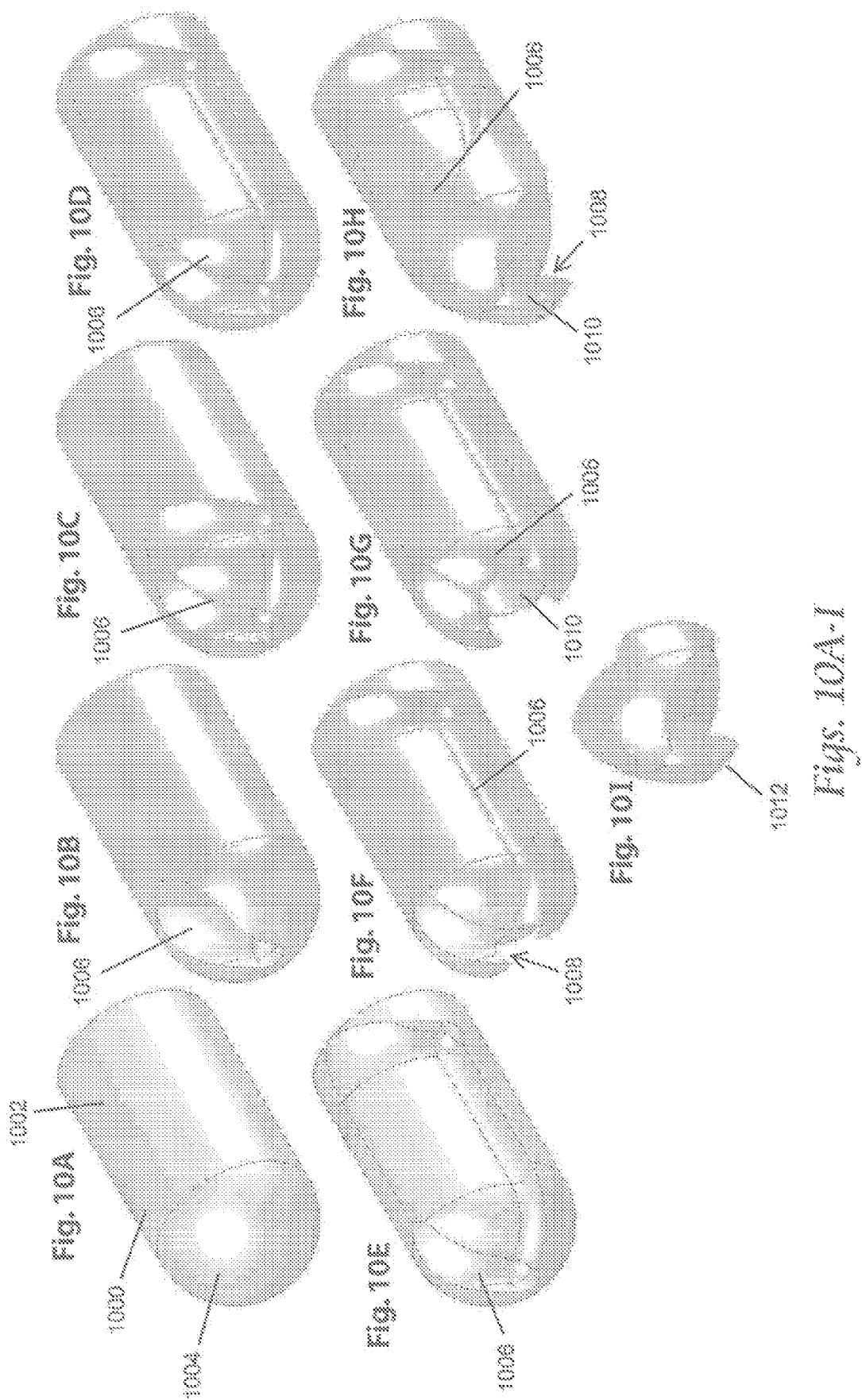
FIGS. 10A-10I depict an illustrative method of machining a variation of the cutting elements described here.

The cutting elements described above may be machined in any suitable manner. For example, FIGS. 10A-10I show an example of method by which a variation of a first cutting element as described above may be machined. Specifically, in these variations first cutting element may be formed from a metal blank (1000). As shown in FIG. 10A, the metal blank (1000) may comprise a cylindrical portion (1002) and a hemispherical portion (1004) extending therefrom. While shown in FIG. 10A as having a hemispherical portion (1004), it should be appreciated that the distal end of the metal blank (1000) may have any suitable outer profile (e.g., egg-shaped or the like). A ball mill (not shown) may be used to begin forming a flute (1006), as shown in FIG. 10B (as will be described in more detail below with respect to FIG. 11). The ball mill may continue to remove material in a circular arc in the hemispherical portion (1004), as shown in FIG. 10C, and then may be drawn proximally along the cylindrical portion (1002) to extend the flute, as shown in FIG. 10D. The ball mill may then exit the blank, as shown in FIG. 10E. The blank (1000) may then be indexed, and a second flute (1008) (as shown in FIG. 10F) may be formed in the same manner as described immediately above. A center index (1010) may then be formed down the center of the blank (1000), as shown in FIG. 10G, which may allow the first cutter to engage with a stem of a second cutting element such as described above. Once the flutes have been cut from the blank (1000), a proximal portion of the blank (1000) may be removed to provide the formed first cutting element (1012), as shown in FIG. 10I.

In some variations, the first (1006) and second (1008) flutes may be milled with a flute helix angle, as shown in FIG. 10H. In these variations, the first (1006) and second flute (1008) may be formed in the same sequence as shown in FIG. 10B-10G, except that the metal blank (1000) is rotated around the longitudinal axis of the metal blank (1000) during formation of the first (1006) and second (1008). The flute helix angle may be any suitable angle, such as described in more detail above.

Figure 11:
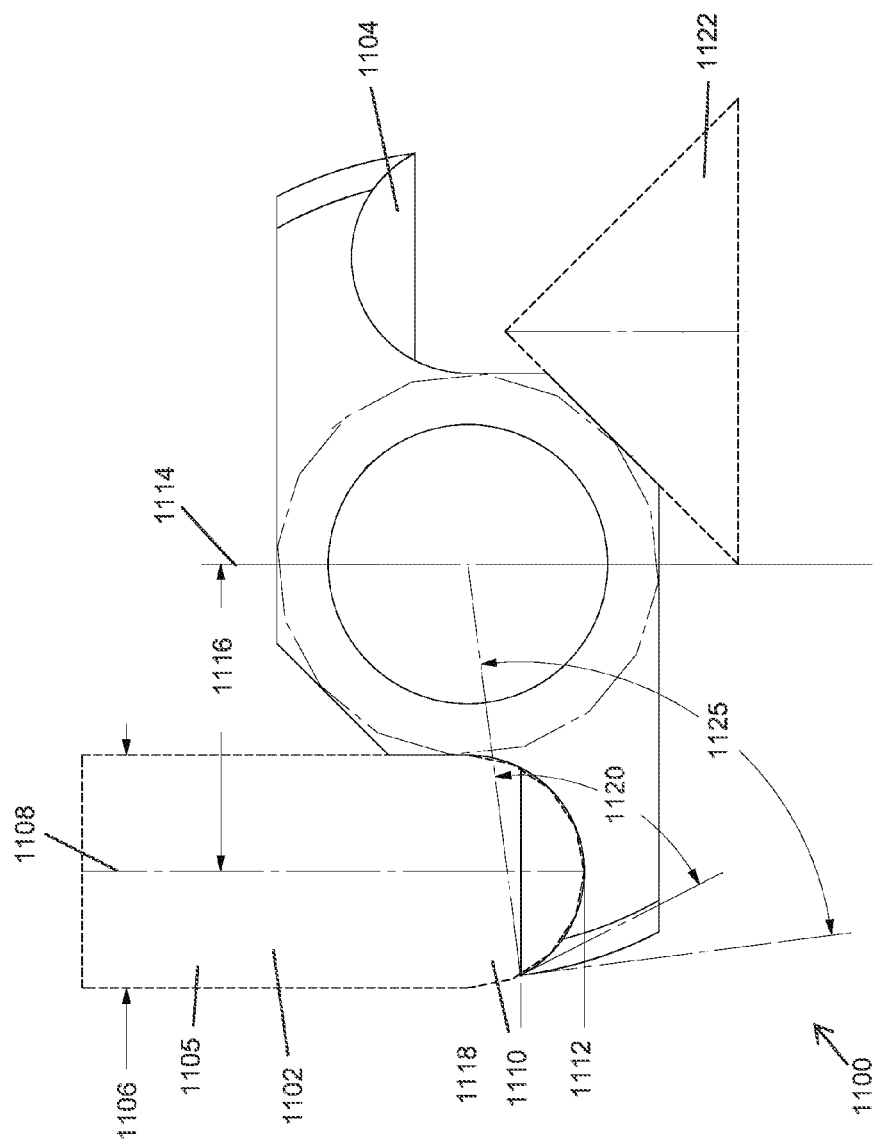
FIG. 11 shows a bottom view of a variation of the cutting elements described here.

FIG. 11 shows a bottom view of a variation of a first cutting element (1100) in which a ball mill (1102) may be used to form one or more cutting flutes (1104). The dimensions and relative positioning of the first cutting element (1100) and ball mill (1102) may control one or more characteristics of the cutting flutes (1104). For example, the ball mill (1102) may have a cylindrical portion (1105) having a diameter (1106) and a longitudinal axis (1108), and a hemispherical portion (1110) having a radius (1112). When the ball mill (1102) is initially introduced into cutting element (1100) (such as described above with respect to FIG. 10B), the ball mill (1102) may be advanced such that the longitudinal axis of the ball mill (1108) is advanced along a centerline (1114) that intersects with the center of the first cutting element (and in some variations may be perpendicular to the longitudinal axis of the blank). The ball mill (1102) may be advanced along the centerline (1114) until the ball mill forms the desired rake angle, and forms an initial cut such as shown in FIG. 10B. In some variations, the ball mill (1102) may be configured such that the desired rake angle is formed when the cylindrical portion (1105) of ball mill reaches a line (1118) which perpendicularly intersects the centerline (1114) at the center of the first cutting element (1100).

The ball mill (1102) may be moved in an arc relative to the first cutting element (1100), to extend the cut formed by the ball mill (1102) until the longitudinal axis (1108) of the ball mill (1102) is positioned a distance (1116) away from the centerline (1114), as shown in FIG. 11. When the ball mill (1102) moves in the arc to the position shown in FIG. 11, the ball mill (1102) may form a cut as shown in FIG. 10C. In some variations where the blank comprises a hemispherical end portion, the ball mill (1102) may move in an arc having a radius equal to the distance (1116). Additionally, as the ball mill (1102) moves along this arc, the longitudinal axis (1108) of the ball mill (1102) may remain parallel with the centerline (1114). As shown in FIG. 11, the ball mill (1102) may form a cutting flue (1104) having rake angle (1120) and a relief angle (1125). For example, in the variation shown in FIG. 11, the rake angle (1120) may be about 70 degrees, and the relief angle may be about 90 degrees.

The ball mill (1102) may be moved distally (e.g., parallel to the longitudinal axis) to extend the cutting flutes, such as shown in FIG. 10D. In some variations, as the ball mill (1102) is moved relative to cutting element (1100) in this way, the distance (1116) between the longitudinal axis (1108) of the ball mill (1102) and the centerline (1114) may remain constant. It should be appreciated, however, that in variations where the cutting flute (1104) is formed with a helix angle (as described above with respect to FIG. 10H), the first cutter (1100) may be rotated around the center of the cutter as the ball mill (1102) moves between the various positions described above.

The dimensions described above may varied as necessary to provide a cutting flute (1104) having a desired rake angle (1124). For example, in variations in which the first cutting element (1100) is configured to have a diameter of about 2.4 mm and a rake angle (1120) of about 70 degrees, the ball mill (1102) diameter (1106) and radius (1112) may be about 0.0250 inches and about 0.0125 inches, respectively, and distance (1116) may be about 0.0330 inches. In variations in which the first cutting element (1100) is configured to have a diameter of about 2.2 mm and a rake angle (1120) of about 70 degrees, the ball mill (1102) diameter (1106) and radius (1112) may be about 0.0220 inches and about 0.0110 inches, respectively, and distance (1116) may be about 0.295 inches. In still other variations in which the first cutting element (1100) is configured to have a diameter of about 1.8 mm and a rake angle (1120) of about 70 degrees, the ball mill (1102) diameter (1106) and radius (1112) may be about 0.0130 inches and about 0.0065 inches, respectively, and distance (1116) may be about 0.0252 inches.

Also shown in FIG. 11, a chamfer bit (1122) may be used to remove additional material from the first cutting element (1100) between the cutting flutes (1104). For example, FIGS. 27A-27L show such a variation of a method by which a variation of a first cutting element as described above may be machined. Specifically, in these variations first cutting element may be formed from a metal blank (2700). As shown in FIG. 27A, the metal blank (2700) may comprise a cylindrical portion (2702) and a hemispherical portion (2704) extending therefrom. While shown in FIG. 27A as having a hemispherical portion (2704), it should be appreciated that the distal end of the metal blank (2700) may have any suitable outer profile (e.g., egg-shaped or the like). A ball mill may introduced along a centerline (as described in more detail above with respect to FIG. 11) to begin forming a first flute (2706), as shown in FIG. 27B. The ball mill may be moved in an arc to continue to remove material in a circular arc in the hemispherical portion (2704), as shown in FIG. 27C, and then may be drawn proximally along the cylindrical portion (2702) to extend the flute and form cutting edge (2711), as shown in FIG. 27D. The ball mill may then exit the blank, as shown in FIG. 27E. A chamfer bit (or the like) may then be used to form a first cut (2708) (as shown in FIG. 27F) and a second cut (2710) (as shown in FIG. 27G) to remove additional material from the cutter. The blank (2700) may then be indexed, and a second flute (2712) and second set of cuts (as shown in FIG. 27H) may be formed in the same manner as described immediately above. A chamber bit (or the like) may then be used to reduce the outer diameter of a proximal portion (2714) of the blank (2700) as shown in FIG. 27I, which may reduce the outer diameter of a proximal portion of the cutter (which may provide one or more benefits as described below). A center index (2716) may then be formed down the center of the blank (2700), as shown in FIG. 27J, which may allow the first cutter to engage with a stem of a second cutting element such as described above. Once the flutes have been cut from the blank (2700), a proximal portion of the blank (2700) may be removed to provide the formed first cutting element (2720), as shown in FIG. 27L.

In some variations, the first (2706) and second (2712) flutes may be milled with a flute helix angle, as shown in FIG. 27K. In these variations, the first (2706) and second flute (2712) may be formed in the same sequence as shown in FIG. 27B-27J, except that the metal blank (2700) is rotated around the longitudinal axis of the metal blank (2700) during steps used to form of the first (2706) and second (2712). The flute helix angle may be any suitable angle, such as described in more detail above.

Figure 13:
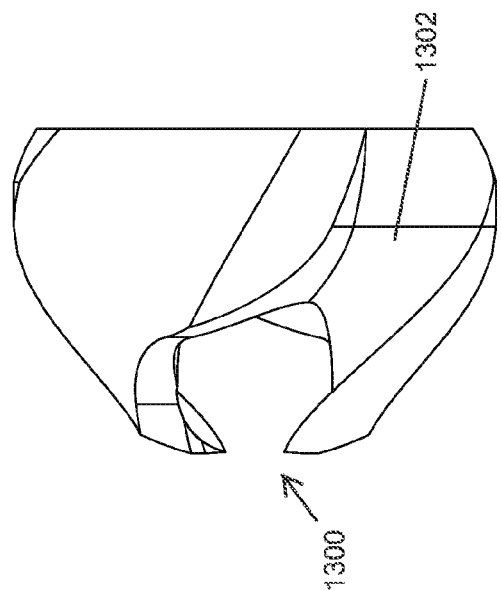
FIGS. 12 and 13 show side views of two variations of cutting elements described here.
Figure 12:
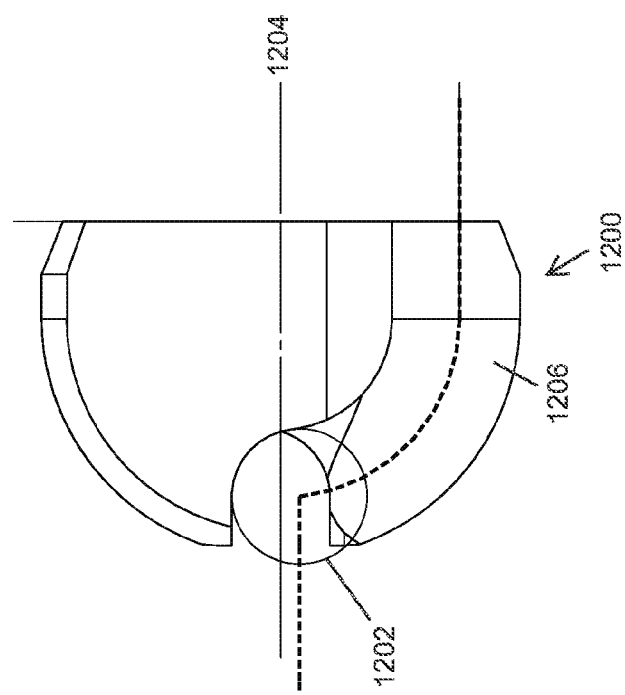

As mentioned above, in some variations a helical path may be milled into the cutting flute, but need not. For example, FIG. 12 shows a side view of a first cutting element (1200) in which the cutting element (1200) is not rotated around the longitudinal axis (1204) relative to a ball mill (1202) during formation of a first cutting flute (1206). Conversely, FIG. 13 shows a side view of another variation of a second cutting element (1300) in which the first cutting element (1300) is rotated during formation of cutting flute (1302) to form a helical pathway. As shown in FIGS. 12 and 13, a proximal segment of the cutting element may be tapered or otherwise reduced in diameter, which may allow for at least a portion of the first cutting element to fit within a cutter housing (not shown) while another portion of the first cutting element may have a diameter greater than or equal to the diameter of the first housing. This may allow the first cutting element to cut a wider path of tissue relative to the cutter housing, and may reduce the frictional load on the cutter housing during advancement of the device.

FIGS. 14A-14C depict perspective, side, and bottom views, respectively, of a variation of second cutting element (1400) such as described above with respect to FIGS. 5A and 5B. FIG. 15 shows a top view of the second cutting element (1400) depicted with a ball mill. As shown in these figures, the second cutting element (1400) may be machined to have a plurality of helical cutting flutes (1402) (in the variation depicted there, the second cutting element (1400) may comprise four flutes, but it should be appreciated that the second cutting element may contain any number of cutting flutes such as described in more detail above), a stem (1404), a journal (1406) extending at least partially within the second cutting element (1400), and a guide wire lumen (1408) extending through the second cutting element (1400) (including the stem (1404)). In some variations, some or all of the cutting flutes (1402) may comprise proximal flanges (1410), which may fit at least partially in a groove (not shown) of a cutter housing (not shown) during rotation of the second cutting element (1400).

The components may have any suitable dimensions. For example, the second cutting element may have a first outer diameter (1412) (including proximal flanges (1410)) and a second outer diameter (1414) (not including proximal flanges (1410)). The stem (1404) may have a height (1416) and an outer diameter (1418). The journal (1406) may have a diameter (1420), and the guide wire lumen (1408) may have a diameter (1422). The cutting flutes (1402) may have a height (1419), and the flanges (1410) may have a height (1420). To form the cutting flutes (1402), a ball mill having a tip radius (1424) may be centered a distance (1426) away from a centerline (1428). These dimensions may be at least partially determined by the desired size of the cutter assembly. It should also be appreciated that the cutting element may be rotated relative to ball mill (1424) during formation of the cutting flutes (1402) to provide a helical pathway of the cutting flutes (1402).

For example, in some variations where the second cutting element (1400) is configured to be used with a 2.4 mm cutter assembly, the first outer diameter (1412) may be about 0.089 inches, the second outer diameter (1414) may be about 0.083 inches, the stem (1404) may have a height (1416) of about 0.064 inches and an outer diameter (1418) of about 0.0298 inches, the diameter (1420) of the journal (1406) may be about 0.037 inches, the diameter (1422) of the guide wire lumen (1408) may be about 0.018 inches. In these variations, the cutting flutes (1402) may have a height (1419) of about 0.049 inches, and the flanges (1410) may have a height of about 0.007 inches. In some of these variations, the ball mill may have a tip radius (1424) of about 0.0250 inches and may be centered away from centerline (1428) by a distance (1426) of about 0.0330 inches.

In some variations where the second cutting element (1400) is configured to be used with a 2.2 mm cutter assembly, the first outer diameter (1412) may be about 0.0805 inches, the second outer diameter (1414) may be about 0.0735 inches, the stem (1404) may have a height (1416) of about 0.058 inches and an outer diameter (1418) of about 0.0275 inches, the diameter (1420) of the journal (1406) may be about 0.035 inches, the diameter (1422) of the guide wire lumen (1408) may be about 0.018 inches. In these variations, the cutting flutes (1402) may have a height (1419) of about 0.49 inches, and the flanges (1410) may have a height of about 0.007 inches. In some of these variations, the ball mill may have a tip radius (1424) of about 0.0220 inches and may be centered away from centerline (1428) by a distance (1426) of about 0.0295 inches.

In some variations where the second cutting element (1400) is configured to be used with a 1.8 mm cutter assembly, the first outer diameter (1412) may be about 0.063 inches, the second outer diameter (1414) may be about 0.057 inches, the stem (1404) may have a height (1416) of about 0.052 inches and an outer diameter (1418) of about 0.0245 inches, the diameter (1420) of the journal (1406) may be about 0.032 inches, the diameter (1422) of the guide wire lumen (1408) may be about 0.018 inches. In these variations, the cutting flutes (1402) may have a height (1418) of about 0.49 inches, and the flanges (1410) may have a height of about 0.007 inches. In some of these variations, the ball mill may have a tip radius (1424) of about 0.0130 inches and may be centered away from centerline (1428) by a distance (1426) of about 0.0252 inches.

D. Mechanical Removal of Occlusive Materials

Figure 17:
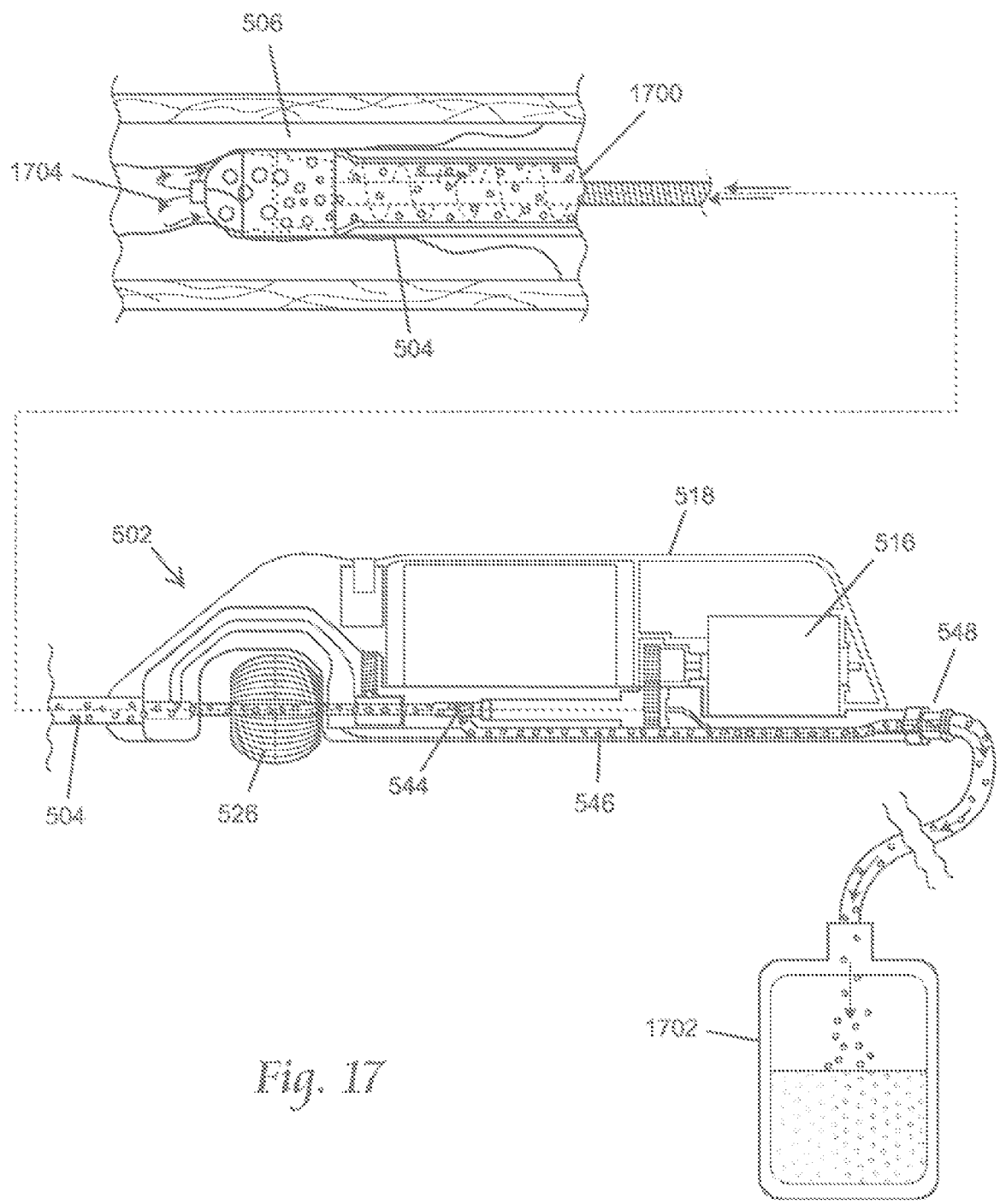
FIG. 17 depicts a cross-sectional side view of a variation of the catheter assemblies described here.

As mentioned above, in some variations of the atherectomy apparatuses described here, the atherectomy apparatus includes an internal conveying member. For example, the variation of atherectomy apparatus (500) shown in FIGS. 5A and 5B may comprise an internal conveyor (524). In variations that include an internal conveying member, the internal conveying member may comprises a wire helically wound about the torque shaft in a direction common with the helical cutting surfaces of the cutter assembly. When a cutter assembly cuts and captures occlusive material (e.g., when the helical flutes of a first and/or second cutting element conveys cut and captured occlusive materials to the conveying member), the conveying member may rotate in common with a torque shaft to convey the cut and captures occlusive materials it receives from the cutter assembly further back (proximally) along the catheter body into the handle. For example, FIG. 17 shows the variation of atherectomy apparatus (500) described above with respect to FIGS. 5A and 5B conveying and transferring occlusive material (1700) proximally through the apparatus.

The occlusive materials carried back by the conveying element into the handle may be transferred into a discharge passage within the handle. A transfer propeller communicating with the discharge passage may be coupled to the torque shaft to rotate in common with the torque shaft, and may act to pump the cut, captured, and conveyed occlusive materials into the discharge passage. The discharge passage may include an external coupler (e.g., a leur connector) to couple the discharge passage to an external waste container. The cut and captured occlusive materials may be conveyed into the waste receptacle, and may be done so without need for vacuum aspiration. For example, as shown in FIG. 17, atherectomy apparatus (500) may comprise a transfer propeller (544), a discharge passage (546), and an external coupler (548), which may be connected to an external waste container (1702) as just described.

In some instances, it may be desirable to convey saline or another biocompatible fluid down the catheter body for mixing with occlusive material within the cutter assembly. Mixing the fluid with the occlusive materials may form a slurry, which may reduce the viscosity of the materials cut, captured, and conveyed from the vessel by the atherectomy apparatus. This may reduce the load imposed on the cutter assembly and facilitate the transfer of materials into the waste receptacle. As shown in FIG. 17, the atherectomy apparatus (500) may convey a fluid (1704) from the distal end of the device. In some variations, the fluid (1704) may be conveyed through an internal/guide wire lumen within the torque shaft (522).

II. Deflectable Atherectomy Systems and Apparatuses

A. Overview

Figure 18A:
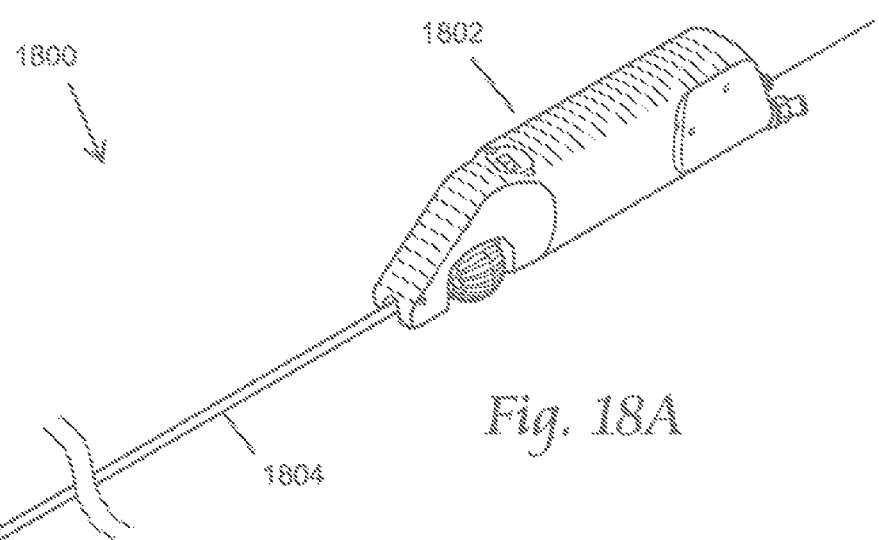
FIG. 18A depicts a perspective view of a variation of the atherectomy systems described here.
Figure 18B:
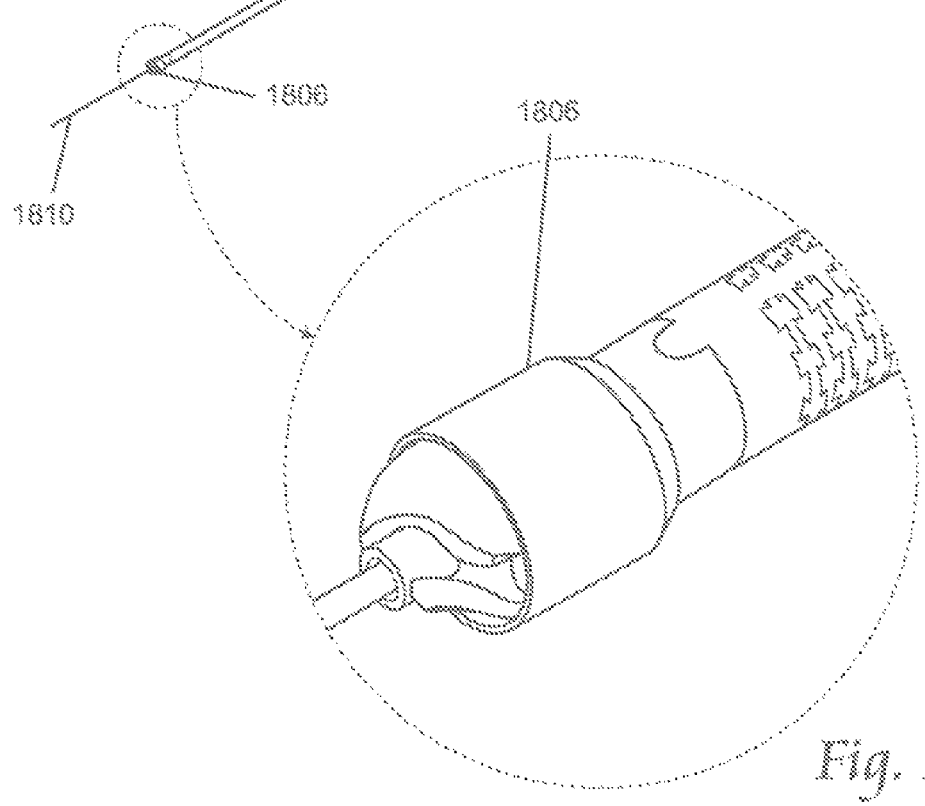
FIG. 18B is an enlarged perspective view of a distal portion of the atherectomy system shown in FIG. 18A.
Figure 18C:
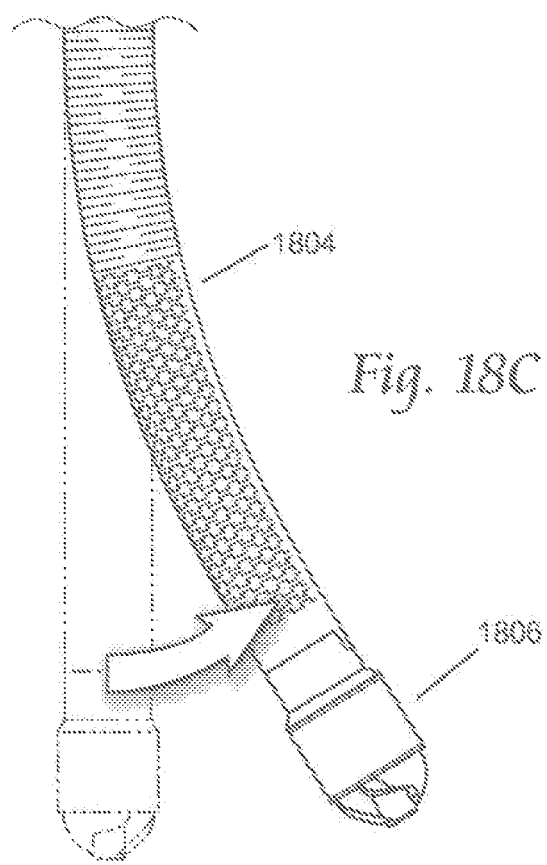
FIGS. 18C and 18D depict different manners in which the atherectomy system as shown in FIG. 18A may be manipulated.
Figure 18D:
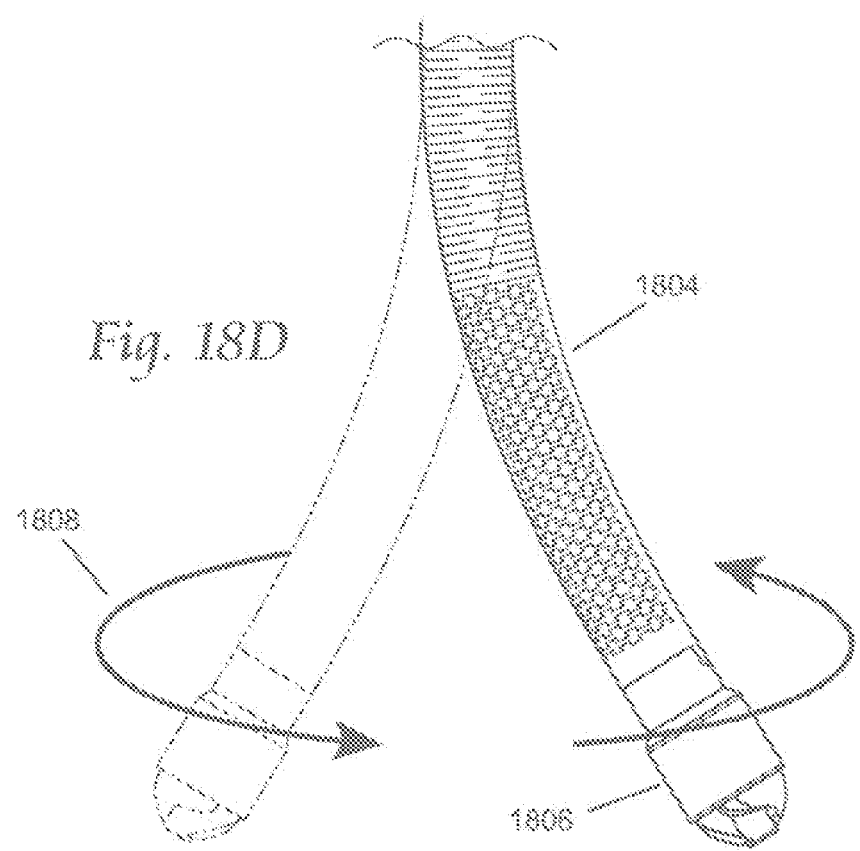

In some variations, the atherectomy systems described here may comprise an atherectomy apparatus configured to selectively dynamically deflect at its distal end (e.g., near a cutter assembly). Additionally, the atherectomy apparatus may be configured to selectively sweep a portion of the atherectomy apparatus, as will described in more detail below. For example, FIGS. 18A-18D show one variation of an atherectomy apparatus (1800) comprising a handle (1802), a catheter body (1804), and cutter assembly (1806). These elements may include any of the features previously described. As will be described in greater detail, the catheter body (1804) may be configured to dynamically deflect at its distal end (where the cutter assembly (1806) is carried) relative the central axis of the proximal catheter body (1804), as shown in FIG. 18C. This deflection may occur without axial advancement of the atherectomy apparatus. Additionally, the atherectomy apparatus (1800) may be configured to rotate the distal end of the apparatus while deflected about the central axis of the proximal catheter body (1804) to sweep the cutter assembly (1806) in an arc (1808) around the central axis, as shown in FIG. 18D. The ability of the atherectomy apparatus (1800) to sweep may allow for the cutter assembly to cut occlusive materials in a region larger than the outside diameter of the cutter assembly, as will be described in more detail below.

The atherectomy apparatus (1800) may be used in an atherectomy system including a guide wire (1810), and may be introduced into a blood vessel from an external percutaneous access site such as described previously with respect in FIGS. 4A-4D. The handle (1802) may be sized and configured to be securely held and manipulated by a caregiver outside an intravascular path in a manner previously described to advance the catheter along an intravascular. Image guidance (e.g., CT, radiographic, or guidance mechanisms, or combinations thereof), may be used to aid the caregiver's manipulation.

Figure 20A:
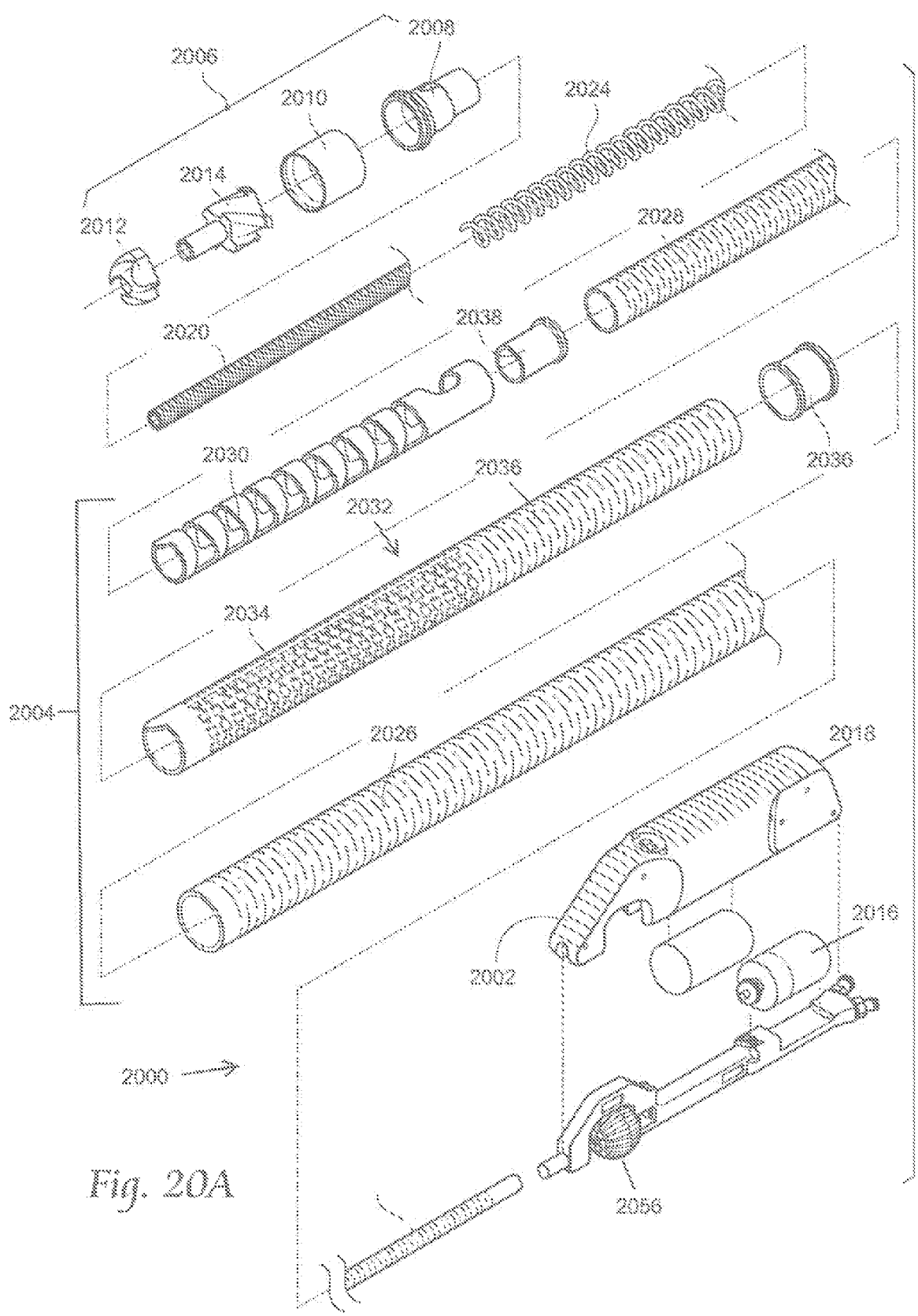
FIG. 20A is an exploded perspective view of a variation of the atherectomy systems described here.
Figure 20B:
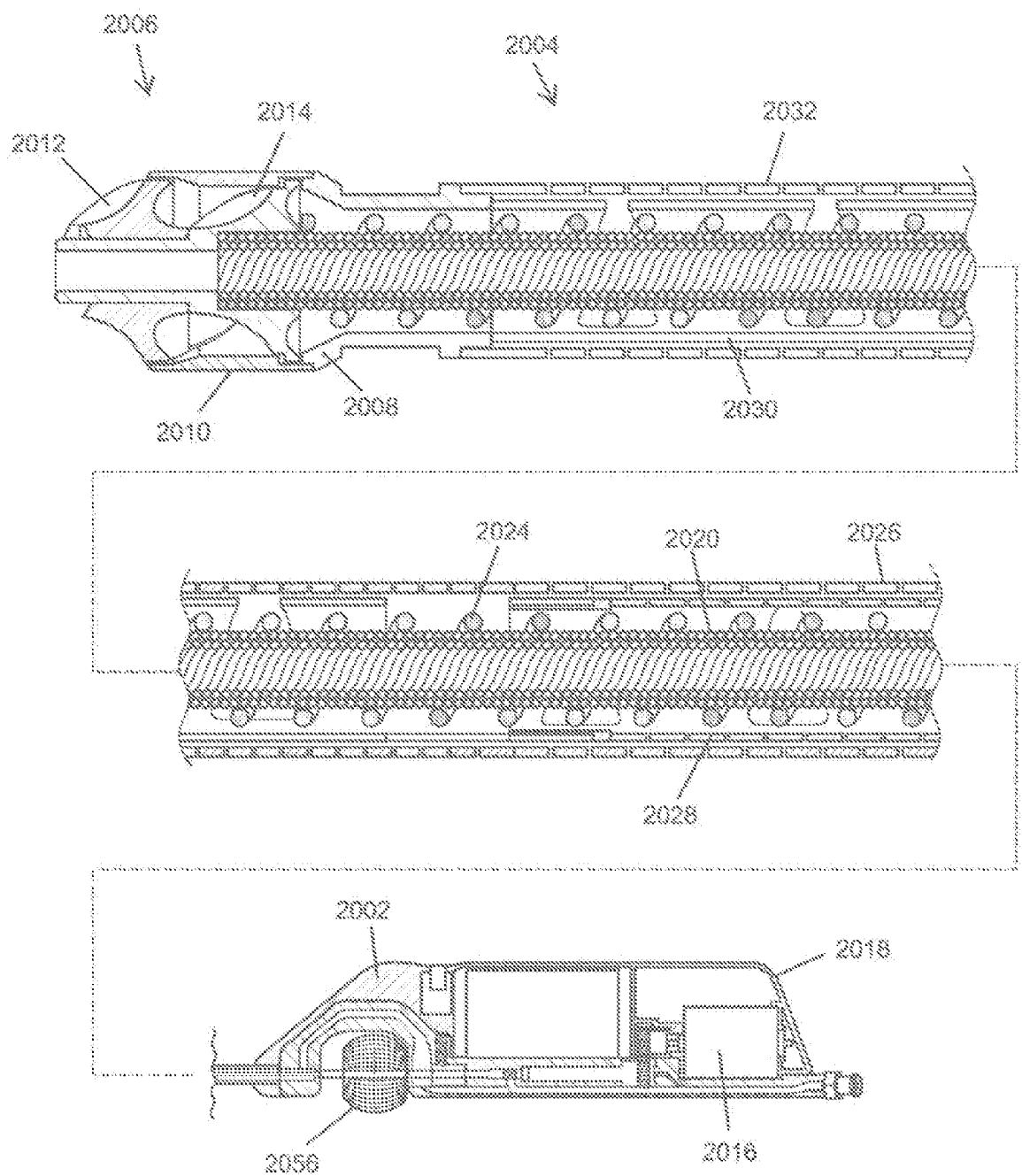
FIG. 20B depicts an assembled cross-sectional side view of the atherectomy system shown in FIG. 20A.

FIGS. 20A and 20B depict a variation of an atherectomy apparatus (2000) configured for use with the atherectomy systems described here. As shown there, atherectomy apparatus (2000) may comprise a handle (2002), a catheter assembly (2004), and a cutter assembly (2006). As shown there, the cutter assembly (2006) may comprise a ferrule (2008), a cutter housing (2010), a first cutting element (2012), and a second cutting element (2014). The cutting assemblies may have any elements or combination of elements as described in more detail above. For example, the cutter housing (2010), first cutting element (2012), and second cutting element (2014) may have any of the elements and dimensions previously described with respect to FIGS. 3A-17. In some variations, the first and second cutting elements may each comprise one or more helical cutting flutes having a rake angle between about 60 degrees and 80 degrees, a rake angle less than or equal to 10 degrees (in some of these variations, about 0 degrees), a flute angle between about 30 degrees and about 0 degrees, and a helix angle between about 30 degrees and about 60 degrees.

Also shown in FIGS. 20A and 20B, the atherectomy apparatus (2000) may further comprise a drive motor (2016), which in some variations may be contained within a housing (2018) of the handle (2002). Also shown there is a torque shaft (2020) which may be coupled by gearing to the motor (2016) at a proximal end of the torque shaft (2020) and coupled to the second cutting element (2014) at a distal end of the torque shaft (2020). The torque shaft rotates the first (2012) and second (2014) cutting elements relative to the cutting assembly, such as described in more detail above. When the cutter rotates, it may cut and convey occlusive materials into the cutter housing (2010), and may do so without the use of any vacuum aspiration.

The atherectomy apparatus (2000) may also further comprise an internal conveyor (2024), which may convey the occlusive materials from the cutter housing (2010) further back (proximally) along the catheter body for discharge outside the patient's body. In these variations, there may be no need for use of a vacuum pump.

B. The Catheter Body

1. Overview

As mentioned previously, the atherectomy apparatus (2000) may comprise a catheter assembly (2004). The catheter assembly may have any suitable dimensions, such as described in more detail above. For example, in some variations, the catheter assembly (2004) may have an outer diameter less than or equal to the outer diameter of the cutter assembly (2006), In some of these variations, the catheter assembly (2004) may have an outer diameter less than the outer diameter of the cutter assembly (2006). In some of these variations, a cutter assembly may have an outer diameter of 2.4 mm, and the catheter assembly may have an outer diameter of 2.2 mm. The catheter assembly may be configured to balance the column stiffness (pushability), tensile stiffness (pullability), torsional stiffness (torquability), and bending stiffness (trackability) of the catheter assembly, such as described in more detail below.

The catheter assembly (2004) may comprise an outer catheter shaft (2026), an inner catheter shaft (2028), and a sweep tube assembly comprising an inner sweep tube (2030) and an outer sweep tube (2032).

2. The Outer Catheter Shaft

The outer catheter shaft (2026) may be formed in any suitable manner. For example, the outer catheter shaft (2026) may be formed from a metal tube (e.g., a 304 stainless steel tube). The outer catheter shaft (2026) may have any suitable dimensions. For example, in some variations it may be desirable for the outer catheter shaft (2026) to be formed from a tube having an outside diameter of about 2.2 mm, a wall thickness of about 0.288 mm, and a length of about 1347 mm (53.03 inches).

As discussed previously, a metal tube with some or all of the dimensions described immediately above may provide a high degree of pushability, pullability, and torquability, the baseline bending stiffness may limit the trackability of the catheter body given the length of the catheter body. Accordingly, in some variations, the bending stiffness of the metal tube may be incrementally modulated along the length of the catheter body by creating zones of cut patterns along at least a portion of the length of the catheter body. The cut patterns may be formed in any suitable manner (e.g., via laser cutting), and the zones may impart a desired profile of bending stiffness over the length of the catheter body. For example, cut pattern zones may be used to incrementally decrease the bending stiffness in a stepwise fashion from proximal end to distal end, to provide a minimum bending stiffness conducive to trackability at the distal end (where trackability is more desirable). The stepwise fashion in which the bending stiffness is decreased may be configured in a manner to help maintain the overall pushability, pullability, and torquability.

Figure 21A:
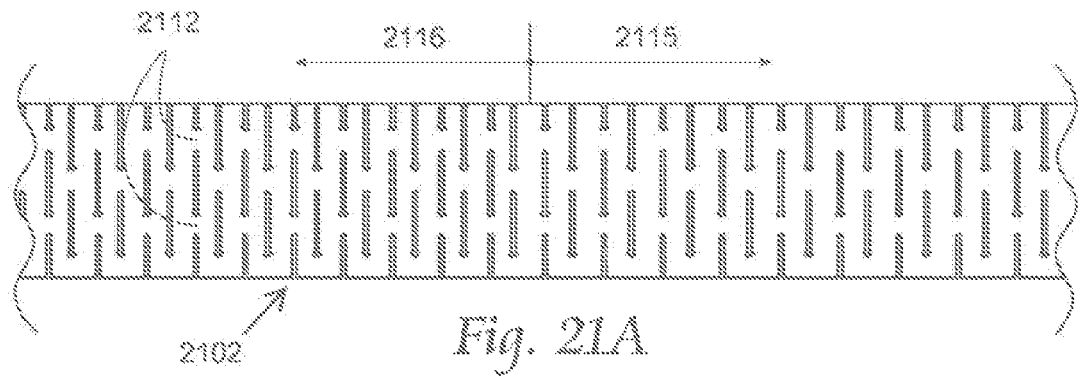
FIG. 21A is a side view of a portion of a variation of a catheter body suitable for use with the atherectomy systems described here.
Figure 21B:
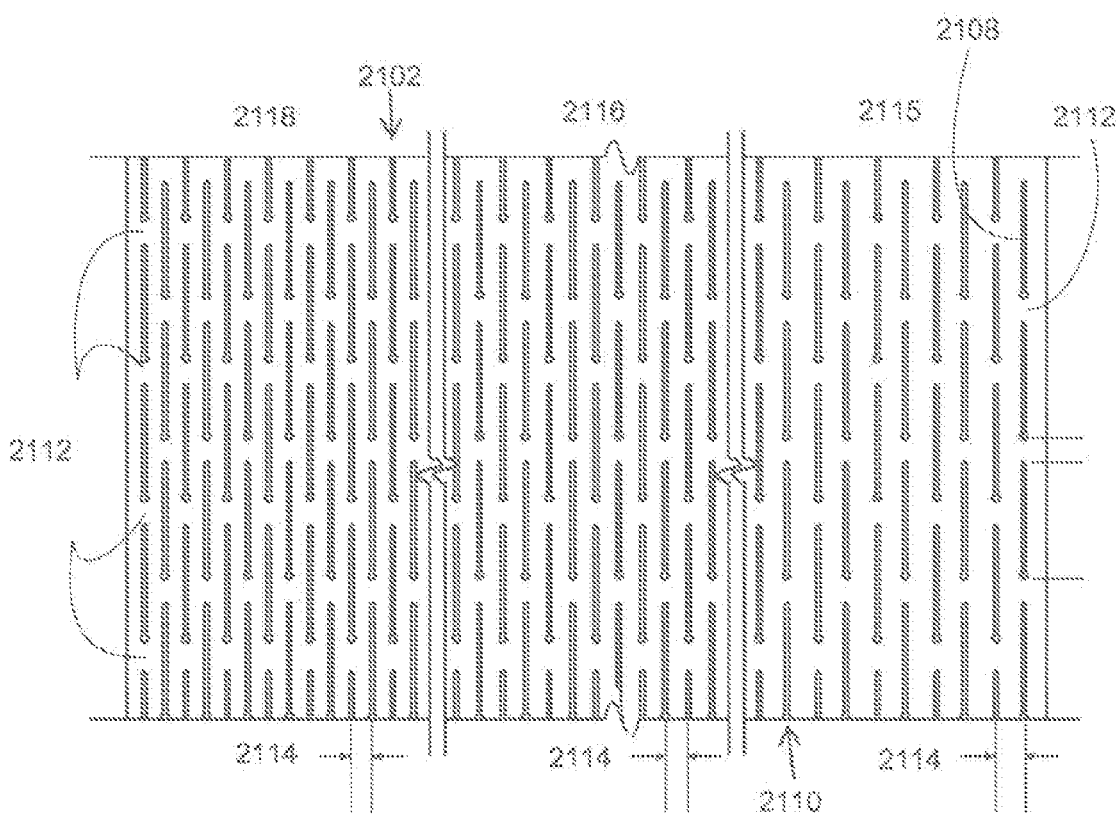
FIG. 21B depicts a plane view of the portion of the catheter body shown in FIG. 21A opened up into a sheet configuration.
Figure 21C:
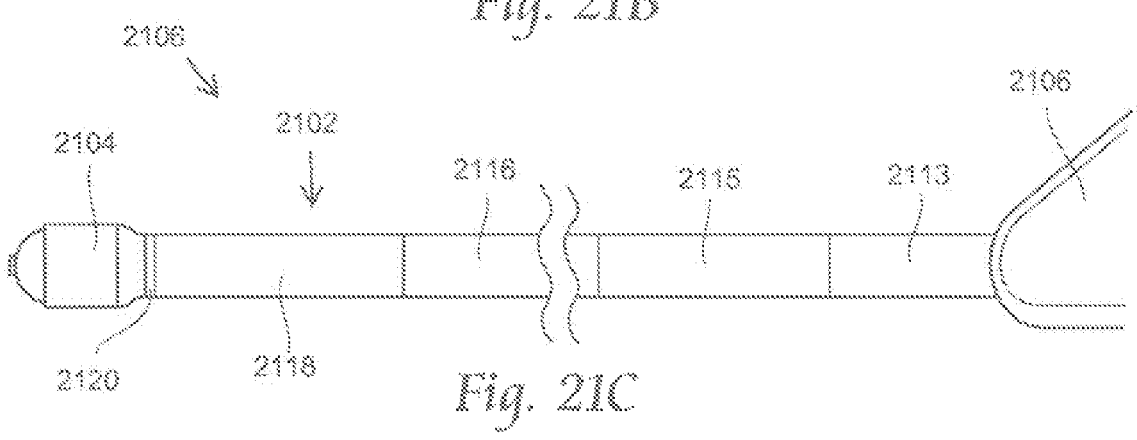
FIG. 21C depicts a side view of an atherectomy apparatus including the catheter body shown in FIGS. 21A and 21B.

For example, FIGS. 21A-21C show one variation of an atherectomy apparatus (2100) comprising a catheter assembly (2102) such as described above with respect to FIGS. 20A and 20B and having an outer catheter body (2103), a cutter assembly (2104), and a handle (2106). Specifically, FIG. 21C shows a side view of the atherectomy apparatus (2100), FIG. 21A shows a side view of multiple sections of the outer catheter body (2103), and FIG. 21B depicts a plane view of a section of the outer catheter body shown opened up into a sheet. As shown there, the outer catheter body (2103) may be formed from a tube and may comprise zones of cut patterns in the form of brickwork cuts (2108) (which may be laser cut) that thread around the longitudinal axis of the outer catheter body (2103). As described above with respect to FIGS. 7A-7C, the brickwork patterns may comprise rows (2110) of brickwork cuts (2108) separated by uncut posts (2112), in which rows (2110) are separated by pitch (2114). In some instances, successive rows (2110) of one or more of the patterns may be offset, and in some instances one or more of the patterns may comprise an alternating brickwork pattern. These patterns may be characterized in terms of the arc of the brickwork cuts (2108), the arc of the posts (2112), the pitch (2114), and the rotational offset between rows (2110).

In the variation shown in FIGS. 21A-21C some of the pattern regions may comprise a pattern having a 75° Cut/15° Uncut alternating brick work cut with a patch that may be in a range between 0.011 inches and 0.014 inches.

The brickwork cut pattern takes away material from the tube, which may reduce the bending stiffness of the tube and may allow the tube/catheter body to bend more easily (thereby increasing trackability). This change in bending stiffness may be at least partially determined by the arc of the brickwork cuts and posts, the pitch between rows, and the offset between rows. The "four-post" brickwork (square) pattern described above with respect to FIGS. 21A-21C may allow for trackability of the catheter body while maintaining pushability, pullability, and torquability. As indicated above, within a given brickwork post pattern, the pitch may be varied (e.g., between 0.011" and 0.014") to affect the bending stiffness. By increasing the pitch, the bending stiffness may be increased, and vice versa.

The catheter bodies may have any number of zones/regions having different cut patterns (or in some zones, no cut pattern at all). For example, in the variation of atherectomy apparatus (2100) shown in FIG. 21C, the outer catheter body (2103) may comprise a first region (2113) extending from the handle (2106), a second region (2115) extending distally from the first region (2113), a third region (2116) extending distally from the second region (2115), a fourth region (2118) extending distally from the third region (2116), and a fifth region (2120) extending distally from the fourth region (2118). In some variations each region may have a lower bending stiffness than the regions proximal to that region. In other variations, each region except the distal-most region may have a lower bending stiffness that the regions distal to that region. Additionally, while shown in FIG. 21C as having five regions, it should be appreciated that the catheter bodies may include any number of regions (e.g., one, two, three, four, five, or six or more), and some or all of the regions may include a cut pattern such as those described here. For example, Table 3 includes one variation of cut patterns that may be utilized with a five-region outer catheter body (2102) shown in FIGS. 21A-21C:

TABLE 3

| Region | Axial Length | Square Cut Pattern (Brickwork) | Pitch |
| --- | --- | --- | --- |
| 1 (Most Proximal) | 1.181" | Uncut | N/A |
| 2 | 17.0" | 75° Cut 15° Uncut | 0.014" |
| 3 | 22.0" | 75° Cut 15° Uncut | 0.012" |
| 4 | 12.9" | 75° Cut 15° Uncut | 0.011" |
| 5 (Most Distal) | 0.10" | Uncut | N/A |

As mentioned above, the outer catheter shaft can be lined or jacketed with a polymeric material, and further may be treated to produce hydrophilic, hydrophobic, or drug binding (heparin, antimicrobial) properties.

3. The Sweep Tube Assembly

As mentioned above, the catheter assembly (2004) shown above in FIGS. 20A and 20B may comprise a sweep assembly comprising an outer sweep tube (2032) and an inner sweep tube (2030). The outer sweep tube (2032) may be connected to the distal end of the outer catheter shaft (2026) (e.g., via coupler (2036)) at a proximal end of the outer sweep tube (2032), and may be connected to the cutter assembly (2006) at a distal end of the outer sweep tube (2032).

As will be described in greater detail below, within the outer sweep tube (2032), the inner catheter shaft (2028) may be coupled to the proximal end of the inner sweep tube (2030) (e.g., via inner coupler (2038)). Sliding the inner catheter shaft (2028) in a distal direction may cause the inner sweep tube (2030) to preferentially bend away from the center axis, thereby preferentially deflecting the cutter assembly toward a side wall of the vessel.

Figure 22A:
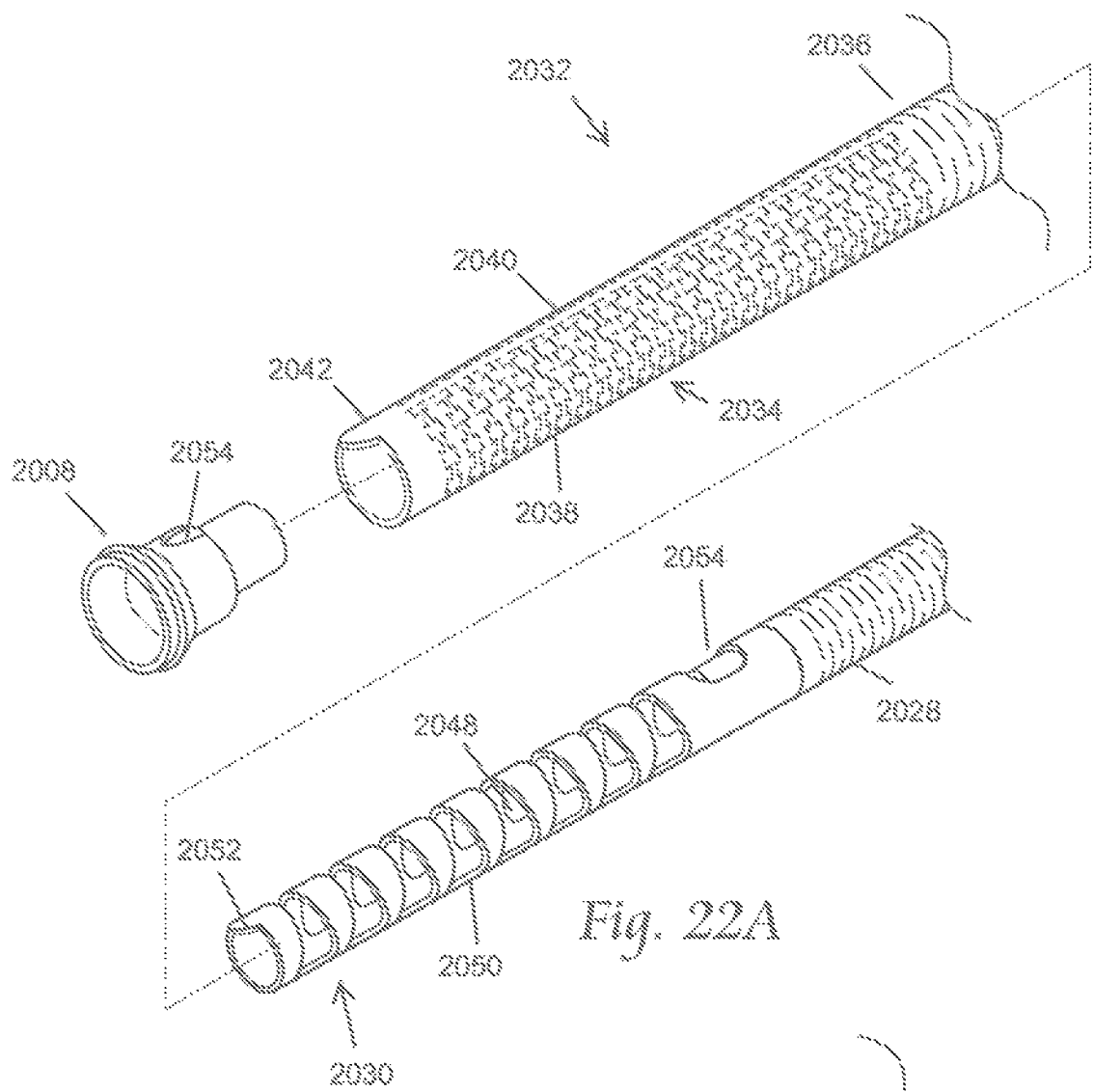
FIG. 22A is an exploded perspective view of a portion of the atherectomy system of FIGS. 20A and 20B.
Figure 22B:
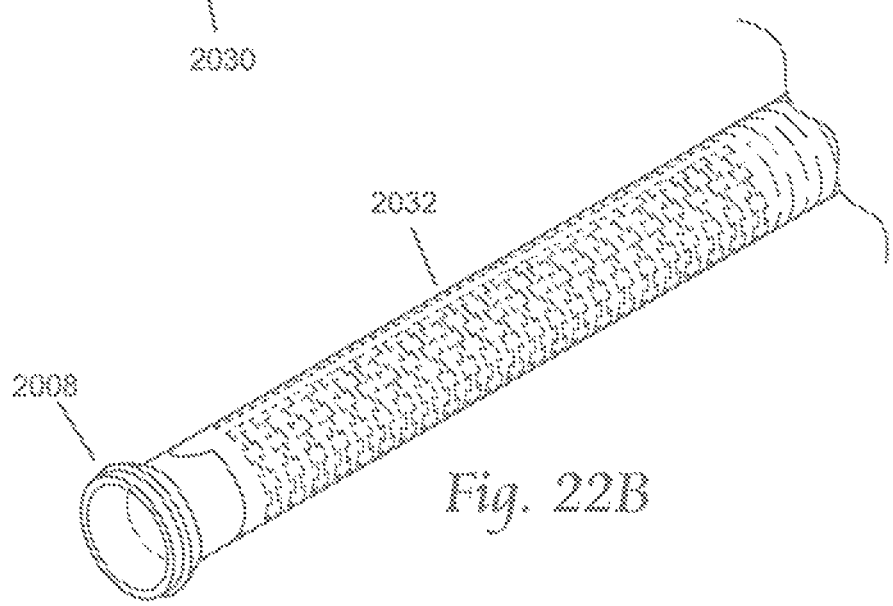
FIG. 22B depicts an assembled perspective view of the components depicted in FIG. 22A.

FIGS. 22A and 22B show an exploded and an assembled view, respectively, of a distal portion of the sweep tube assembly of the catheter assembly (2004) of FIGS. 20A and 20B. As will be described in greater detail, the outer and inner sweep tubes may be mutually sized, configured, and assembled to permit preferential bending of the deflectable assemblage in only a single direction.

(a) The Outer Sweep Tube

The outer sweep tube (2032) may be formed from a metal tube (e.g., 304 stainless steel). As mentioned above the outer sweep tube (2032) may have a distal sweep portion (2034) and a proximal post portion (2036). The distal sweep portion (2034) and the proximal post portion (2036) may be formed from a single tube, or may be formed separately and joined (e.g., by spot welding). The distal sweep portion (2034) and proximal post portion (2036) may have any suitable lengths. In some variations, the distal sweep portion (2034) may have an axial length of about 0.450 inches and the proximal post portion (2036) may have an axial length of about 0.400 inches.

In some variations, the proximal post portion (2036) may comprise a cut pattern (such as one or more of the patterns described above) to decrease the bending stiffness of the proximal post portion (2036). In some of these variations, the proximal post portion (2036) may comprise a 135° cut/45° uncut alternating brickwork pattern with a pitch of about 0.12 inches. The highly flexible nature of such a two-post pattern may provide a flexible transition between the outer catheter body (2026) and the distal sweep portion (2034) of the outer sweep tube (2032).

The distal sweep portion (2034), conversely, may be configured to impart a preferential bending property in a predetermined direction. In some variations, the distal sweep portion (2034) may comprise a pattern of closed, interlocking cuts (which may be laser cut). In the variation shown in FIGS. 20A, 20B, and 22A-22D, the closed, interlocking cuts (2038) may extend in rows that extend around a majority of the circumference (e.g., 350°) of the outer sweep tube, which may leaving a spine (2040) of uncut material (e.g., about 10° of uncut material) that extends axially along the distal sweep portion (2034).

In some variations, the interlocking cuts (2038) may comprise chamfered dovetail cuts. These cuts may provide a plurality of rows of material extending from the spine (2040). The rows (which may have an maximum uncut length of 0.25" each) may be separated by about 0.007 inches of chamfered, dovetail cuts (at 67.4°). The interlocking cuts (2038) may have any number of dovetail cuts (e.g., twelve dovetail cuts along the circumference in each row). In some variations, the distal sweep portion (2034) may include with a proximal uncut region (adjacent the proximal post portion (2036), which may be about 0.01 inches in length) and a distal uncut region (adjacent the cutter assembly, which may be between about 0.025 inches to 0.35 inches). Additionally, in some variations a tab (2042) of uncut material may extend beyond the distal end in alignment with the spine (2040), which may form an outer tube alignment key, as will be described in greater detail later.

The laser-formed pattern of closed, interlocking cuts as just described may resist bending in any direction except in the direction of the spine (2040). When a bending force is applied, the interlocking cuts open to permit the bending to occur in the direction of the spine. Bending force in any other direction may be resisted, as the interlocking cuts are closed to resist bending in these directions.

(b) The Inner Sweep Tube

The inner sweep tube (2030) may be fabricated from a metal tube formed (e.g., nitinol). The inner sweep tube (2030) may extend axially within the outer sweep tube (2032) and may have any suitable dimensions. For example, in some variations the inner sweep tube (2030) may have an outer diameter of about 0.068 inches and an inner diameter of about 0.058 inches, and may have a total axial length of about 0.700 inches±0.005 inches.

In some variations, the baseline bending stiffness of the inner sweep tube (2030) may be reduced to impart a preferential bending property in a predetermined direction. In some of these variations, preferential bending may be created using a pattern of open, dovetail cuts (2048). In the variation shown in FIGS. 20A, 20B, and 22A-22D, the closed, open, dovetail cuts (2048) may extend around a majority of the circumference (e.g., 350°) of the inner sweep tube (2030), which may leaving a spine (2050) of uncut material (e.g., about 10° of uncut material) that extends axially along the inner sweep tube (2030). As shown in FIG. 22A, the spine (2040) of the outer sweep tube (2032) and the spine (2050) of the inner sweep tube (2030) may be aligned such that spine (2040) and spine (2050) may be positioned on opposite sides of the catheter assembly.

The dovetail cuts (2048) may have any suitable dimensions. For example, in some variations the dovetail cuts (2048) each extend about 0.55 inches along the axis of the inner sweep tube (2030), and may include any number of dovetail cuts (2048). In some of these variations, the inner sweep tube (2030) may comprise eight dovetail cuts, which may extend about 0.60" along the spine (2050). Additionally, in some variations a tab (2052) of uncut material may extend beyond the distal end in alignment with the spine (2050), which may form an inner tube alignment key, as will be described in greater detail later.

The laser-formed pattern of open cuts as just described permit preferential bending in the direction of the open cuts, away from the spine, until the open cuts come together and interfere in a distal to proximal succession. When a bending force is applied thereto, the open cuts may permit bending, but, as the bending continues, may resist bending as cuts close and interfere. A preformed bending radius may thereby be built into the inner sweep tube.

The inner sweep tube is inserted into the outer sweep tube, and the inner (2052) and outer alignment tabs (2042) may be brought into registration (see FIGS. 22A and 22B). The rotationally aligned inner (2052) and outer (2042) tabs may be fitted into an alignment key (2054) on the ferrule (2008) (as shown in FIG. 22B). This fitting may ensure that the inner and outer sweep tubes may be properly aligned, and may also act to prevent relative rotation between the inner and outer sweep tubes. In some variations, and the inner and outer sweep tubes may be fixed to the proximal end of the ferrule (e.g., by welding). As mentioned above (and as shown in FIG. 22A), when the inner (2052) and outer (2042) tabs are rotationally aligned, the spine of the outer sweep tube (2042) may axially aligned with the open cuts (2048) of the inner sweep tube (2030) (i.e., the spine (2050) of the inner sweep tube (2030) may rotationally spaced 180° from the spine (2040) of the outer sweep tube (2032)).

As FIG. 22A also shows, the proximal end of the inner sweep tube (2030) may include includes an open boot region (2054) facing at an angle (e.g., about 90°) from the pattern of open dovetail cuts. The open boot region (2054) may be sized and configured to receive the distal end of the inner catheter shaft. It is the inner catheter shaft that may apply a bending force to the deflecting assemblage, as will be described in greater detail later.

(iii) The Inner Catheter Shaft

The inner catheter shaft (2028) of the atherectomy apparatus (2000) shown in FIGS. 20A and 20B may be sized and configured and fabricated in generally the same manner as any of the catheter bodies previously described (e.g., such as the catheter bodies described above in relation to FIGS. 6A-6C and 7A-7C). For example, the inner catheter shaft (2028) may be formed from a metal tube (e.g., a 304 stainless steel tube), and may have dimensions suitable to allow the inner catheter shaft (2028) to fit within the outer catheter shaft and to accommodate passage of the torque shaft and conveyor element therein. Representative embodiments will be described.

The tube of this material and configuration will provide a baseline column stiffness, tensile stiffness, torsional stiffness, and bending stiffness. In some variations, the bending stiffness of the metal tube may be incrementally modulated along the length of the catheter body by creating zones of cut patterns along at least a portion of the length of the catheter body. The cut patterns may be formed in any suitable manner (e.g., via laser cutting), and the zones may impart a desired profile of bending stiffness over the length of the catheter body. For example, cut pattern zones may be used to incrementally decrease the bending stiffness in a stepwise fashion from proximal end to distal end, to provide a minimum bending stiffness conducive to trackability at the distal end (where trackability is more desirable). The stepwise fashion in which the bending stiffness is decreased may be configured in a manner to help maintain the overall pushability, pullability, and torquability.

Figure 23:
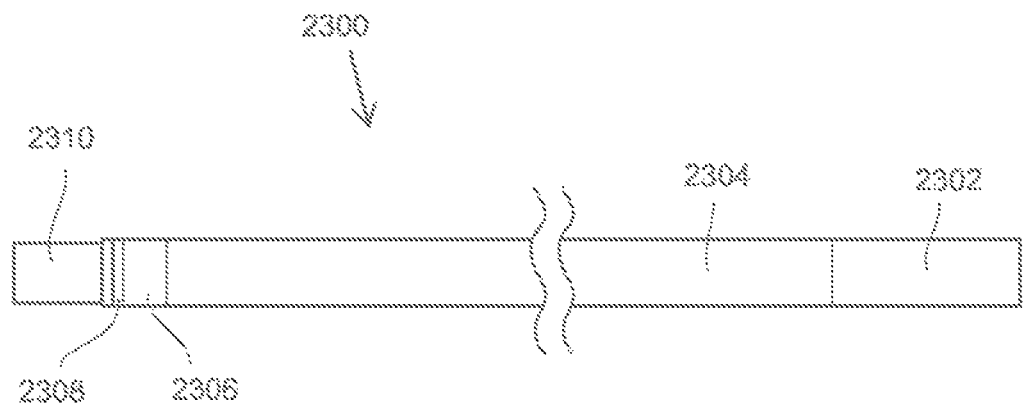
FIGS. 23 and 24 depict side views of representative inner catheter shafts for use with the atherectomy systems described here.

FIG. 23 shows one variation of an inner catheter shaft (2300) which may be used with the atherectomy apparatus (2000) described above with respect to FIGS. 20A and 20B. In some of these variations, the inner catheter shaft (2300) may have an outside diameter of 0.0670"±0.0005", an inside diameter of 0.054"+0.001", and/or an overall length of about 1422 mm±1 mm (i.e., about 56"). As shown in FIG. 23, the inner catheter shaft (2300) may comprise a first region (2302) extending from a handle (not shown), a second region (2304) extending distally from the first region (2302), a third region (2306) extending distally from the second region (2304), and a fourth region (2308) extending distally from the third region (2306). The fourth region (2308) may be connected to a coupler (2310) for connecting the inner catheter shaft (2300) to an inner sweep tube (not shown), as discussed in more detail above. In some variations each region may have a lower bending stiffness than the regions proximal to that region. In other variations, each region except the distal-most region may have a lower bending stiffness than the regions distal to that region. Additionally, while shown in FIG. 23 as having four regions, it should be appreciated that the catheter bodies may include any number of regions (e.g., one, two, three, four, five, or six or more), and some or all of the regions may include a cut pattern such as those described here. For example, Table 4 includes one variation of helical cut patterns that may be utilized with a four-region inner catheter shaft (2300) shown in FIG. 23:

TABLE 4

| Region | Axial Length | Cut Pattern (Right Hand Thread) | Pitch |
| --- | --- | --- | --- |
| 1 (Most Proximal) | 4" | Uncut | N/A |
| 2 | 51" | 100° Cut 30° Uncut | 0.012" |
| 3 | 0.5" | 100° Cut 30° Uncut | 0.008" |
| 4 (Most Distal) | .04" | Uncut | N/A |

The pattern shown in FIG. 23 may impart a high degree of column stiffness to the inner catheter shaft.

Figure 24:
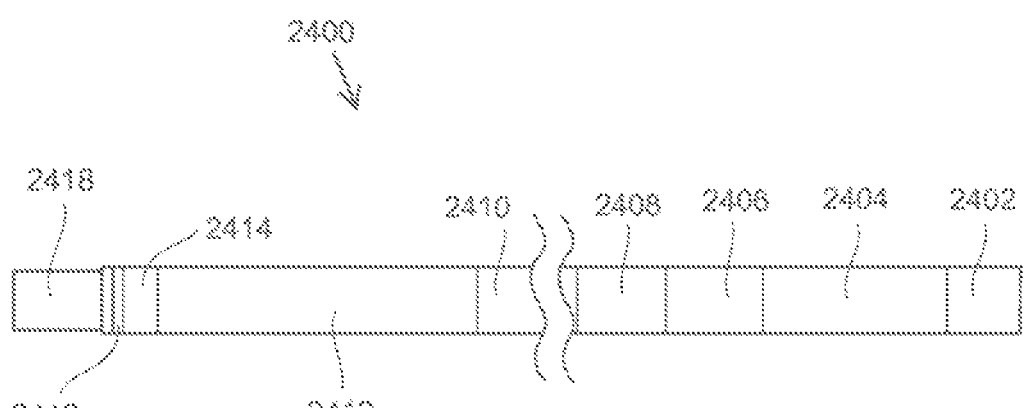

FIG. 24 shows one variation of an inner catheter shaft (2400) which may be used with the atherectomy apparatus (2000) described above with respect to FIGS. 20A and 20B. In some of these variations, the inner catheter shaft (2400) may have an outside diameter of 0.0610"±0.0005", an inside diameter of 0.052"+0.001", and/or an overall length of about 1430 mm±1 mm (i.e., about 56"). As shown in FIG. 23, the inner catheter shaft (2400) may comprise a first region (2402) extending from a handle (not shown), a second region (2404) extending distally from the first region (2402), a third region (2406) extending distally from the second region (2304), and a fourth region (2408) extending distally from the third region (2406), a fifth region (2410) extending distally from the fourth region (2408), a sixth region (2412) extending distally from the fifth region (2410), a seventh region (2414) extending distally from the sixth region (2412), and an eighth region (2416) extending distally from the seventh region (2414). The eighth region (2416) may be connected to a coupler (2418) for connecting the inner catheter shaft (2400) to an inner sweep tube (not shown), as discussed in more detail above. In some variations each region may have a lower bending stiffness than the regions proximal to that region. In other variations, each region except the distal-most region may have a lower bending stiffness than the regions distal to that region. Additionally, while shown in FIG. 24 as having eight regions, it should be appreciated that the catheter bodies may include any number of regions as described in more detail above, and some or all of the regions may include a cut pattern such as those described here. For example, Table 5 includes one variation of helical cut patterns that may be utilized with an eight-region inner catheter shaft (2400) as shown in FIG. 24:

TABLE 5

| Region | Axial Length | Cut Pattern (Right Hand Thread) | Pitch |
| --- | --- | --- | --- |
| 1 (Most Proximal) | 3.789" | Uncut | N/A |
| 2 | 2" | 100° Cut 30° Uncut | 0.016" |
| 3 | 11" | 100° Cut 30° Uncut | 0.015" |
| 4 | 11" | 100° Cut 30° Uncut | 0.014" |
| 5 | 11" | 100° Cut 30° Uncut | 0.013" |
| 6 | 17" | 100° Cut 30° Uncut | 0.012" |
| 7 | .5" | 100° Cut 30° Uncut | 0.008" |
| 8 (Most Distal) | .010" | Uncut | N/A |

The patterns shown in FIG. 24 may impart more flexibility than the patterns shown in FIG. 23.

In some instances, there may be a gap between the inner and outer catheter such shafts, such that flushing fluid that may be conveyed down to the cutter assembly, for mixing with occlusive material within the cutter assembly. Mixing the fluid with the occlusive materials may form a slurry, which may reduce the viscosity of the materials cut, captured, and conveyed from the vessel by the atherectomy apparatus to reduce the load imposed on the cutter assembly and facilitate the transfer of materials into the waste receptacle, as has been previously described. An increased gap may provide a greater volume of fluid to the cutter assembly, which may in turn improve the mechanical conveyance of occlusive materials away from the long total occlusion, thereby reducing the chance of cutter overload and stalling.

(iv) The Mechanism of Deflection and Sweep

The distal end of the inner catheter shaft may be coupled to the inner sweep tube, and may control deflection of the catheter assembly. For example, in the variation of atherectomy apparatus (2000) described above with respect to FIGS. 20A, 20B, 22A and 22B, the inner coupler (2038) may connect the inner catheter shaft (2028) to the inner sweep tube (2030) via the boot region (2054). Generally, the inner coupler (2038) may join the inner catheter shaft (2028) to the boot region (2054) in a manner that may transmit axial compression or tensile forces to the inner sweep tube (2030), but accommodates relative rotation between the inner catheter shaft (2028) and the inner sweep tube (2028) (i.e., the inner catheter shaft does not rotate when the outer catheter shaft is rotated to rotate the inner and outer sweep tubes).

In the situation where the diameter of the inner catheter shaft is reduced to increase the gap dimension between the inner catheter shaft and the outer catheter shaft (as previously described, to accommodate a greater fluid volume), the coupling sleeve may be sized to locally step-up the distal diameter of the reduced diameter inner catheter shaft where it is coupled to the open boot of the inner sweep sleeve (i.e., the inner sweep tube need not be downsized when the inner catheter shaft is downsized), but it should be appreciated that in some instances the diameters of these components may be the same.

The proximal end of the inner catheter shaft may be coupled to a control knob (2056) on the handle (2002). The control knob (2056) may be advanced axially (distally) to advance the inner catheter shaft (2028) against the inner sweep tube (2030), to thereby apply a compressive force (as illustrated by arrow (2058) in FIG. 22D) along the inner catheter shaft (2028) to the inner sweep tube (2030). Being constrained from axial advancement by the ferrule (2008), the inner sweep tube may preferentially deflect in response to the applied compressive force in the direction of the open cut regions (as illustrated by arrow (2060) in FIG. 22D). Likewise, the control knob may be retracted axially (proximally) to relieve the compression force and apply a tensile force to the inner sweep tube, to straighten the delectable assembly, as shown in FIG. 22C.

Figure 22C:
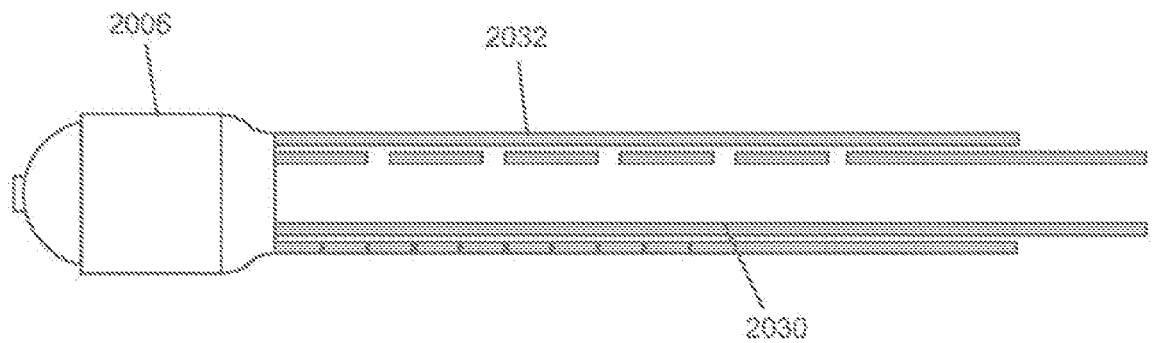
FIGS. 22C and 22D depict a manner in which the atherectomy system shown in FIGS. 20A and 20B may be manipulated.
Figure 22D:
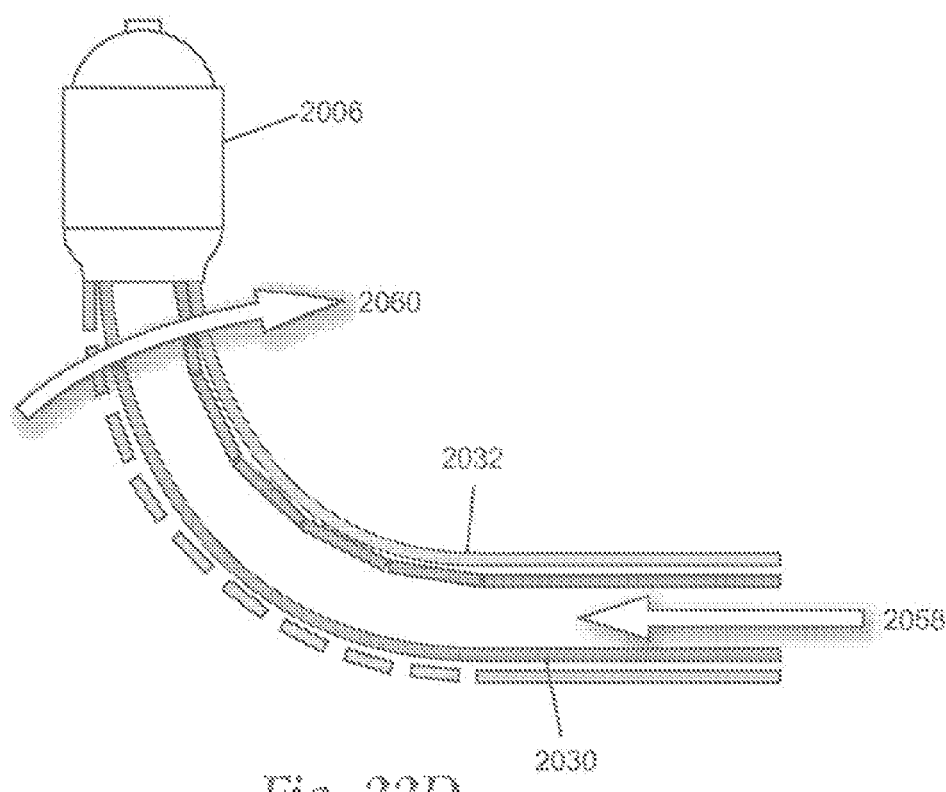

As shown in FIGS. 22C and 22D, with the spine of the inner sweep tube aligned opposite the spine of the outer sweep tube, the preferential bending property of the inner sweep tube (in the direction of the open cuts) may be unified with the preferential bending property of the concentric outer sweep tube (in the direction of the spine, away from the close cuts). The inner sweep tube may progressively bend in response to the bending force imparted by axial advancement of the inner catheter shaft, which may cause the open cuts of the inner sweep tube close and interfere first at the distal end, followed in succession by closing and interference of the proximal cuts down the length of the inner sweep tube. This may form a progressive distal-to-proximal stacking pattern as the inner sweep tube progressively bends until all cuts on the inner sweep tube close and interfere to define the full bend radius (which in some variations may be about 1°). The outer sweep tube may bend in concert with the inner sweep tube, which may open the closed cuts in a distal-to-proximal stacking pattern. The inner and outer sweep tubes may channel the applied bending force in the direction of preferential bending, and may require less bending force for a given angular unit of deflection. Further, the successive distal-to-proximal stacking of the inner sweep tube cuts and opening of the outer sweep tube cuts may result in a uniform column stiffness applied to the cutter assembly regardless of the degree of deflection.

Figure 19A:
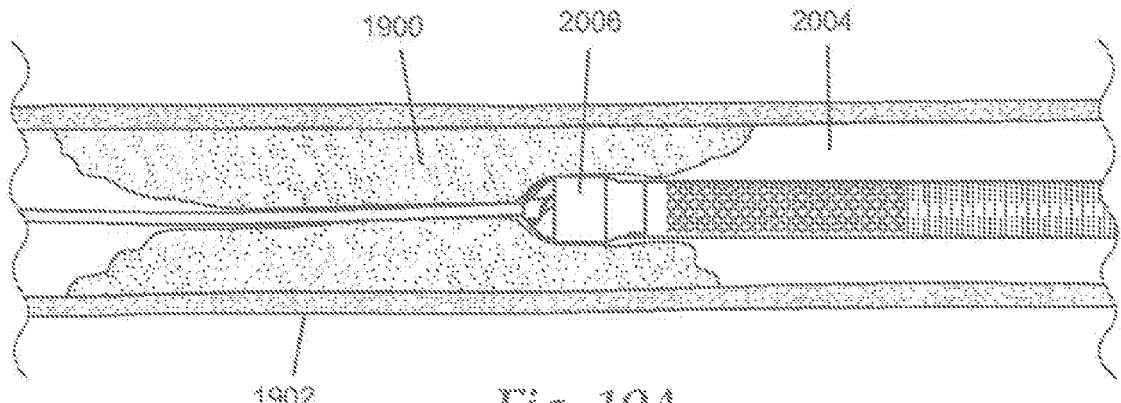
Figure 19B:
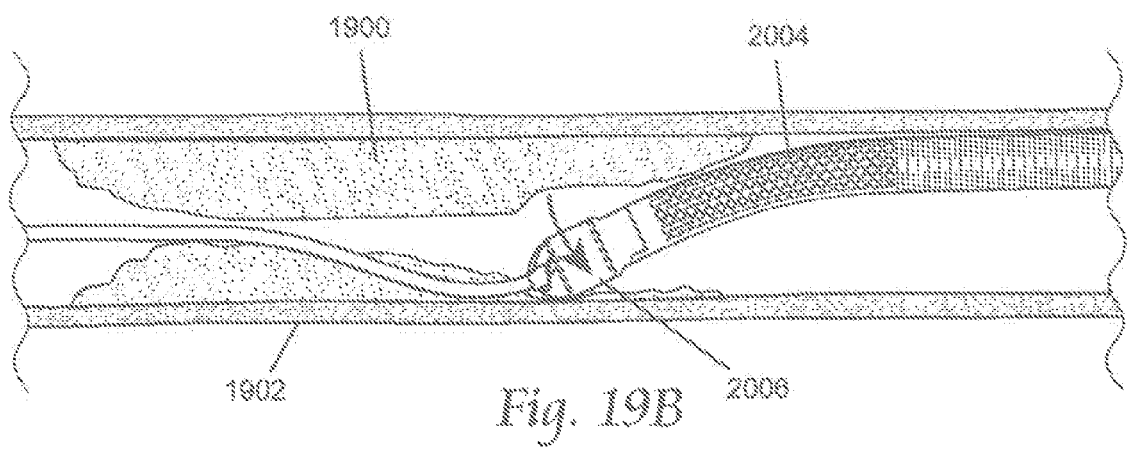
Figure 19C:
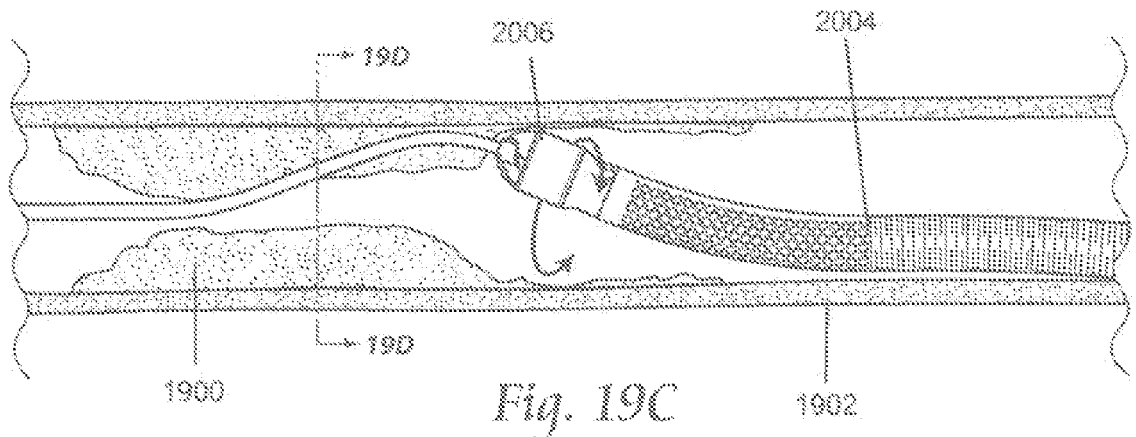

When deflected, the catheter assembly may apply an apposition force upon the cutter assembly, which may be created by opposing contact of the outer catheter assembly against an opposite vessel wall when the cutter assembly (deflected at the end of the catheter) contacts the occlusive materials at a desirable attack angle (as shown FIGS. 19B and 19C). The unified cooperation of the inner and outer sweep tubes during preferential bending may increase the magnitude of the apposition force, and may improve trackability and avoid trauma during advancement over the guide wire.

In some variations, the outer catheter shaft may be coupled to a post on the handle that may be sized and configured to rotate in response to rotation of the control knob (2056). While axial advancement of the control knob (2056) applies compressive force to the inner catheter shaft to deflect the cutter assembly (as described in more detail above), rotation of the control knob (2056) may apply a torque to the outer catheter shaft to rotate the cutter assembly. The cutter assembly may sweep in an arc within the vessel, to clear a diameter of occlusive materials that is greater than the outer diameter of the cutter assembly. It may also be possible to apply torque to the outer catheter shaft by rotating the handle itself. Selective rotation of the cutter assembly can thus be finely controlled by a combination of control knob manipulation and handle twisting.

An indexing mechanism may be provided to provide stepwise control of deflection and/or sweeping, with tactile and/or audible feedback, so that a user may maintain knowledge of the rotational position of the cutter assembly without taking their eye off the radiographic image.

(v) Passive and Active Steering

The enhanced, preferential bending properties of the trackable, deflectable catheter assembly may provide the capability to both actively and passively steer the atherectomy apparatus through tortuous intravascular anatomy. FIGS. 19A-19F(5) depict a manner by which the atherectomy apparatus (2000) described above in relation to FIGS. 20A and 20B may be actively and passively steered within a vessel.

Figure 19D:
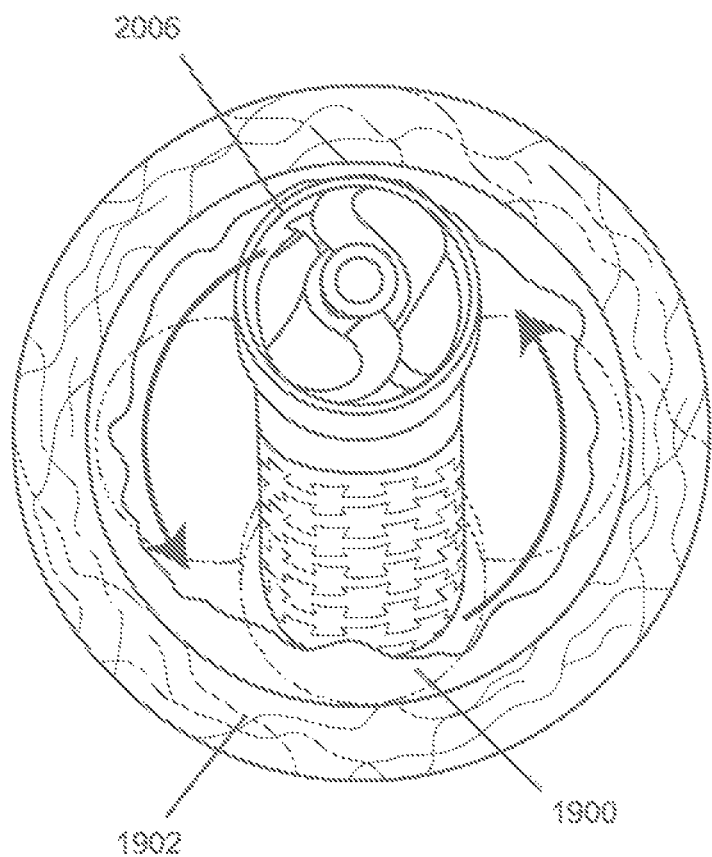
Figure 19E:
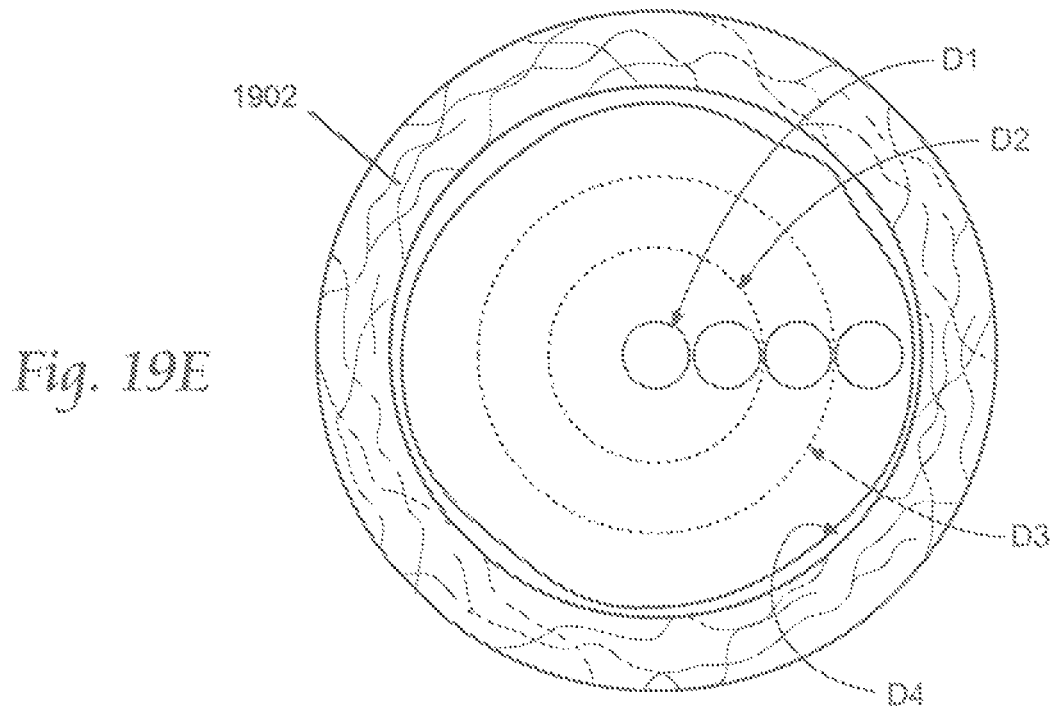

Active steering may be accomplished by advancement of the inner catheter shaft to bend the distal catheter assembly, accompanied by rotation of the catheter assembly, to point the cutter assembly in a preferred direction through an intravascular path, with or without a guide wire, and/or to point the cutter assembly toward a side wall of a vessel, with apposition, to cut and capture occlusive materials. For example, the cutter assembly (2006) of atherectomy apparatus (2000) may be advanced into occlusive material (1900) in a vessel (1902), as shown in FIG. 19A. When in place in the vessel, the catheter assembly (2004) may be deflected as shown in FIG. 19B. The deflected catheter assembly (2004) may be rotated to sweep the cutter assembly (2006), as shown in FIGS. 19C and 19D. This sweep may cause the cutter assembly to move in an arc that is greater than the outer diameter of the cutter assembly. In some variations, the cutter assembly (2006) may cut in a diameter (D2 as shown in FIG. 19E) at least two times the diameter of the cutter assembly (D1 as shown in FIG. 19E). In other variations, the cutter assembly (2006) may cut in a diameter (D3 as shown in FIG. 19E) at least three times the diameter of the cutter assembly. In still other variations, the cutter assembly (2006) may cut in a diameter (D4 as shown in FIG. 19E) at least four times the diameter of the cutter assembly.

Figure 1:
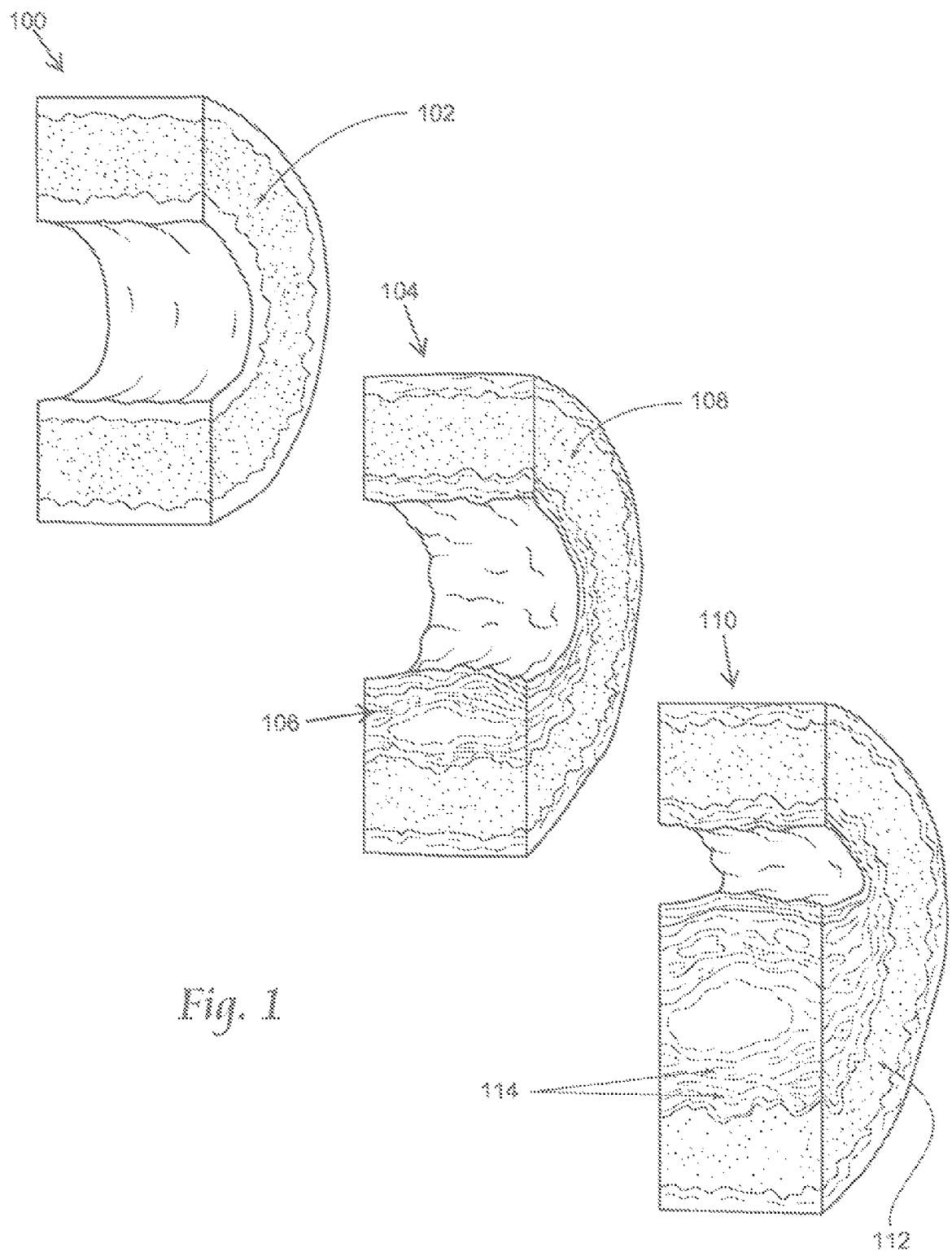
FIG. 1 shows anatomic views of segments of an artery, cut in section, to illustrate different degrees of atherosclerosis.

Passive steering may be accomplished without advancement of the inner catheter shaft, when the cutter assembly (2006) encounters a bend in the intravascular path (see FIG. 19F-1). Once the cutter assembly approaches or contacts the bend, the caregiver may rotate the outer catheter body (and thus the deflected catheter assembly) into an orientation in which the preferential deflection direction faces away from the inside radius of the bend (see FIGS. 19F-2 and 19F-3). In the representative embodiment, this orientation may face the alignment key (2054) on the ferrule away from the inner radius of the bend (as can be seen in FIG. 19F-3). Due to the preferential bending properties of the catheter assembly when in this orientation, subsequent advancement of the outer catheter shaft, without concurrent advancement of the inner catheter shaft, may apply enough compression force to cause deflection of the catheter assembly in the preferential direction (i.e., away from the inside radius of the bend). Continuance of the compression force upon the catheter body may cause the catheter body to follow the passively deflected catheter assembly away from inside radius of the bend and into the bend itself (see FIGS. 19F-3 and 19F-4).

Successive bends in a tortuous path may be navigated in the same passive manner, by rotating the catheter body at each successive bend (e.g., by rotating the control knob or by rotation of the handle itself) to orient the preferential deflection of the catheter assembly away from the respective inner bend radius, and without the need to actively steer by manipulation of the inner catheter shaft.

In some variations, the catheter assembly (2004) may include one or more radiographic markings to indicate during radiographic guidance the orientation of the preferential bend direction of the catheter assembly, whether left, or right, or toward the viewer, or away from the viewer.

FIGS. 16A and 16B depict another variation of an atherectomy apparatus (1600) described here. As shown there, atherectomy apparatus (1600) may comprise a first catheter (1602), a second catheter (1604), and a cutter assembly (1605) attached to the first catheter (1602). The first catheter (1602) may be moveable relative to the second catheter (1604) to move a distal portion of the atherectomy apparatus (1600) between an undeflected configuration (as shown in FIG. 16A) and a deflected configuration (as shown in FIG. 16B). In the variation of atherectomy apparatus (1600) shown in FIGS. 16A and 16B, the first catheter (1602) may be moveable within the second catheter (1604), although it should be appreciated that in other variations the second catheter (1604) may be slidable within the first catheter (1602).

Generally, a distal portion (1606) of the second catheter (1604) may be shaped to take on a deflected position as shown in FIG. 16B. Specifically, the deflected distal portion (1606) may comprise a double curve having a first proximal curve (1608) and a second distal curve (1610). As shown there, the first curve (1608) may bend the distal portion (1606) away from the longitudinal axis (1612) of a proximal portion of the second catheter (1604), while the second curve (1610) may bend the distal portion (1606) in a direction toward the longitudinal axis (1612). The double-curve configuration of the distal portion (1606) may allow the second curve (1610) to contact or otherwise rest against a wall (1614) of a blood vessel (1616), as shown in FIG. 16B. Additionally, this may angle the cutter assembly (1605) toward an opposite vessel wall (1618) during cutting. In instances when the atherectomy apparatus (1600) is advanced over a guide wire (1620) as shown in FIG. 16B, the guide wire (1620) may contact the opposite vessel wall (1618) and may help to prevent the cutter assembly (1605) from directly contacting and/or damaging the vessel wall (1618). In some instances, the double-curve configuration of the distal portion (1606) may allow for advancement of the distal portion (1606) while deflected while minimizing the risk that the cutter assembly (1605) may catch on tissue and retroflex.

As mentioned above, the first catheter (1602) may be moved relative to the second catheter (1604) to move the atherectomy apparatus between deflected and undeflected configurations. Specifically, the first catheter (1602) may comprise a distal portion (1622) and a proximal portion (not shown), where the distal portion (1622) is more flexible than the proximal portion. Additionally, the distal portion (1622) of the first catheter (1602) may be more flexible than the distal portion (1606) of the second catheter (1604), while the proximal portion of the first catheter (1602) may be stiffer than the distal portion (1606) of the second catheter (1604). Accordingly, the first catheter (1602) may be advanced such that the flexible distal portion (1622) of the first catheter (1602) extends beyond the distal end of the second catheter (1604), which may the proximal portion of the first catheter (1602) within the distal portion (1606) of the second catheter (1604) (or around the distal portion (1606) of the second catheter (1604) in variations where the second catheter (1604) is positioned inside the first catheter (1602). Because the proximal portion of the first catheter (1602) is stiffer than the distal portion of the second catheter (1604), axial alignment of these catheter segments may cause the proximal portion of the first catheter (1602) to straighten out the curves of the distal portion of the second catheter (1604), thereby placing the atherectomy apparatus (1600) in an undeflected configuration, as shown in FIG. 16A. Because the flexible distal portion of the first catheter (1602) extends beyond the distal portion of the second catheter (1604) when in an undeflected configuration, it may be used to track the cutter assembly (1605) along a guide wire during navigation of the atherectomy apparatus (1600) through the vasculature. Additionally, the atherectomy apparatus (1600) may be advanced while cutting to cut along the path of the guide wire (which may be a straight path in some instances), as described in more detail below. The atherectomy apparatus (1600) may then be withdrawn and deflected to cut a larger path through occlusive material (not shown), such as described below.

To move the atherectomy apparatus to a deflected configuration, the first catheter (1602) may be withdrawn to place the flexible distal portion (1622) of the first catheter (1602) in axial alignment with the distal portion (1606) of the second catheter (1604). Because the distal portion (1606) of the second catheter (1604) is stiffer than the distal portion (1622) of the first catheter (1602), the second catheter (1604) may cause the flexible distal portion (1622) of the first catheter (1602) to take on the dual-curve configuration described above with respect to FIG. 16B.

III. Methods of Use

A. Atherectomy in Peripheral Regions (i) Overview

When atherectomy is indicated, an intravascular atherectomy device as described herein can be introduced into a left or right limb through an iliac artery by an ipsilateral (same side) or a contralateral (opposite side) approach. In some variations, the atherectomy device may be advanced over a guide wire, through a guide sheath, and into the blood vessel. A user may manipulate a handle of the atherectomy apparatus to advance and navigate the device, and in some instances the advancement may be aided by radiographic visualization to gain access to the targeted treatment region, where occlusive materials are located.

The atherectomy device can be advanced distally through the CFA and into the SFA and, in some variations, further at or below the knee. In some variations, a catheter body/catheter assembly may have sufficient trackability to follow the guide wire through the often tortuous intravascular paths to the region targeted for treatment. The catheter body/catheter assembly may also have pushability, pullability, and torquability to allow the cutter assembly to be pushed, pulled, and/or rotated through occlusive material in the vessels. The trackability of the catheter body while being pushed, pulled, and rotated through occlusive material may allow the atherectomy apparatus to reliably follow the path of the guide wire.

A family of atherectomy apparatus can be provided having these combinations of technical features, sized according to the anatomy to be treated and the guide sheaths to be used. For example, an atherectomy apparatus comprising a 1.8 mm cutter assembly supported on the distal end of a 1.6 mm catheter body may be deployed through a 5 F or larger guide sheath for access to smaller vessels (e.g., 2.5 mm to 3.0 mm)

for removal of occlusive materials in one or more straight passes (e.g., without deflection) through the occlusive materials. Additionally or alternatively, an atherectomy apparatus comprising a 2.2 mm cutter assembly supported on the distal end of a 1.6 mm catheter body, may be deployed through a 6 F or larger guide sheath for access to larger vessels (e.g., 3.0 mm to 4.0 mm) for removal of occlusive materials in one or more straight passes through the occlusive materials. Additionally or alternatively, an atherectomy apparatus comprising a 2.4 mm cutter assembly supported on the distal end of a 2.2 mm catheter body, may be deployed through a 7 F or larger guide sheath for access to larger vessels (e.g., 3.0 mm to 4.5 mm) for removal of occlusive materials one or more straight passes through the occlusive materials.

(ii) Increasing Luminal Gain by Deflection and Sweeping

If desired, a given atherectomy apparatus may be sized and configured to be deflected and swept, so that the cutter assembly be deflected and swept while cutting occlusive materials. For example, a deflectable 2.4 mm cutter assembly supported on the distal end of a 2.2 mm catheter body can include may be deployed through a 7 F guide sheath to remove occlusive materials in still larger vessels (e.g., 4.0 mm to 7.0 mm). A deflectable cutter assembly may allow a specific atherectomy apparatus to treat a range of vessel size or vessels that may be asymmetric. By deflecting the distal cutter assembly in a controlled fashion in situ, the caregiver may be able to purposefully point the cutter assembly toward a particular region of the lesion, which may be useful in treating asymmetric vessels.

(iii) Treating Chronic Total Occlusions

Through progressive plaque growth or fibrotic organization of occlusive thrombus, atherosclerosis may result in chronic total occlusion (CTO) of a major arterial conduit. The success of catheter-based treatment techniques may depend significantly upon the nature of the occlusion (e.g., its length, duration, tortuosity, and degree of calcification). Devices sized and configured to cross CTO's preferably possess an ability to distinguish a true luminal path from one created within (dissection) or through (perforation) the vessel wall of the occluded segment; an ability to change direction (steer) to correct deviations from the desired path through the occlusion; and an ability to penetrate the frequently fibrotic and focally calcified substance of the occlusion through the use of high cutting efficiency and mechanical stiffness.

Figure 25A:
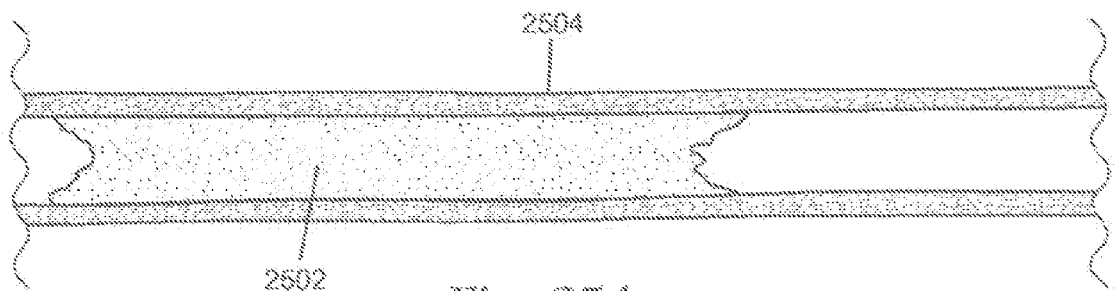
FIGS. 25A-25D depict an illustrative method by which the atherectomy systems described here may be used to treat a chronic total occlusion in a blood vessel.
Figure 25B:
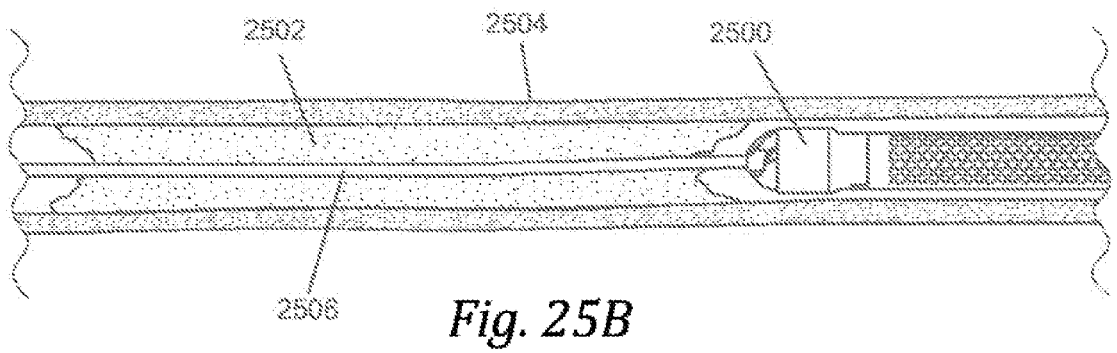
Figure 25C:
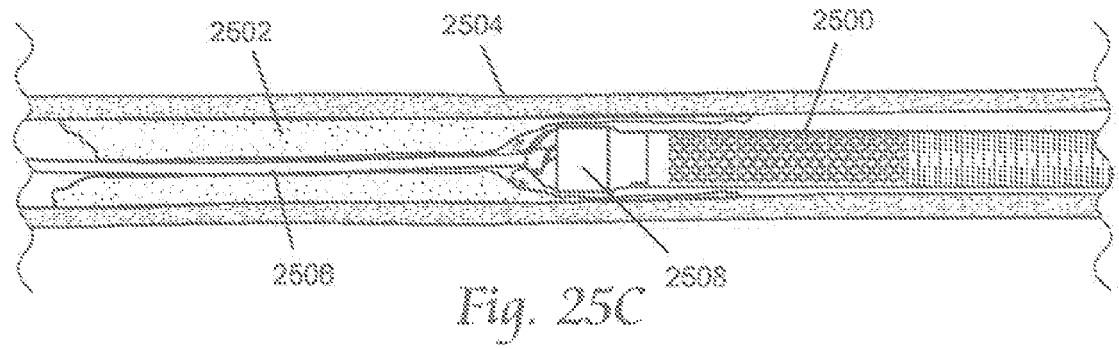
Figure 25D:
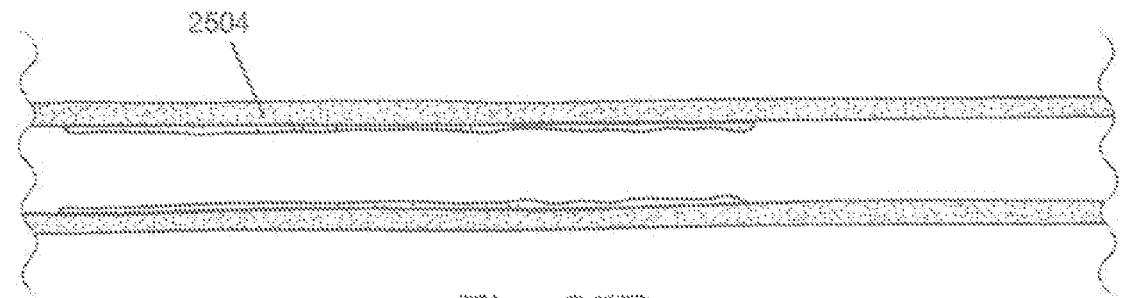

The technical features of the highly efficient cutting elements disclosed herein, in combination with the degree of trackability coupled with pushability, pullability, and toquability of the catheter bodies disclosed herein, may allow the atherectomy apparatus to be tailored for use to treat CTO's in the vasculature. For example, FIGS. 25A-25D show one manner in which an atherectomy apparatus (2500) (such as one or more of the atherectomy apparatuses described previously) may treat a CTO (2502) in a blood vessel (2504) (depicted in FIG. 25A). As shown in FIGS. 25B and 25C, the atherectomy apparatus (2500) may be advanced (for example, along a guide wire (2506)) while operating a cutter assembly (2508) of the atherectomy apparatus (2500). While cutting, occlusive material of the CTO (2502) may be cut and conveyed proximally through the atherectomy apparatus (2500). The trackability, pushability, pullability, and torquability of the atherectomy apparatus (2500) may allow it to follow the path of the guide wire (2506) to recanalize the vessel (2504) (as shown in FIG. 25D).

The atherectomy apparatus described herein may possess the combination of technical features that may be optimized to cross a CTO and reenter the distal true lumen from a subintimal location over a guide wire.

(iv) Delivery of Bioactive Materials

It may be desirable, in conjunction with using the atherectomy apparatus as described above, to introduce into the region a bioactive material, comprising, for example, a restenosis-inhibiting agent, a thrombus-inhibiting agent, an anti-inflammatory agent, combinations thereof and the like. The bioactive material can be introduced as a coating on a balloon that may be expanded into contact with the region to deliver the bioactive material, and/or may be delivered using the atherectomy apparatus.

B. Atherectomy to Treat In-Stent Restenosis

Figure 26A:
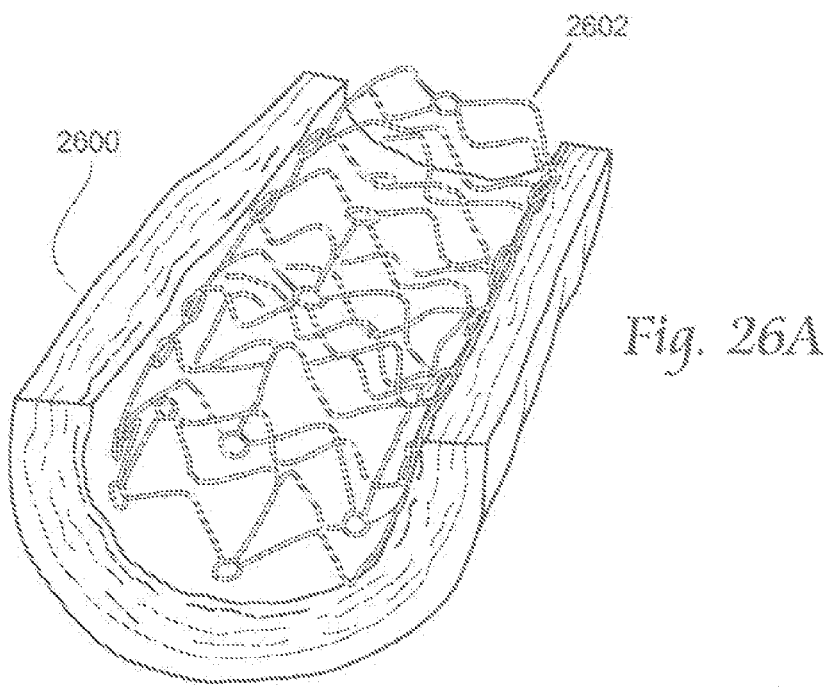
FIGS. 26A-26F depict a method by which the atherectomy systems described here may be used to treat in-stent restenosis.

In some variations, the atherectomy systems described herein may be used to treat in-stent restenosis. As described in more detail above, in some instances a stent may be placed in a blood vessel (e.g., following angioplasty). Generally, the stent may act to hold an artery open. For example, FIG. 26A depicts a section of an artery (2600) with a stent (2602) positioned therein.

When a stent is placed in a blood vessel, new tissue may grow inside the stent, and may cover one or more portions of the stent. Initially, this new tissue may include healthy cells from the lining of the arterial wall, which may allow blood to flow smoothly over the stented area without clotting. In some instances, scar tissue or other occlusive material may later form underneath the new healthy lining, and may obstruct the blood flow through the vessel. This condition may be referred to as "in-stent restenosis". For example, FIGS. 26B and 26C show a cross-sectional perspective view and a cross-section side view respectively of the artery (2600) and stent (2602), with occlusive tissue (2604) growing within the stent (2602).

The occlusive tissue (2604) within the stent (2602) is typically hyperplastic, smooth muscle tissue, with little calcium, having the rubbery, elastic properties of occlusive materials having less calcium, with a consistency that is fibrous and fleshy. For this reason, it may be desirable for the atherectomy apparatus in these methods to comprise at least one cutting flute having a positive rake angle, such as one or more of the high rake angle cutting elements described above. Additionally, in some variations it may be desirable for a cutting element to have an atraumatic rounded profile (e.g., the hemispherical profile of the first cutting elements described in more detail above). Cutting elements having a rounded profile and positive rake angle cutting elements may help prevent a cutting assembly from damaging or otherwise negatively interacting with a stent placed in the vessel.

Figure 26B:
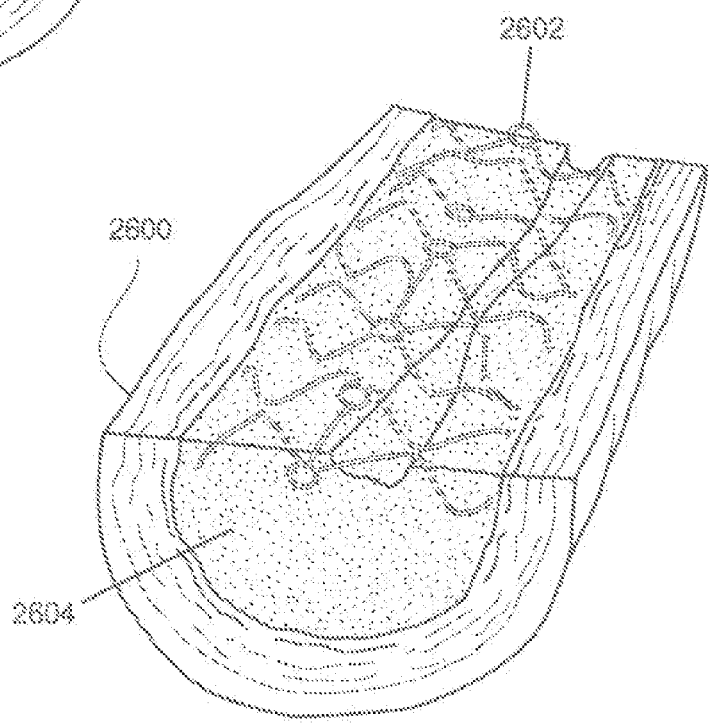
Figure 26C:
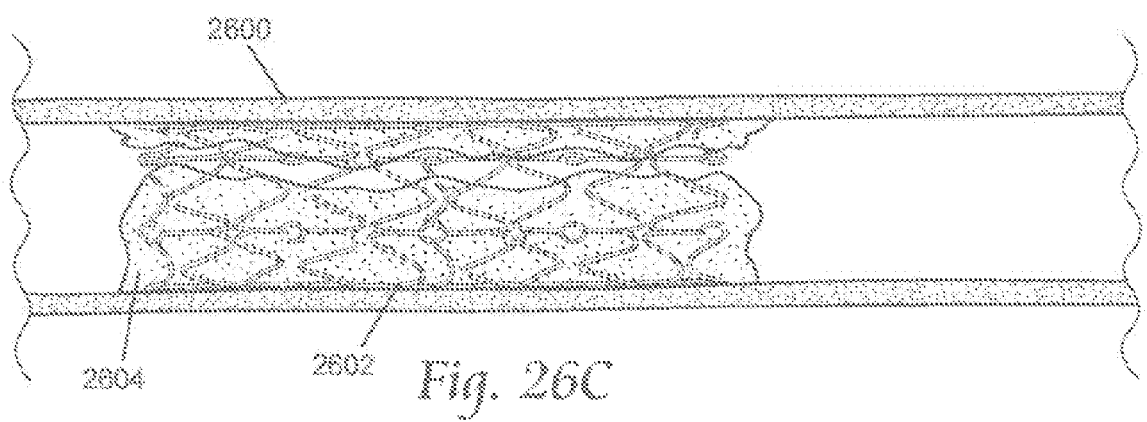
Figure 26D:
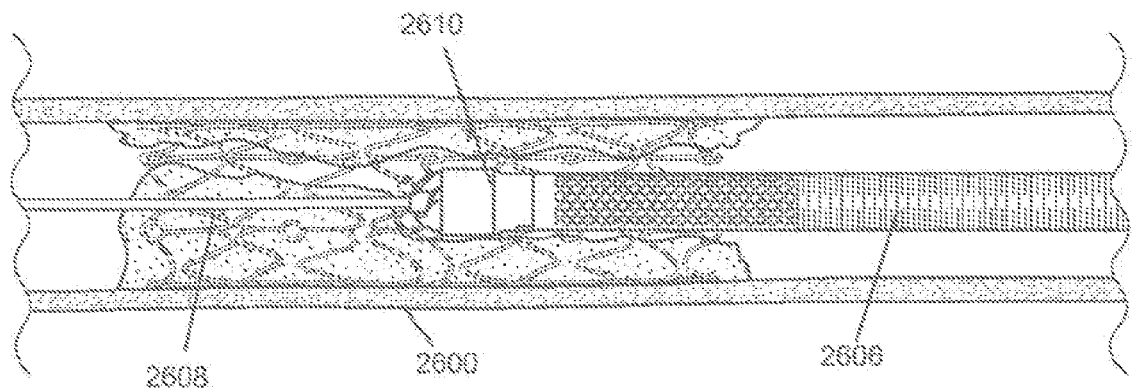
Figure 26E:
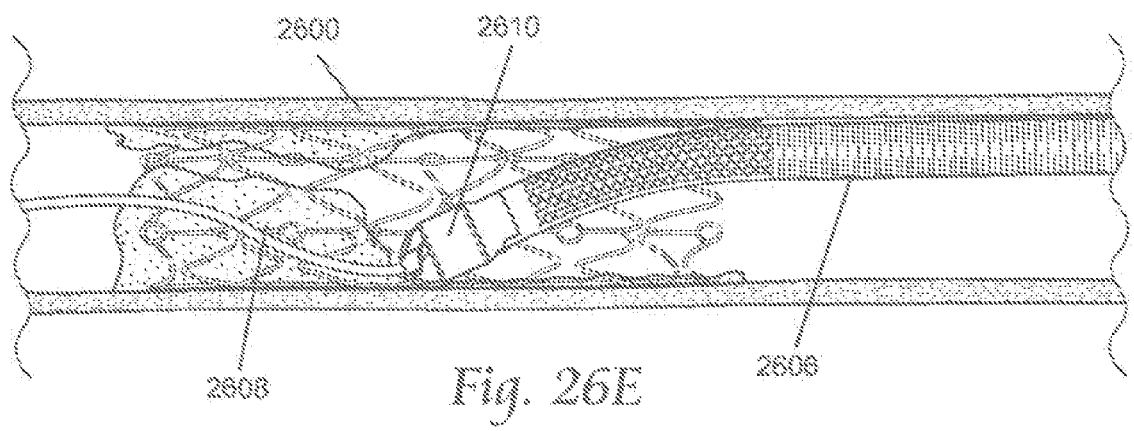
Figure 26F:
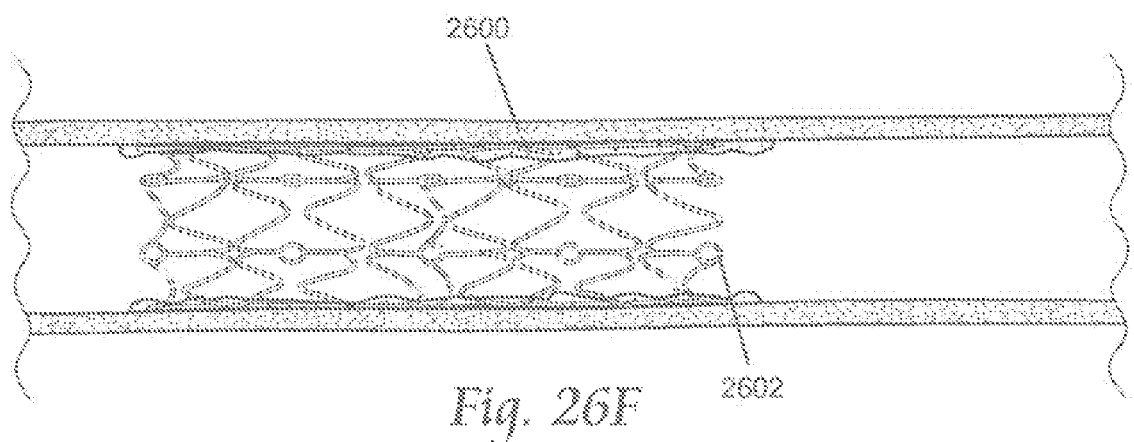

FIGS. 26D-26F depict one method by which an atherectomy apparatus (2606) (which may be one or more of the atherectomy systems described in more detail above) may be used to treat in-stent restenosis of the artery (2600) depicted in FIGS. 26B and 26C. As shown there, a guide wire (2608) may be introduced into the artery (2600) and through the occlusive material (2604). The atherectomy apparatus (2606) may be advanced along the guide wire (2608) and at least partially through the occlusive material (2604), as shown in FIG. 26D. A cutter assembly (2610) of the atherectomy apparatus (2606) may be operated during advancement through the occlusive material to cut the occlusive material (2604) and convey cut material proximally, as described in more detail above (e.g., a conveyor element may convey the tissue from the restenosis proximally along the catheter body for discharge, which may occur without supplement of a vacuum pump).

In variations where the atherectomy apparatus (2606) is configured to selectively deflect a distal portion of the atherectomy apparatus (2606), the distal end of the atherectomy apparatus (2606) may be deflected and rotated to sweep the cutter in an arc. The cutter assembly (2610) may be operated during deflection and rotation to cut tissue in a region larger than an outer diameter of the cutter assembly (2610, as shown in FIG. 26E. This may be performed along the length of the occlusive material to clear the restenosis within the stent (2602), as shown in FIG. 26F. The result may be the clearing of the restenosis within the stent (see FIG. 26F). In some of these variations, the atherectomy apparatus (2606) may be advanced in an undeflected configuration along the path of the guide wire (2608) while cutting tissue, may be proximally withdrawn, and may be deflected and swept to cut tissue in a larger path around the atherectomy device. The atherectomy apparatus (2606) may be distally advanced while sweeping, or the sweeping and distal advancement may be performed as separate steps.

It may be desirable, in conjunction with using the atherectomy apparatus as described above, to introduce into the region a bioactive material, comprising, for example, a restenosis-inhibiting agent, a thrombus-inhibiting agent, an anti-inflammatory agent, combinations thereof and the like. The bioactive material can be introduced as a coating on a balloon that may be expanded into contact with the region to deliver the bioactive material, and/or may be delivered using the atherectomy apparatus.

The region of restenosis can comprise a peripheral blood vessel, e.g., a peripheral blood vessel in a leg above, at, or below the knee. Additionally, while described immediately above to treat in-stent restenosis, it should also be appreciated that the methods described here may be used to treat restenosis of a vessel that does not include a stent.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention.

We claim:

1. A method for performing an atherectomy comprising:
introducing an atherectomy device into a blood vessel, wherein the atherectomy device comprises a handle, a catheter, and a cutter assembly, wherein the cutter assembly comprises a cutter housing and a cutter configured to rotate within the housing, wherein the cutter comprises at least one helical flute forming a cutting blade having a positive rake angle, wherein the positive rake angle is between 60 degrees and 80 degrees, and wherein the cutter comprises a first cutting element and a second cutting element, wherein the first cutting element has at least a first portion having an outside diameter greater than or equal to an outside diameter of the cutter housing;
advancing the cutter assembly to a targeted region having occlusive material; and
rotating the cutter to cut the occlusive material.

2. The method of claim 1 wherein the positive rake angle is about 70 degrees.

3. The method of claim 1 wherein the first cutting element comprises at least two helical flutes.

4. The method of claim 3 wherein the second cutting element comprises at least two helical flutes.

5. The method of claim 1 wherein at least a portion of the first cutter element extends from an opening in the cutter housing.

6. The method of claim 5 wherein the portion of the first cutter element extending from the opening in the cutter housing has a hemispherical profile.

7. The method of claim 1 wherein the cutting blade has a relief angle less than or equal to about 10 degrees.

8. The method of claim 7 wherein the relief angle is about 0 degrees.

9. The method of claim 1 wherein the cutting blade has a flute angle less than or equal to about 30 degrees.

10. The method of claim 1 wherein the cutting blade has a helix angle between 30 degrees and 60 degrees.

\* \* \* \* \*